United States Patent
Cha et al.

(10) Patent No.: US 10,862,045 B2
(45) Date of Patent: Dec. 8, 2020

(54) AMINE-BASED COMPOUND AND ORGANIC LIGHT-EMITTING ELEMENT COMPRISING SAME

(71) Applicant: LG Chem, Ltd., Seoul (KR)

(72) Inventors: Yongbum Cha, Daejeon (KR); Sung Kil Hong, Daejeon (KR); Jungbum Kim, Daejeon (KR); Jin Joo Kim, Daejeon (KR)

(73) Assignee: LG Chem, Ltd.

( * ) Notice: Subject to any disclaimer, the term of this patent is extended or adjusted under 35 U.S.C. 154(b) by 299 days.

(21) Appl. No.: 15/760,923

(22) PCT Filed: Sep. 13, 2016

(86) PCT No.: PCT/KR2016/010351
§ 371 (c)(1),
(2) Date: Mar. 16, 2018

(87) PCT Pub. No.: WO2017/052138
PCT Pub. Date: Mar. 30, 2017

(65) Prior Publication Data
US 2018/0269401 A1     Sep. 20, 2018

(30) Foreign Application Priority Data

Sep. 25, 2015   (KR) .................. 10-2015-0137124

(51) Int. Cl.
*H01L 51/50* (2006.01)
*H01L 51/00* (2006.01)
(Continued)

(52) U.S. Cl.
CPC ........ *H01L 51/0061* (2013.01); *C07D 209/86* (2013.01); *C07D 209/88* (2013.01); *C09K 11/06* (2013.01); *H01L 51/006* (2013.01); *H01L 51/50* (2013.01); *C09K 2211/1018* (2013.01); *H01L 51/0054* (2013.01); *H01L 51/0058* (2013.01); *H01L 51/0072* (2013.01); *H01L 51/5016* (2013.01); *H01L 51/5056* (2013.01);
(Continued)

(58) Field of Classification Search
None
See application file for complete search history.

(56) References Cited

U.S. PATENT DOCUMENTS

2013/0207092 A1* 8/2013 Huh ................. C09K 11/06
257/40
2013/0256649 A1* 10/2013 Huh ................. C07D 333/76
257/40
(Continued)

FOREIGN PATENT DOCUMENTS

| CN | 104220555 A | 12/2014 |
|----|-------------|---------|
| JP | 2008195841 A | 8/2008 |

(Continued)

OTHER PUBLICATIONS

Search report from International Application No. PCT/KR2016/010351, dated Feb. 22, 2017.

*Primary Examiner* — Gregory D Clark
(74) *Attorney, Agent, or Firm* — Lerner, David, Littenberg, Krumholz & Mentlik, LLP

(57) ABSTRACT

The present specification provides an amine-based compound and an organic light emitting device comprising the same.

16 Claims, 1 Drawing Sheet

(51) Int. Cl.
*C09K 11/06* (2006.01)
*C07D 209/86* (2006.01)
*C07D 209/88* (2006.01)

(52) U.S. Cl.
CPC ...... *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | |
|---|---|---|
| 2015/0179950 A1 | 6/2015 | Miyata |
| 2015/0179956 A1 | 6/2015 | Miyata et al. |

FOREIGN PATENT DOCUMENTS

| | | | |
|---|---|---|---|
| KR | 20000051826 A | | 8/2000 |
| KR | 20140130297 A | | 11/2014 |
| KR | 20150010016 A | | 1/2015 |
| KR | 20150073062 A | | 6/2015 |
| WO | 2012039534 A1 | | 3/2012 |
| WO | 2012091428 A2 | | 7/2012 |
| WO | 2015009076 A1 | | 1/2015 |

\* cited by examiner

[Figure 1]
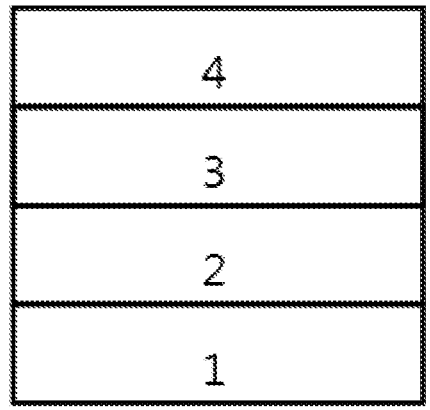
[Figure 2]
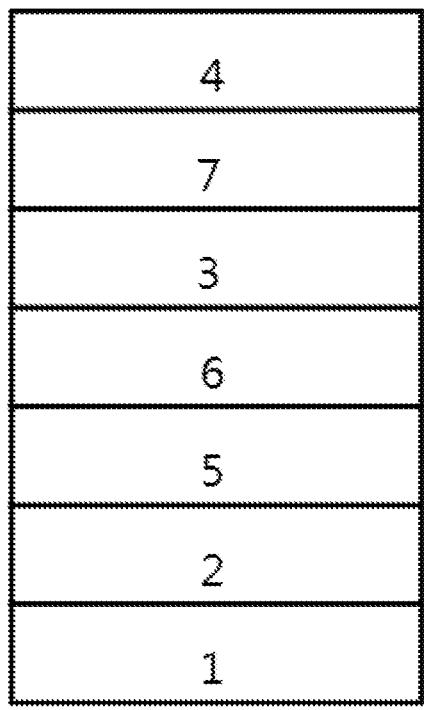

AMINE-BASED COMPOUND AND ORGANIC LIGHT-EMITTING ELEMENT COMPRISING SAME

CROSS-REFERENCE TO RELATED APPLICATIONS

This application is a national phase entry under 35 U.S.C. § 371 of International Application No. PCT/KR2016/010351, filed Sep. 13, 2016, which claims priority to Korean Patent Application No. 10-2015-0137124, filed Sep. 25, 2015, the disclosures of which are incorporated herein by reference.

TECHNICAL FIELD

The present specification claims priority to and the benefit of Korean Patent Application No. 10-2015-0137124 filed in the Korean Intellectual Property Office on Sep. 25, 2015, the entire contents of which are incorporated herein by reference.

The present specification relates to an amine-based compound and an organic light emitting device comprising the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

DISCLOSURE

Technical Problem

The present specification describes an amine-based compound and an organic light emitting device comprising the same.

Technical Solution

An exemplary embodiment of the present specification provides a compound represented by the following Chemical Formula 1:

Chemical Formula 1 in Chemical Formula 1,

Y is

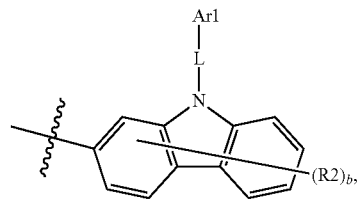

Y is

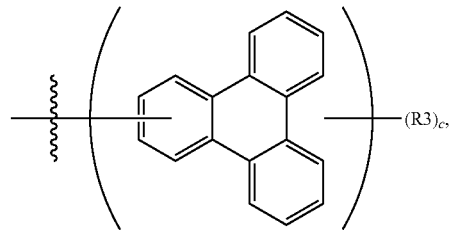

Z is

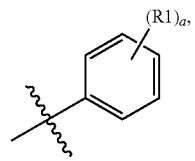

Ar1 is a substituted or unsubstituted aryl group,

L is a direct bond; or a substituted or unsubstituted arylene group,

R1 is hydrogen; deuterium; or a substituted or unsubstituted alkyl group,

R2 and R3 are the same as or different from each other, and are each independently hydrogen; a substituted or unsubstituted alkyl group; or a substituted or unsubstituted aryl group, a is an integer of 0 to 5, b is an integer of 0 to 7, c is an integer of 0 to 11, and when a is 2 or more, R1's are the same as or different from each other, when b is 2 or more, R2's are the same as or different from each other, and when c is 2 or more, R3's are the same as or different from each other.

Further, an exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

Advantageous Effects

The compound described in the present specification may be used as a material for an organic material layer of an organic light emitting device. The compound according to at least one exemplary embodiment may improve the efficiency, achieve low driving voltage and/or improve lifetime characteristics in the organic light emitting device. In particular, the compound described in the present specification may be used as a material for hole injection, hole transport, hole injection and hole transport, electron blocking, light emission, hole inhibition, electron transport, or electron injection.

DESCRIPTION OF DRAWINGS

FIG. 1 illustrates an example of an organic light emitting device composed of a substrate (1), a positive electrode (2), a light emitting layer (3), and a negative electrode (4).

FIG. 2 illustrates an example of an organic light emitting device composed of a substrate (1), a positive electrode (2), a hole injection layer (5), a hole transport layer (6), a light emitting layer (3), an electron transport layer (7), and a negative electrode (4).
- 1: Substrate
- 2: Positive electrode
- 3: Light emitting layer
- 4: Negative electrode
- 5: Hole injection layer
- 6: Hole transport layer
- 7: Electron transport layer

MODE FOR INVENTION

Hereinafter, the present specification will be described in more detail.

An exemplary embodiment of the present specification provides the compound represented by Chemical Formula 1.

In the present specification,

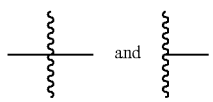

mean a moiety linked to another substituent.

Examples of the substituents will be described below, but are not limited thereto.

In the present specification, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; a germanium group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine.

In the present specification, the number of carbon atoms of a carbonyl group is not particularly limited, but is preferably 1 to 40. Specifically, the carbonyl group may be a compound having the following structures, but is not limited thereto.

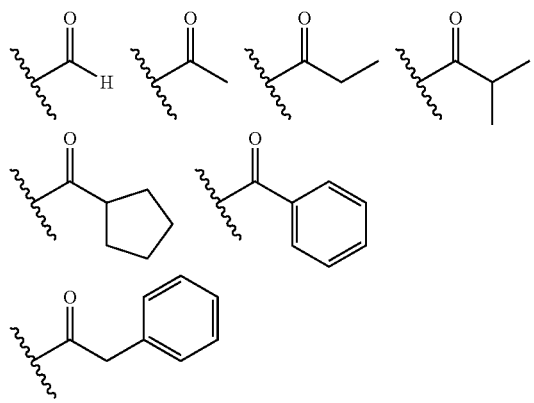

In the present specification, for an ester group, the oxygen of the ester group may be substituted with a straight-chained, branch-chained, or cyclic alkyl group having 1 to 40 carbon atoms, or an aryl group having 6 to 30 carbon atoms. Specifically, the ester group may be a compound having the following structural formulae, but is not limited thereto.

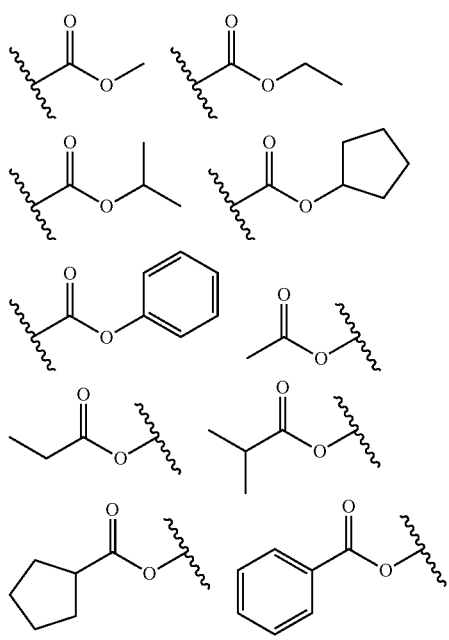

In the present specification, the number of carbon atoms of an imide group is not particularly limited, but is preferably 1 to 25. Specifically, the imide group may be a compound having the following structures, but is not limited thereto.

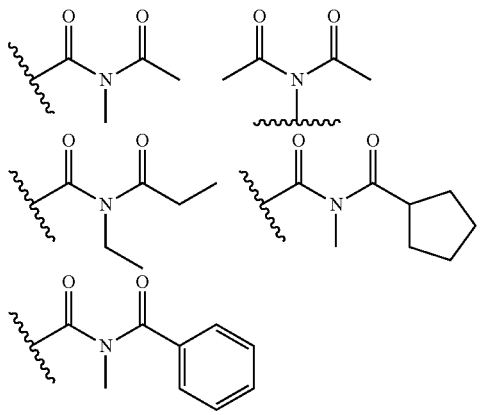

In the present specification, a silyl group may be represented by a chemical formula of —$SiR_aR_bR_c$, and $R_a$, $R_b$, and $R_c$ may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, propyldimethylsilyl group, a triphenylsilyl group, a diphenylsilyl group, a phenylsilyl group, and the like, but are not limited thereto.

In the present specification, a boron group may be represented by a chemical formula of —$BR_aR_b$, and $R_a$ and $R_b$ may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, the alkyl group may be straight-chained or branch-chained, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include a methyl group, an ethyl group, a propyl group, an n-propyl group, an isopropyl group, butyl group, an n-butyl group, an isobutyl group, a tert-butyl group, a sec-butyl group, a 1-methyl-butyl group, an 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 4-methylhexyl group, a 5-methylhexyl group, and the like, but are not limited thereto.

In the present specification, the alkoxy group may be straight-chained, branch-chained, or cyclic. The number of carbon atoms of the alkoxy group is not particularly limited, but is preferably 1 to 40. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

A substituent including an alkyl group, an alkoxy group, and other alkyl group moieties described in the present specification includes both a straight-chained form and a branch-chained form.

In the present specification, the alkenyl group may be straight-chained or branch-chained, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 1 According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 40. According to another exemplary embodiment, the number of carbon atoms of the cycloalkyl group is 3 to 20. According to still another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclohexyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the number of carbon atoms of an alkylamine group is not particularly limited, but is preferably 1 to 40. Specific examples of the alkylamine group include a methylamine group, a dimethylamine group, an ethylamine group, a diethylamine group, a phenylamine group, a naphthylamine group, biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, examples of a heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a polycyclic heterocyclic group. The heteroarylamine group including two or more heterocyclic groups may include a monocyclic heterocyclic group, a polycyclic heterocyclic group, or both a monocyclic heterocyclic group and a polycyclic heterocyclic group.

In the present specification, examples of an arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including two or more aryl groups may include a monocyclic aryl group, a polycyclic aryl group, or both a monocyclic aryl group and a polycyclic aryl group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a triphenyl group, a chrysenyl group, a fluorenyl group, and the like, but are not limited thereto.

In the present specification, a fluorenyl group may be substituted, and two substituents may combine with each other to form a Spiro structure.

When the fluorenyl group is substituted, the fluorenyl group may be a spiro fluorenyl group such as

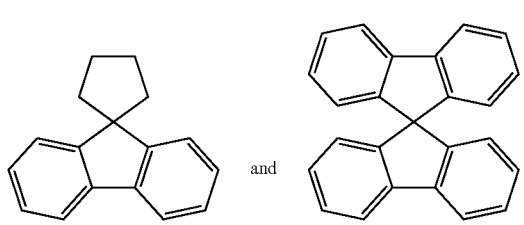

and a substituted fluorenyl group such as

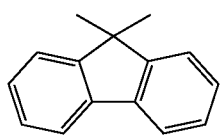

(a 9,9-dimethylfluorenyl group) and

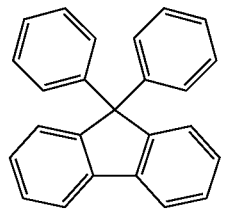 [SMILES: c1ccc(C2(c3ccccc3)c3ccccc3-c3ccccc32)cc1]

(a 9,9-diphenylfluorenyl group). However, the fluorenyl group is not limited thereto.

In the present specification, a heterocyclic group is a heterocyclic group including one or more of N, O, P, S, Si, and Se as a hetero atom, and the number of carbon atoms thereof is not particularly limited, but is preferably 1 to 60. According to an exemplary embodiment, the number of carbon atoms of the heterocyclic group is 1 to 30. Examples of the heterocyclic group include a pyridyl group, a pyrrole group, a pyrimidyl group, a pyridazinyl group, a furanyl group, a thiophenyl group, an imidazole group, a pyrazole group, an oxazole group, an isooxazole group, a triazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a thiazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acrydyl group, a xanthenyl group, a phenanthridinyl group, a diaza naphthalenyl group, a triazaindenyl group, an indole group, an indolinyl group, an indolizinyl group, a phthalizinyl group, a pyrido pyrimidinyl group, a pyrido pyrazinyl group, a pyrazino pyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzoimidazoquinazoline group, or a benzoimidazophenanthridine group, and the like, but are not limited thereto.

In the present specification, the above-described description on the heterocyclic group may be applied to a heteroaryl group except for an aromatic heteroaryl group.

In the present specification, the above-described description on the aryl group may be applied to an aryl group in an aryloxy group, an arylthioxy group, an arylsulfoxy group, an arylphosphine group, an aralkyl group, an aralkylamine group, an aralkenyl group, an alkylaryl group, an arylamine group, and an arylheteroarylamine group.

In the present specification, the above-described description on the alkyl group may be applied to an alkyl group in an alkylthioxy group, an alkylsulfoxy group, an aralkyl group, an aralkylamine group, an alkylaryl group, and an alkylamine group.

In the present specification, the above-described description on the heterocyclic group may be applied to a heteroaryl group in a heteroaryl group, a heteroarylamine group, and an arylheteroarylamine group.

In the present specification, a germanium group may be represented by a chemical formula of —GeR$_a$R$_b$R$_c$, and R$_a$, R$_b$, and R$_c$ may be each hydrogen; a substituted or unsubstituted alkyl group; or a substituted or unsubstituted aryl group. Specific examples of the germanium group include a trimethylgermanium group, a triethylgermanium group, a t-butyldimethylgermanium group, and the like, but are not limited thereto.

In the present specification, the above-described description on the alkenyl group may be applied to an alkenyl group in an aralkenyl group.

In the present specification, the above-described description on the aryl group may be applied to arylene except for a divalent arylene group.

In the present specification, the above-described description on the heteroaryl group may be applied to heteroarylene except for a divalent heteroarylene group.

In the present specification, the meaning of combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a fused ring thereof.

In the present specification, the aliphatic hydrocarbon ring means a ring composed only of carbon and hydrogen atoms as a ring which is not an aromatic group. Specifically, examples of the aliphatic hydrocarbon ring include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene, and the like, but are not limited thereto.

In the present specification, an aromatic hydrocarbon ring means an aromatic ring composed only of carbon and hydrogen atoms. Specifically, examples of the aromatic hydrocarbon ring include benzene, naphthalene, anthracene, phenanthrene, perylene, fluoranthene, triphenylene, phenalene, pyrene, tetracene, chrysene, pentacene, fluorene, indene, acenaphthylene, benzofluorene, spirofluorene, and the like, but are not limited thereto.

In the present specification, the aliphatic hetero ring means an aliphatic ring including one or more of hetero atoms. Specifically, examples of the aliphatic hetero ring include oxirane, tetrahydrofuran, 1,4-dioxane, pyrrolidine, piperidine, morpholine, oxepane, azocane, thiocane, and the like, but are not limited thereto.

In the present specification, the aromatic hetero ring means an aromatic ring including one or more of hetero atoms. Specifically, examples of the aromatic hetero ring include pyridine, pyrrole, pyrimidine, pyridazine, furan, thiophene, imidazole, pyrazole, oxazole, isoxazole, thiazole, isothiazole, triazole, oxadiazole, thiadiazole, dithiazole, tetrazole, pyran, thiopyran, diazine, oxazine, thiazine, dioxine, triazine, tetrazine, isoquinoline, quinoline, quinol, quinazoline, quinoxaline, naphthyridine, acridine, phenanthridine, diaza naphthalene, triazaindene, indole, indolizine, benzothiazole, benzoxazole, benzoimidazole, benzothiophene, benzofuran, dibenzothiophene, dibenzofuran, carbazole, benzocarbazole, dibenzocarbazole, phenazine, imidazopyridine, phenoxazine, phenanthridine, indolocarbazole, indenocarbazole, and the like, but are not limited thereto.

In the present specification, the aliphatic hydrocarbon ring, the aromatic hydrocarbon ring, the aliphatic hetero ring, and the aromatic hetero ring may be monocyclic or polycyclic.

According to an exemplary embodiment of the present specification, the compound represented by Chemical Formula 1 may be represented by the following Chemical Formula 2 or Chemical Formula 3.

[Chemical Formula 2]

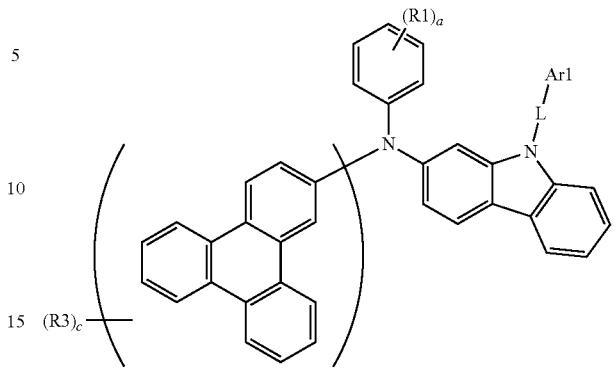

[Chemical Formula 3]

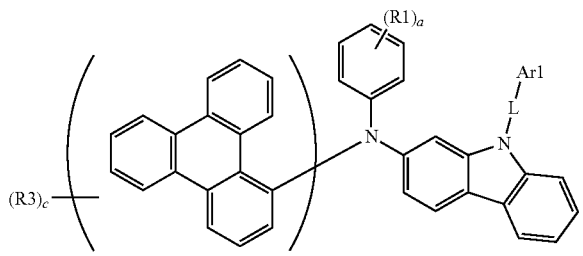

In Chemical Formula 2 and Chemical Formula 3, the definitions of Ar1, L, R1, R3, a and c are each the same as those in Chemical Formula 1.

According to an exemplary embodiment of the present specification, the compound represented by Chemical Formula 1 may be represented by the following Chemical Formula 4 or Chemical Formula 5.

[Chemical Formula 4]

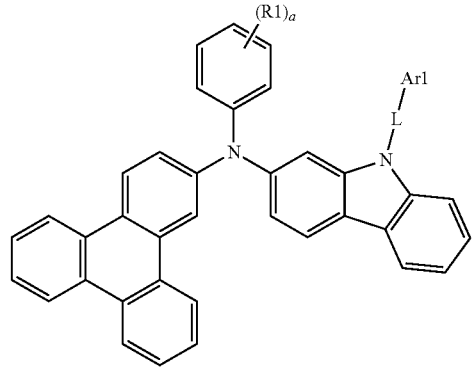

[Chemical Formula 5]

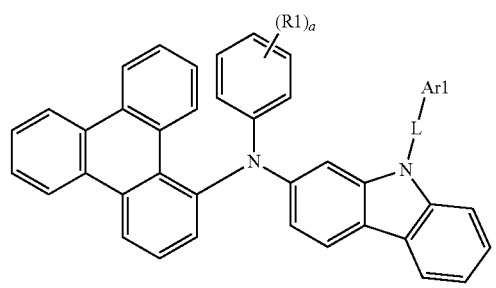

In Chemical Formula 4 and Chemical Formula 5, the definitions of Ar1, L, R1, and a are each the same as those in Chemical Formula 1.

According to an exemplary embodiment of the present invention, Ar1 is a substituted or unsubstituted monocyclic or polycyclic aryl group having 6 to 30 carbon atoms.

In an exemplary embodiment of the present invention, Ar1 is a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenanthryl group; a substituted or unsubstituted pyrenyl group; a substituted or unsubstituted perylenyl group; a substituted or unsubstituted chrysenyl group; or a substituted or unsubstituted fluorenyl group.

In an exemplary embodiment of the present invention, Ar1 is a substituted or unsubstituted phenyl group; a substituted or unsubstituted biphenyl group; a substituted or unsubstituted terphenyl group; a substituted or unsubstituted naphthyl group; a substituted or unsubstituted fluorenyl group; a substituted or unsubstituted phenanthrenyl group; or a substituted or unsubstituted triphenylenyl group.

According to an exemplary embodiment of the present specification, Ar1 may be any one selected from the following structures, and the following structures may be additionally substituted.

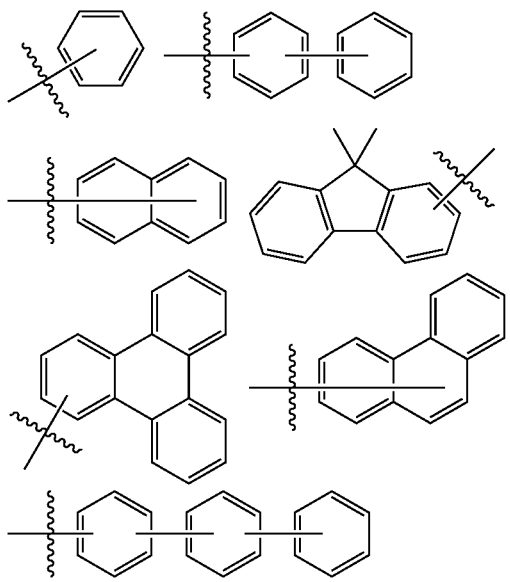

Specifically, the structures may be unsubstituted or substituted with one or more substituents selected from the group consisting of deuterium; a halogen group; a nitrile group; a nitro group; a hydroxy group; a carbonyl group; an ester group; an imide group; an amine group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group. More specifically, the structures may be unsubstituted or substituted with deuterium; an alkyl group; or an aryl group.

In an exemplary embodiment of the present invention, L is a direct bond; or a substituted or unsubstituted monocyclic or polycyclic arylene group having 6 to 30 carbon atoms.

In an exemplary embodiment of the present invention, L is a direct bond; a substituted or unsubstituted phenylene group; a substituted or unsubstituted biphenylylene group; a substituted or unsubstituted terphenylylene group; a substituted or unsubstituted naphthylene group; a substituted or unsubstituted anthracenylene group; a substituted or unsubstituted fluorenylene group; a substituted or unsubstituted phenanthrenylene group; or a substituted or unsubstituted triphenylenylene group.

In an exemplary embodiment of the present invention, L is a direct bond; or a substituted or unsubstituted phenylene group.

According to an exemplary embodiment of the present specification, L may be a direct bond; or any one selected from the following structures, and the following structures may be additionally substituted.

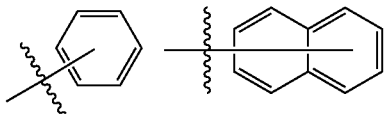

Specifically, the structures may be unsubstituted or substituted with one or more substituents selected from the group consisting of deuterium; a halogen group; a nitrile group; a nitro group; a hydroxy group; a carbonyl group; an ester group; an imide group; an amine group; a phosphine oxide group, an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group. More specifically, the structures may be unsubstituted or substituted with deuterium; an alkyl group; or an aryl group.

In an exemplary embodiment of the present invention, R1 is hydrogen; deuterium; or a substituted or unsubstituted alkyl group having 1 to 40 carbon atoms.

In an exemplary embodiment of the present invention, R1 is hydrogen; deuterium; a substituted or unsubstituted methyl group; a substituted or unsubstituted ethyl group; a substituted or unsubstituted propyl group; a substituted or unsubstituted n-propyl group; a substituted or unsubstituted isopropyl group; a substituted or unsubstituted butyl group; a substituted or unsubstituted n-butyl group; a substituted or unsubstituted isobutyl group; a substituted or unsubstituted tert-butyl group; a substituted or unsubstituted sec-butyl group; a substituted or unsubstituted 1-methyl-butyl group; a substituted or unsubstituted 1-ethyl-butyl group; a substituted or unsubstituted pentyl group; a substituted or unsubstituted n-pentyl group; a substituted or unsubstituted isopentyl group; a substituted or unsubstituted neopentyl group; a substituted or unsubstituted tert-pentyl group; a substituted or unsubstituted hexyl group; a substituted or unsubstituted n-hexyl group; a substituted or unsubstituted 1-methylpentyl group; a substituted or unsubstituted 2-methylpentyl group; a substituted or unsubstituted 4-methyl-2-pentyl group; a substituted or unsubstituted 3,3- dimethylbutyl group; a substituted or unsubstituted 2-ethylbutyl group; a substituted or unsubstituted heptyl group; a substituted or unsubstituted n-heptyl group; a substituted or unsubstituted 1-methylhexyl group; a substituted or unsubstituted cyclopentylmethyl group; a substituted or unsubstituted cyclohexylmethyl group; a substituted or unsubstituted octyl group; a substituted or unsubstituted n-octyl group; a substituted or unsubstituted tert-octyl group; a substituted or unsubstituted 1-methylheptyl group; a substituted or unsubstituted 2-ethylhexyl group; a substituted or unsubstituted 2-propylpentyl group; a substituted or unsubstituted n-nonyl group; a substituted or unsubstituted 2,2-dimethylheptyl group; a substituted or unsubstituted 1-ethyl-propyl group; a substituted or unsubstituted 1,1-dimethyl-propyl group; a substituted or unsubstituted isohexyl group; a substituted or unsubstituted 4-methylhexyl group; or a substituted or unsubstituted 5-methylhexyl group.

In an exemplary embodiment of the present invention, R1 is hydrogen; deuterium; a substituted or unsubstituted methyl group; or a substituted or unsubstituted t-butyl group.

In an exemplary embodiment of the present invention, R1 is hydrogen; deuterium; a methyl group; or a t-butyl group.

In an exemplary embodiment of the present invention, the compound of Chemical Formula 1 may be any one selected from the following compounds.

1

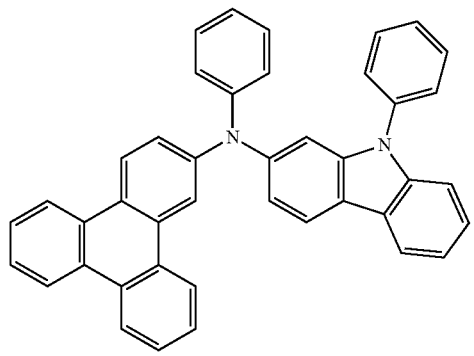

2

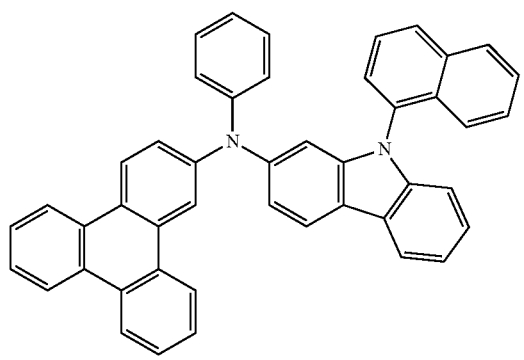

3

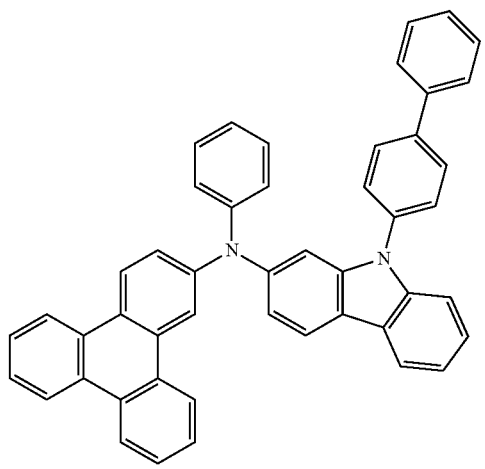

4

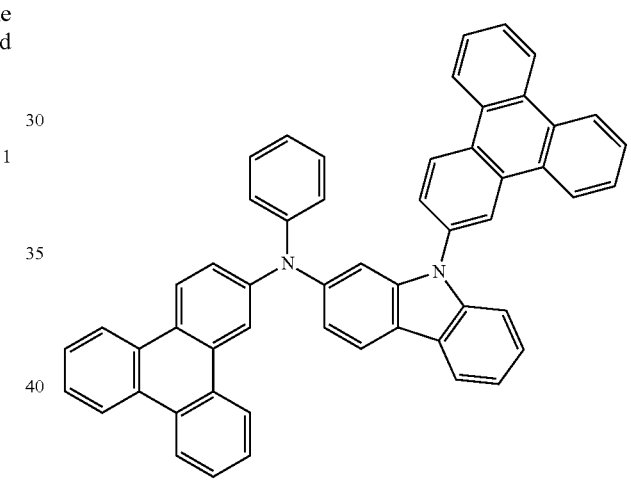

5

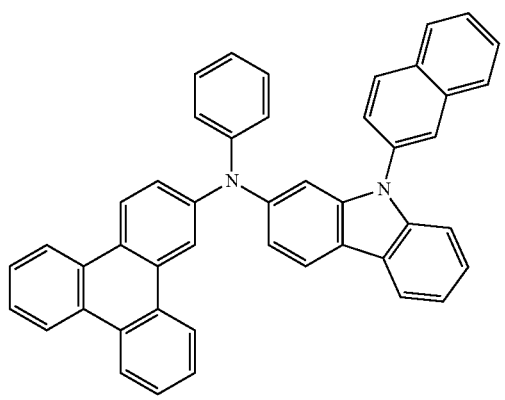

6
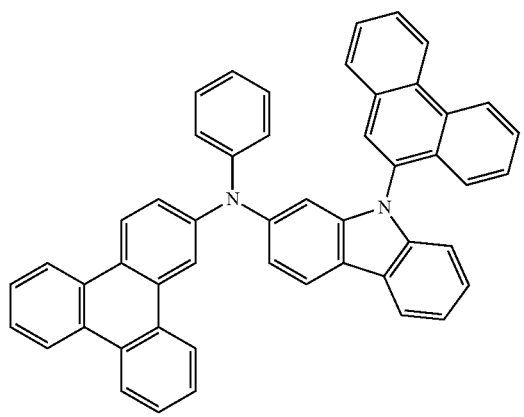
7
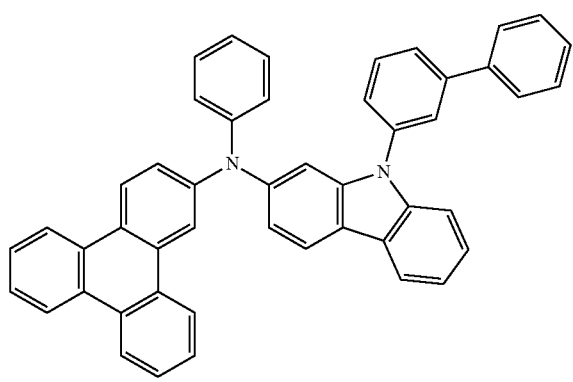
8
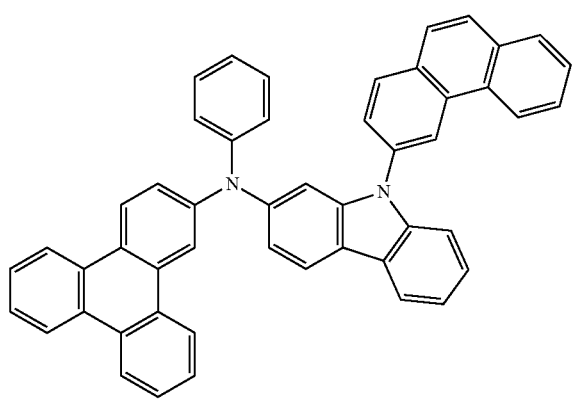
9
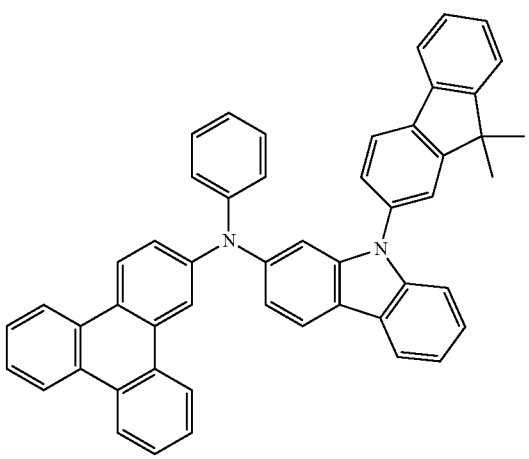
10
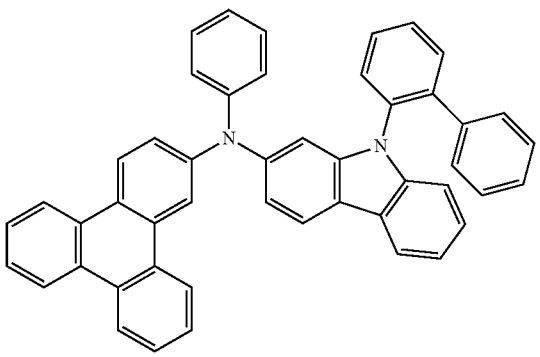
11
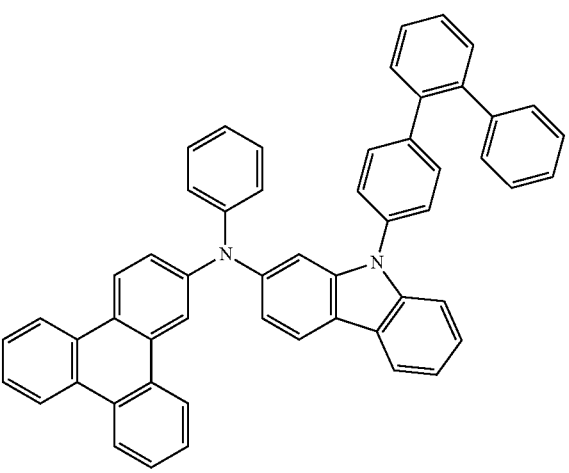

12
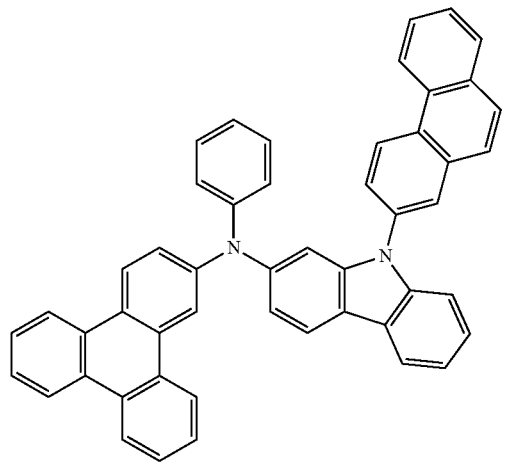
13
15
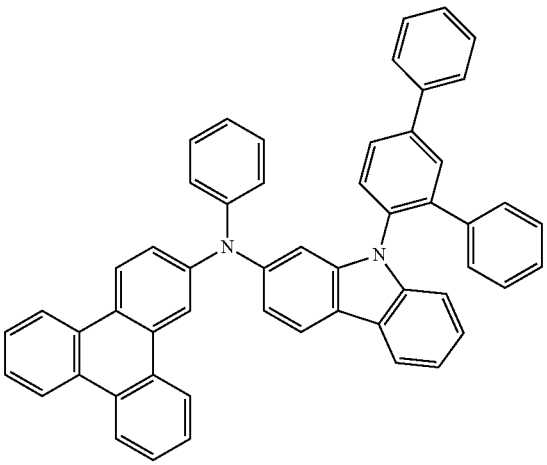
16
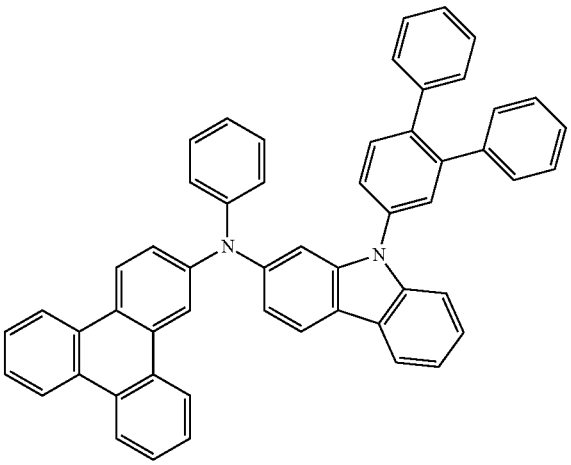
14
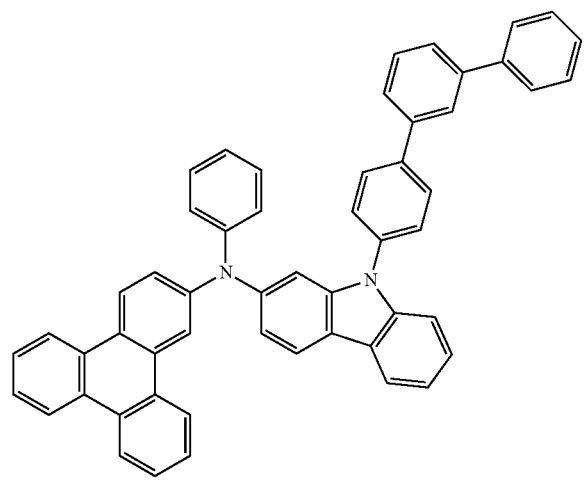
17

18
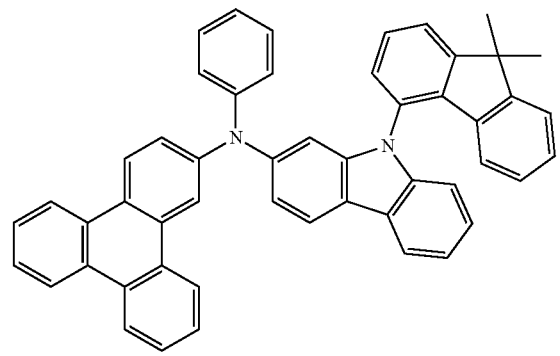
19
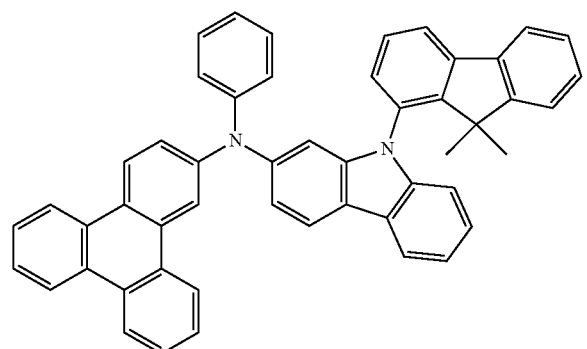
20
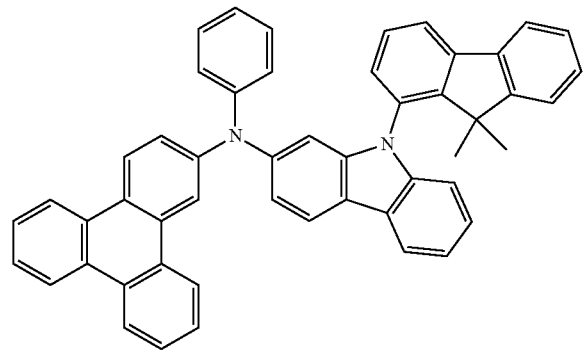
21
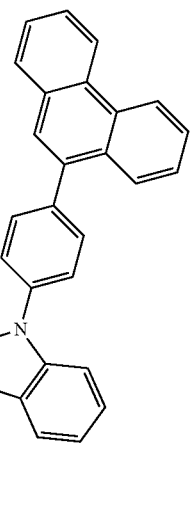
22
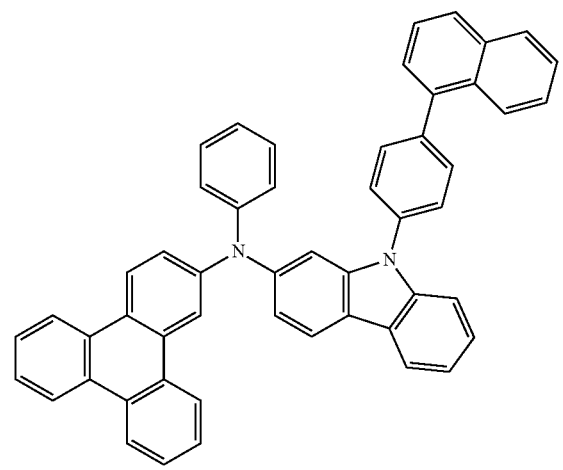
23
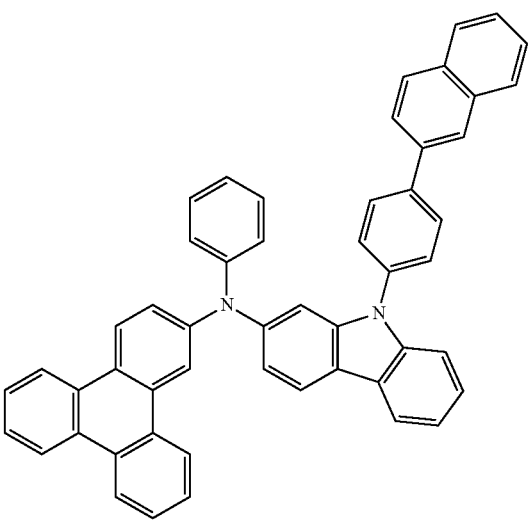

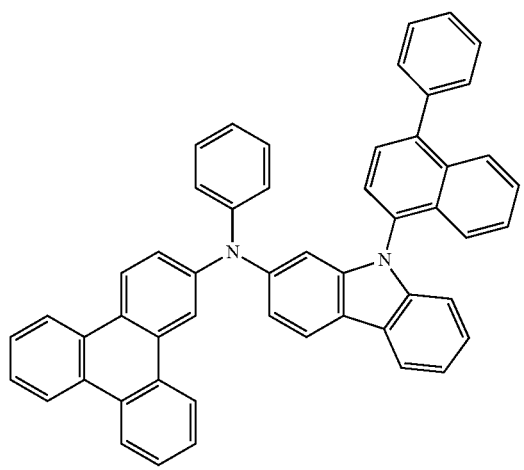
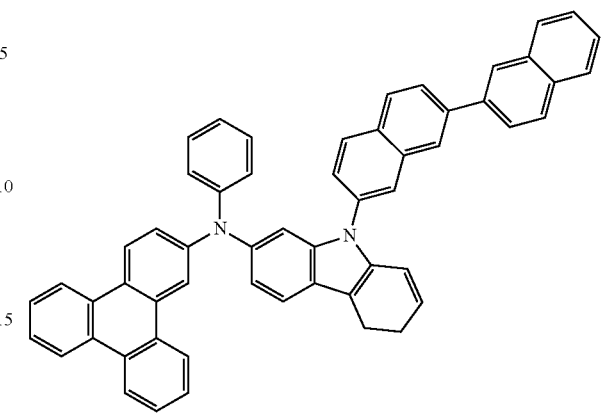
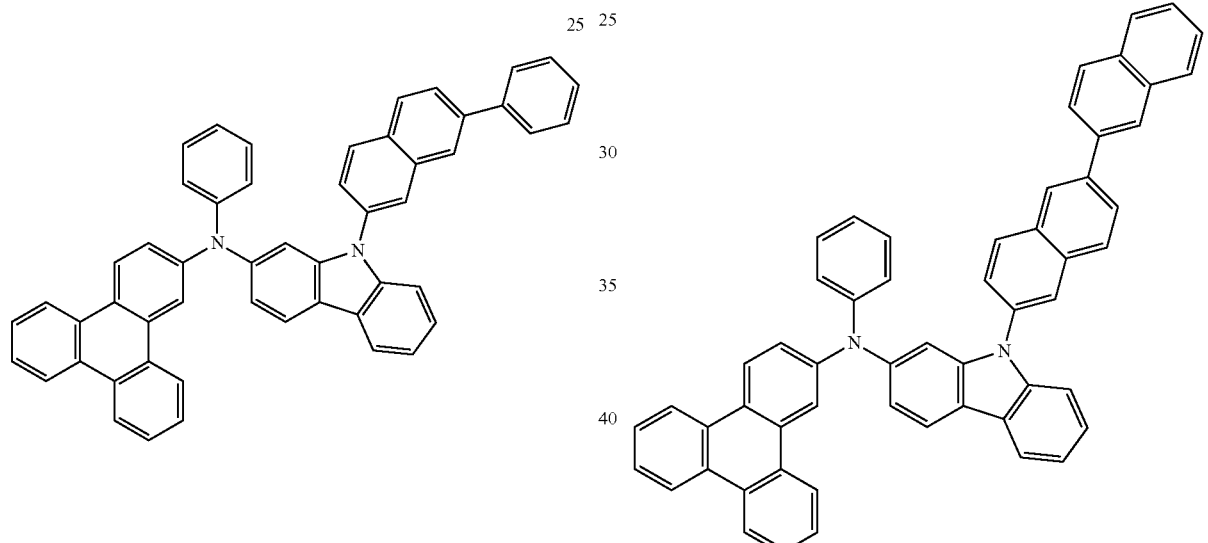
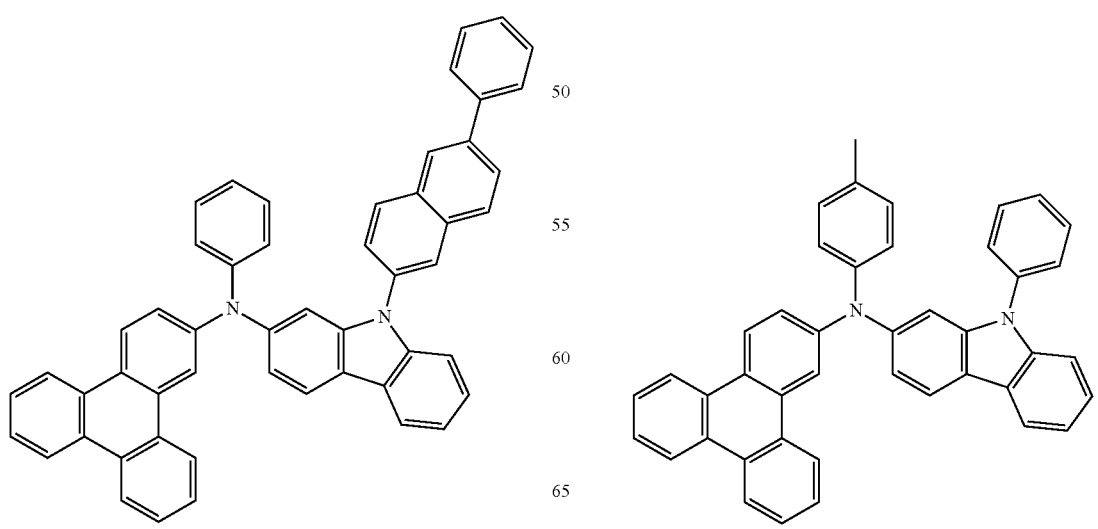

30
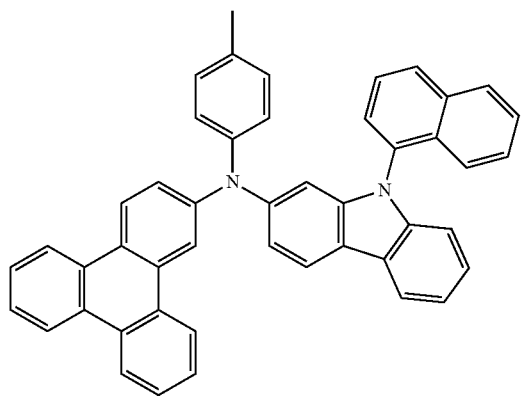
31
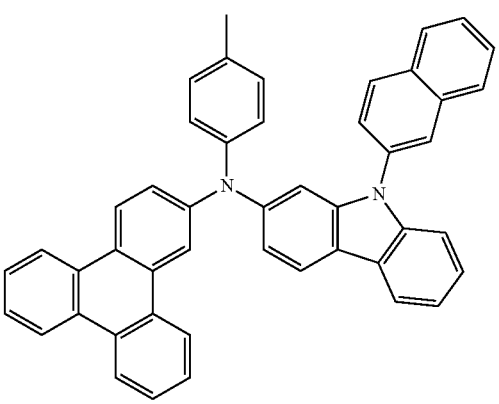
32
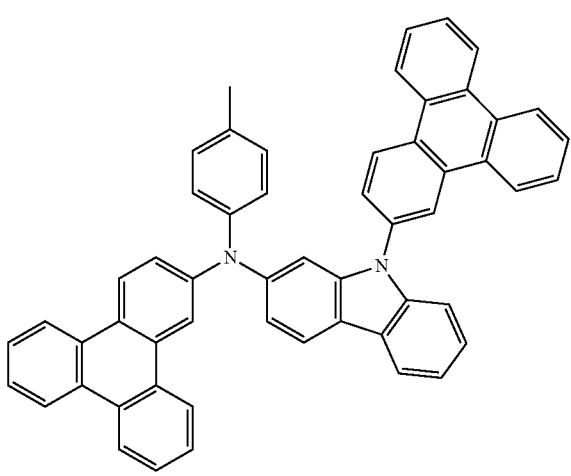
33
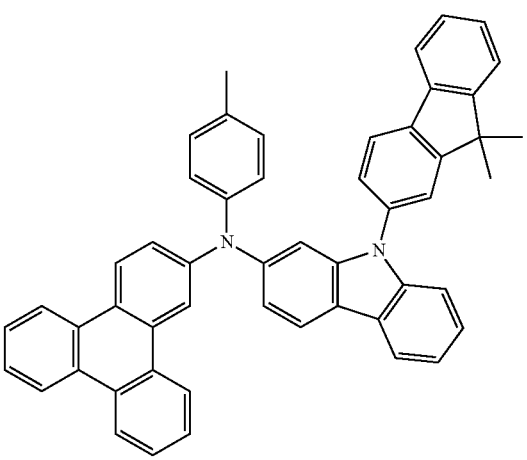
34
35
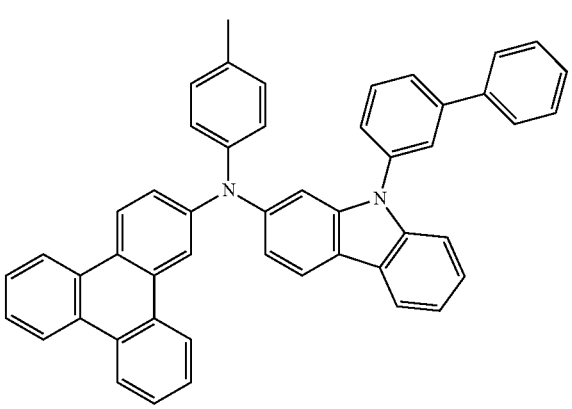

36
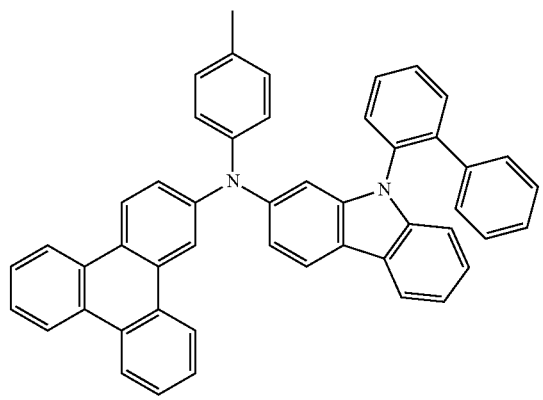
37
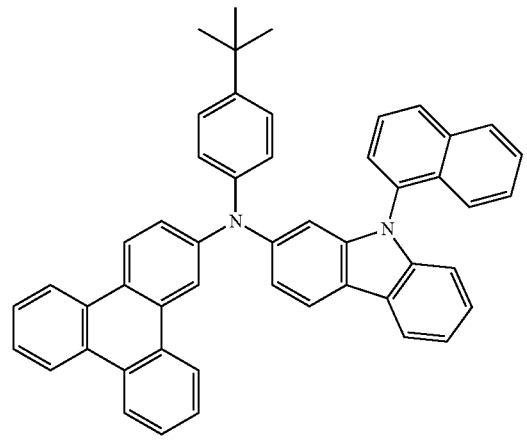
39
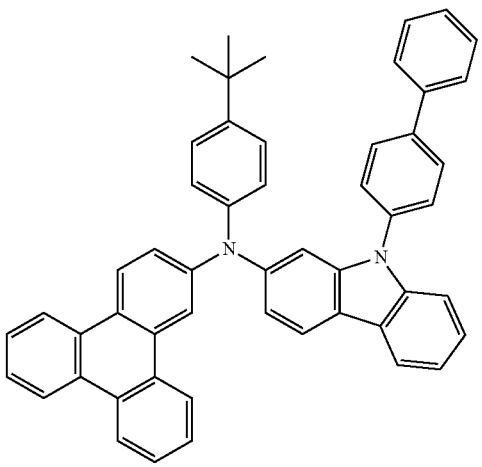
40
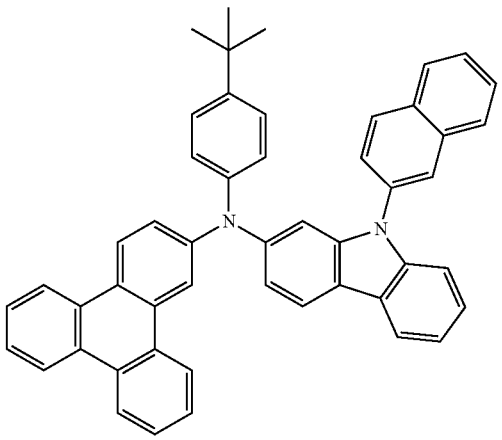

42
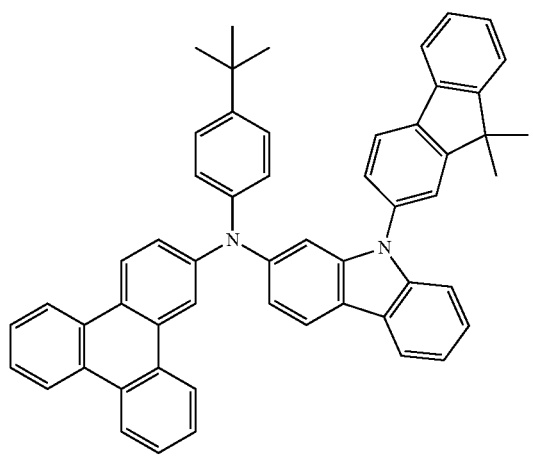
43
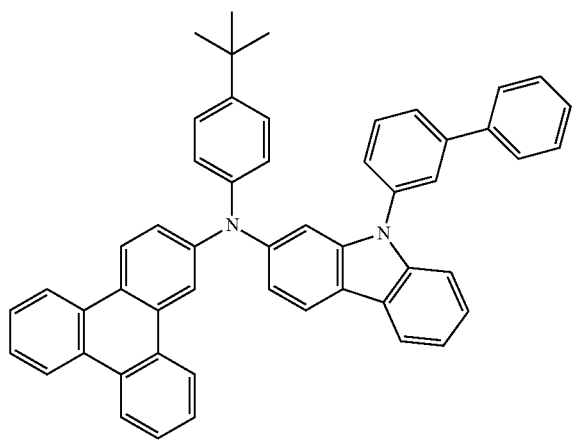
44
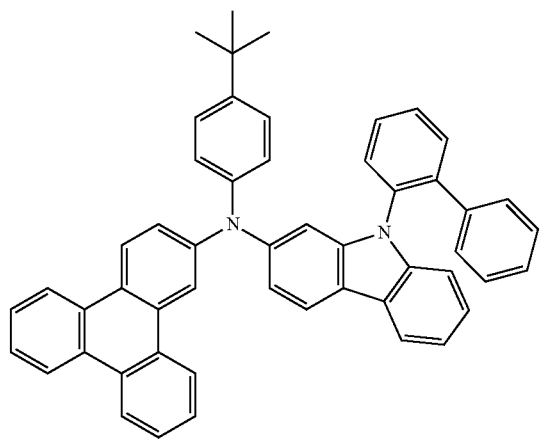
45
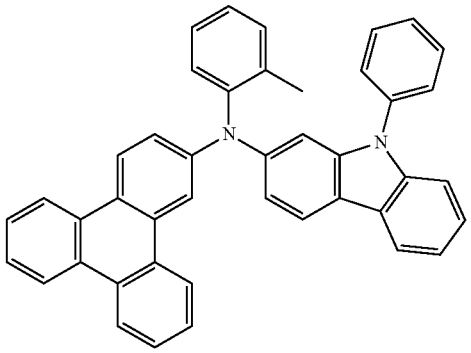
46
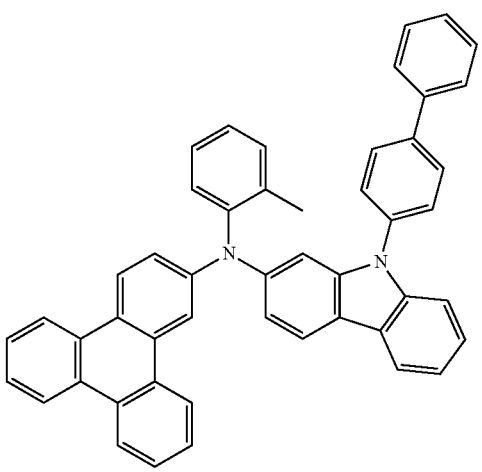
47

48
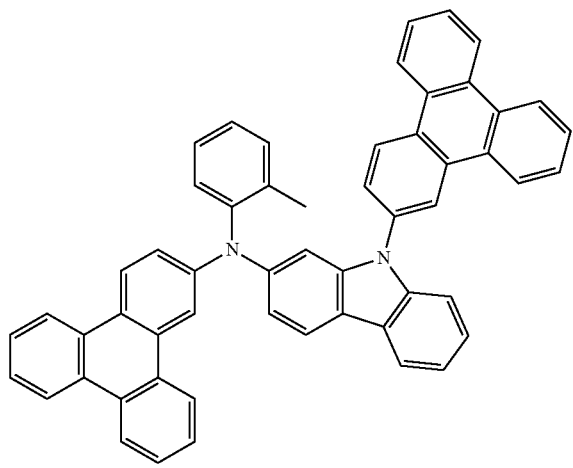
49
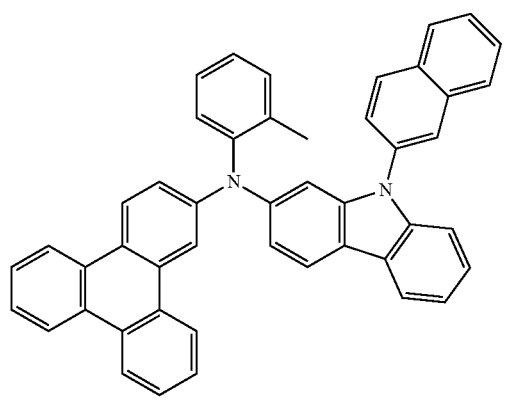
50
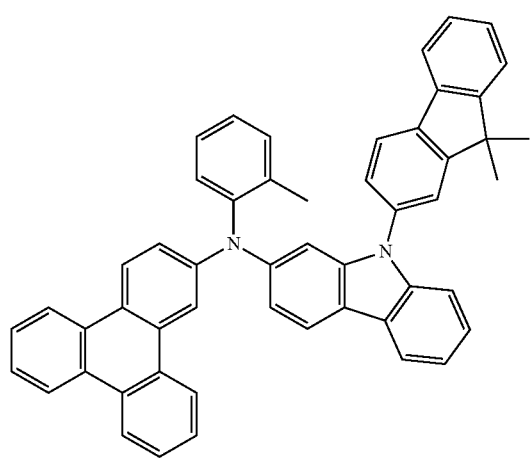
51
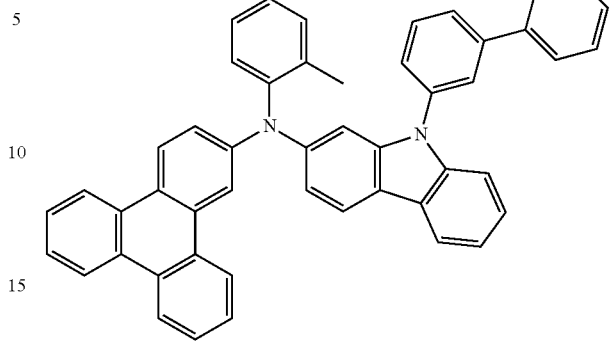
52
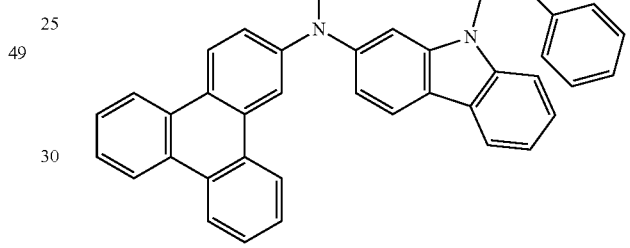
53
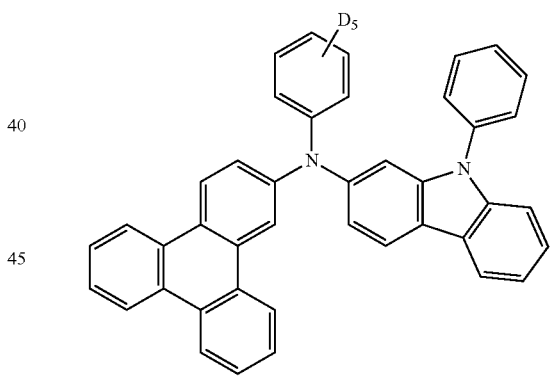
54
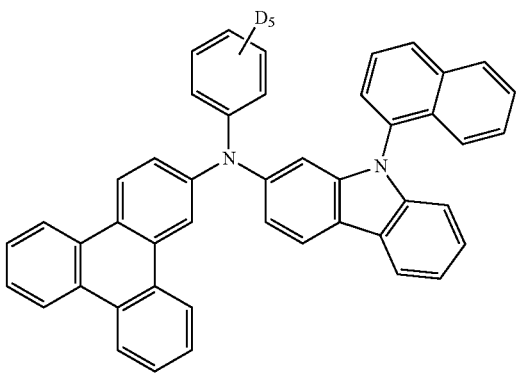

-continued
55
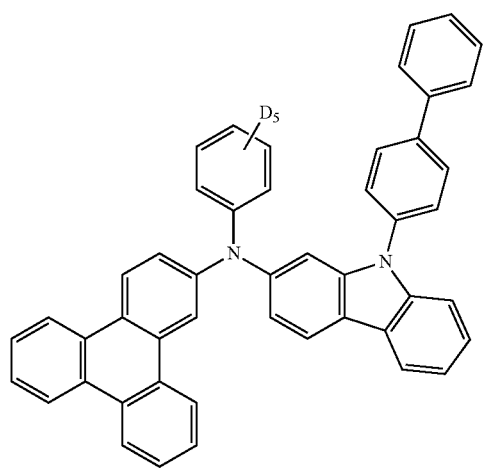
56
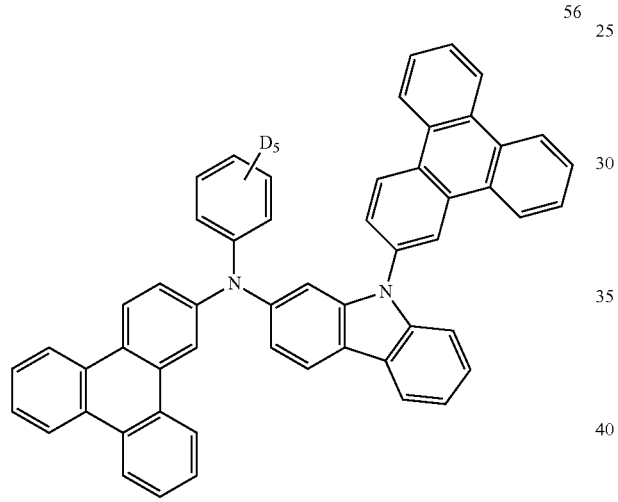
57
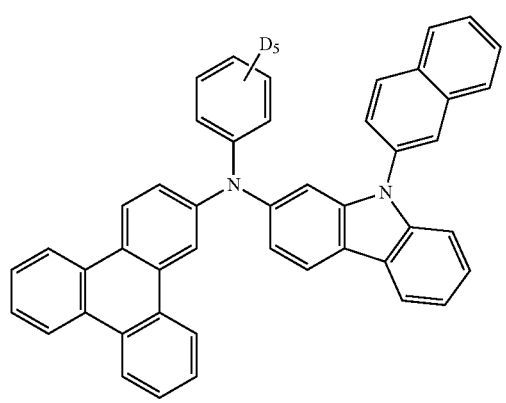
-continued
58
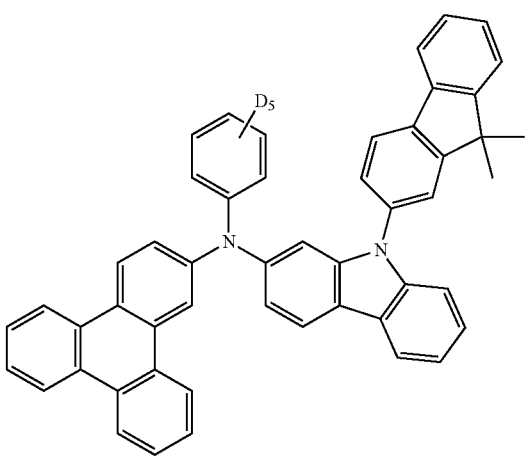
59
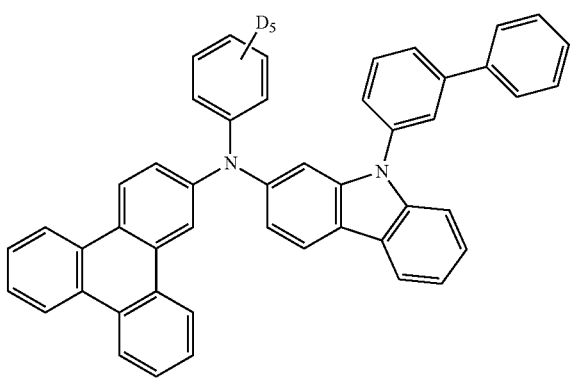
60
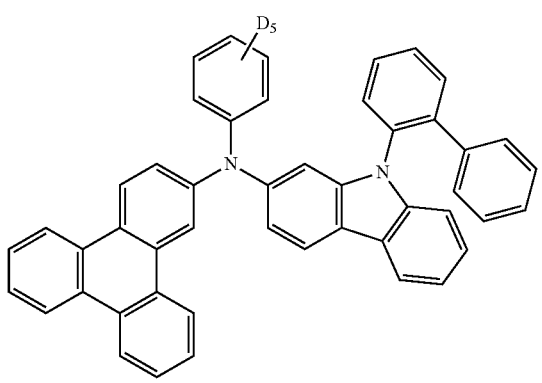

33
-continued
61
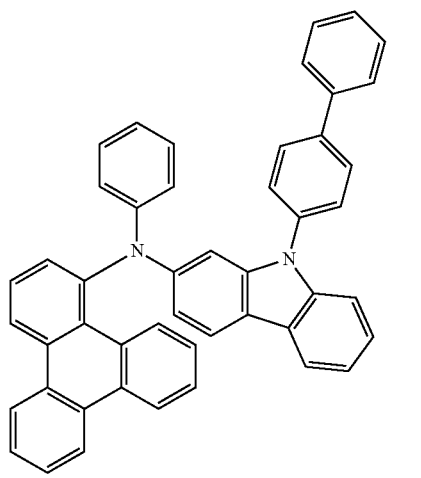
62
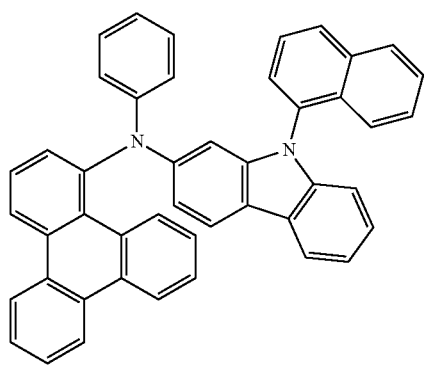
63
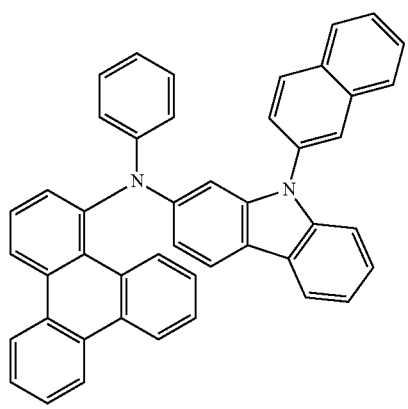
64
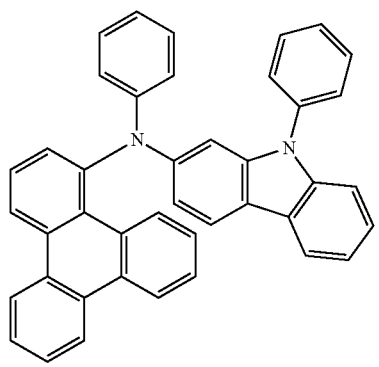
34
-continued
65
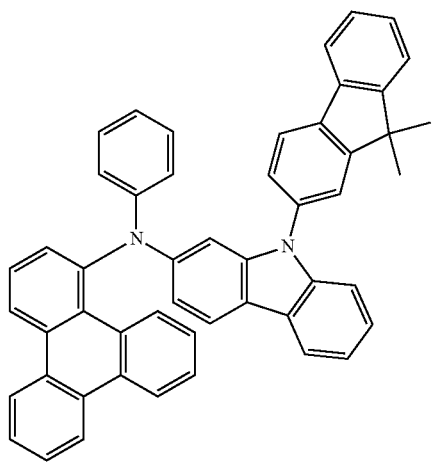
66
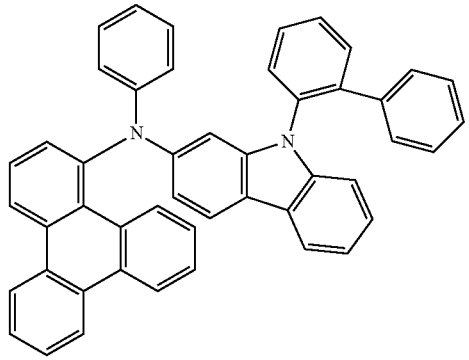
67
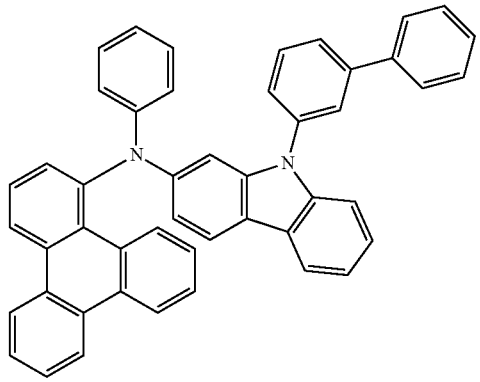
68
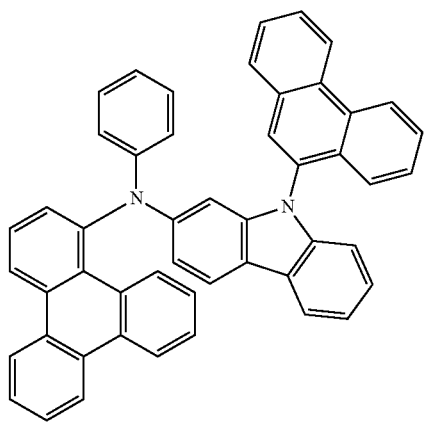

69
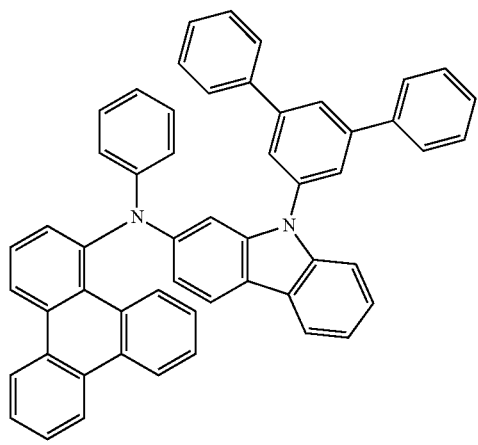
70
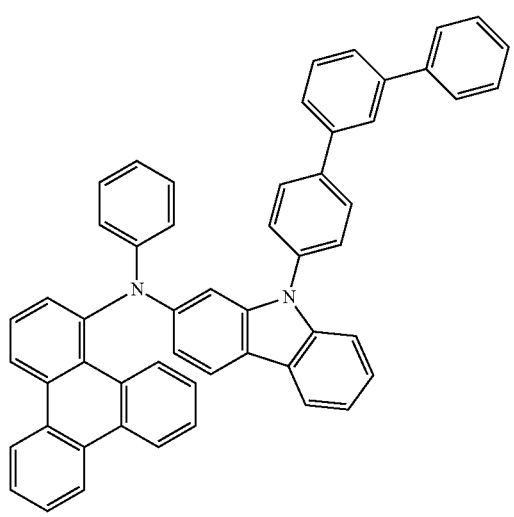
71
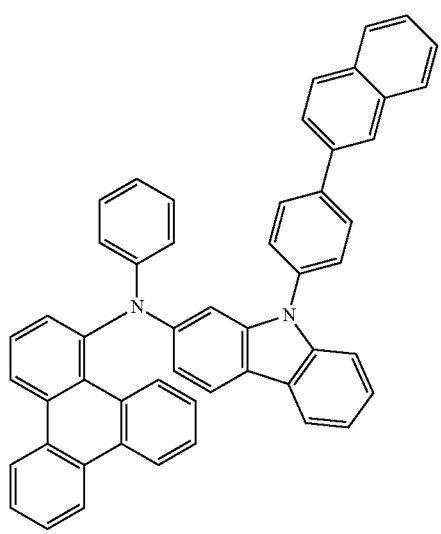
72
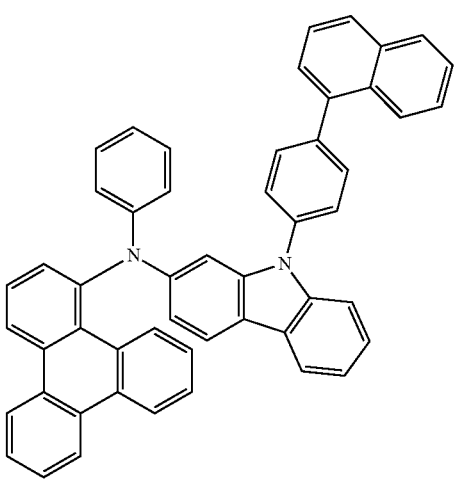
73
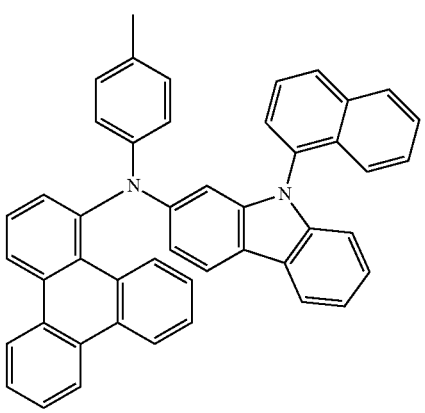
74
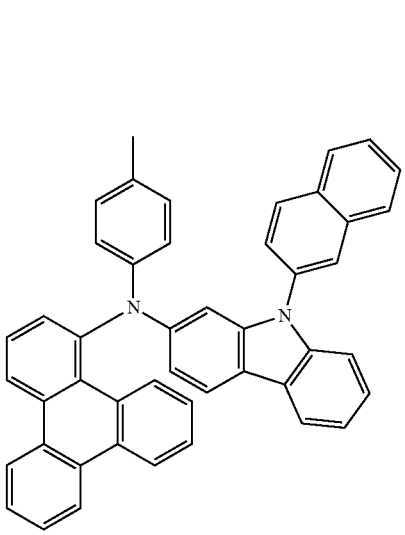

75
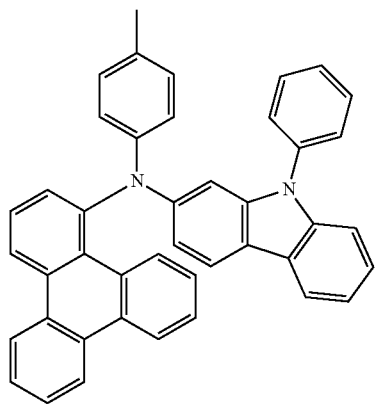
76
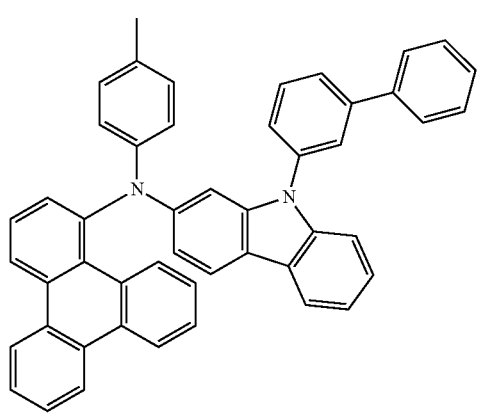
77
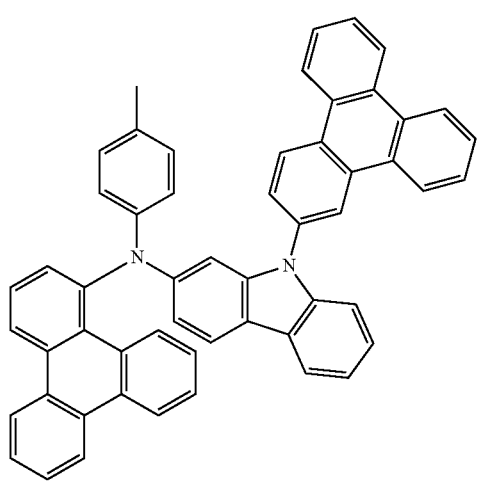
78
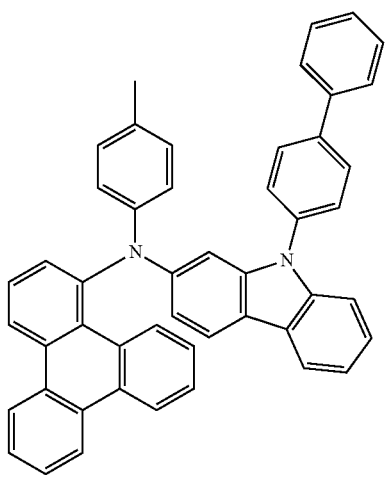
79
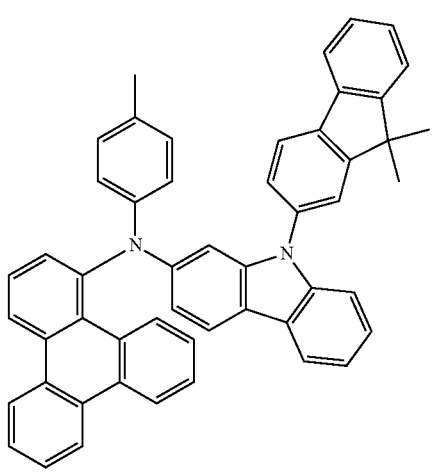
80
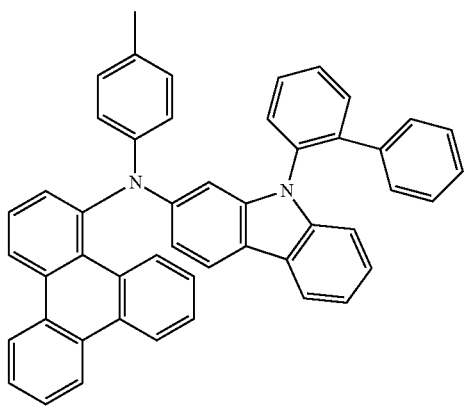

81
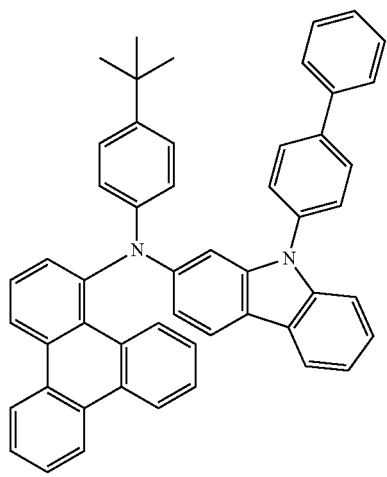
82
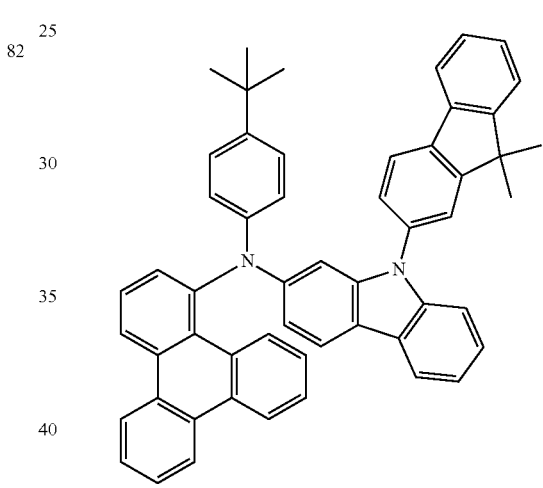
83
84
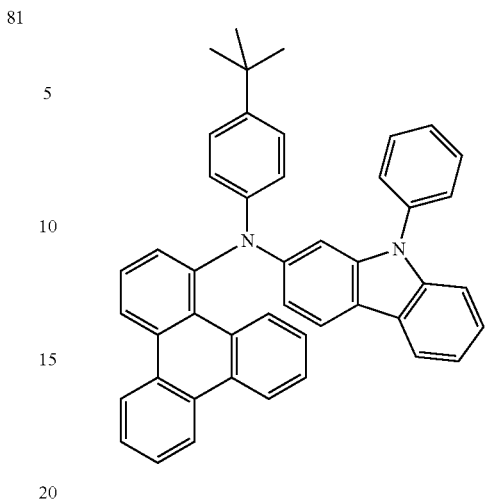
85
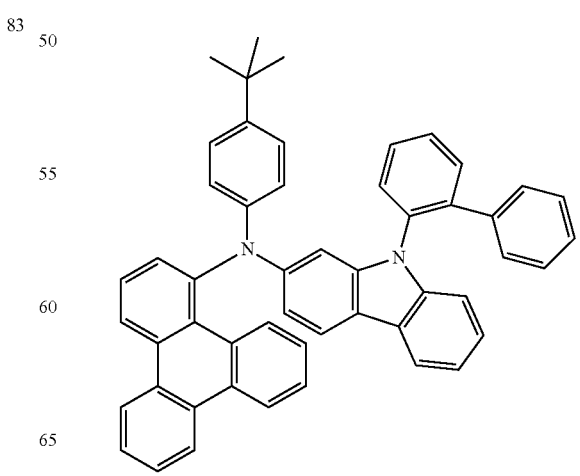
86

41
-continued
87
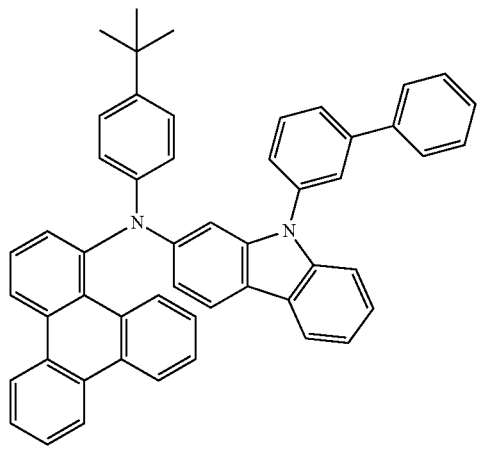
88
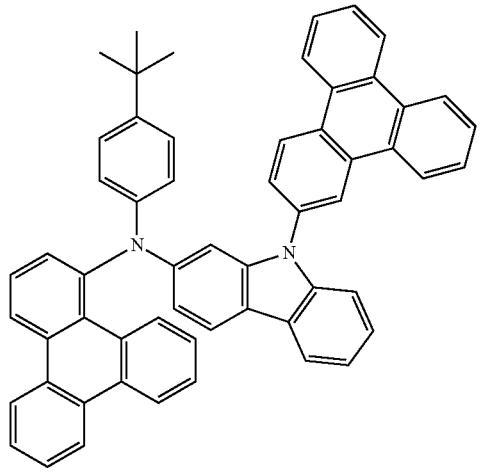
89
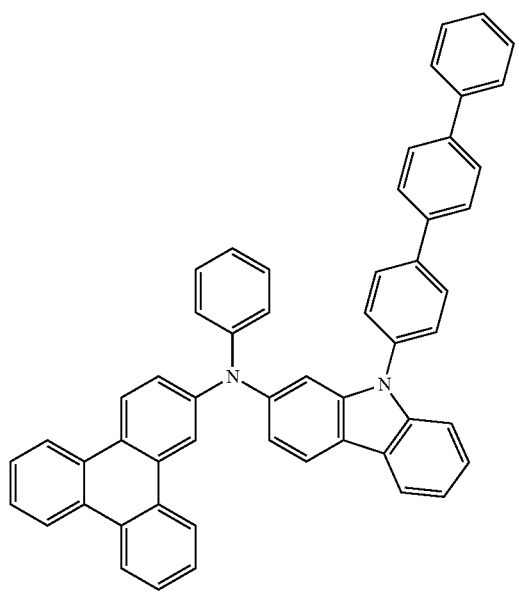
42
-continued
90
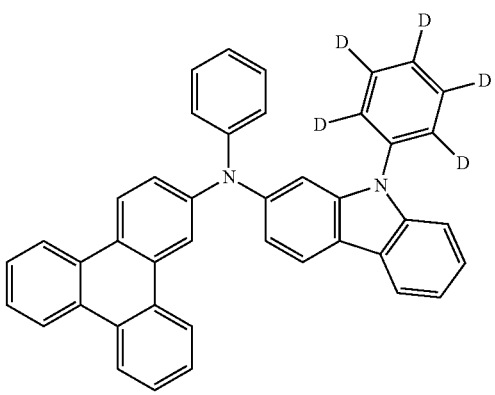
91
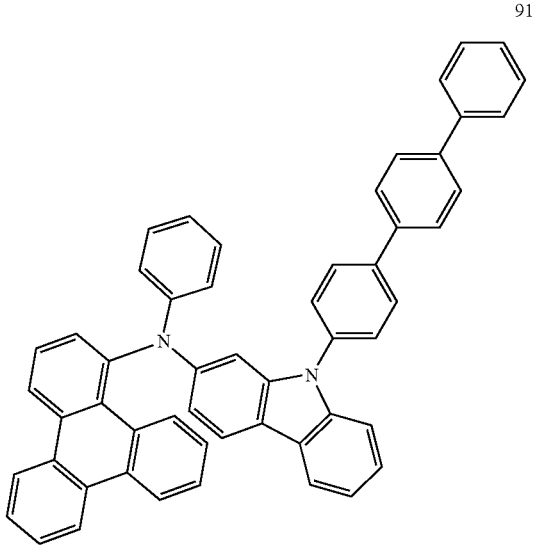
92
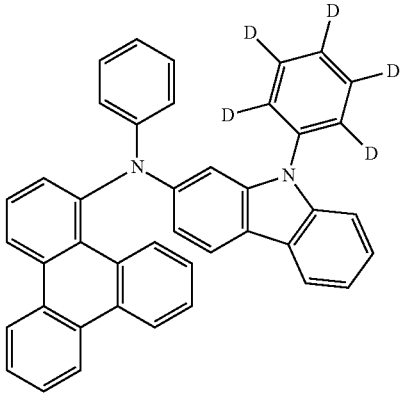

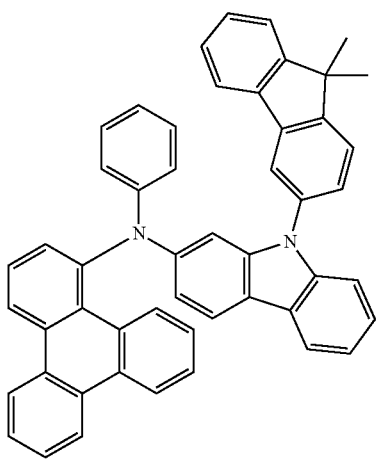
93
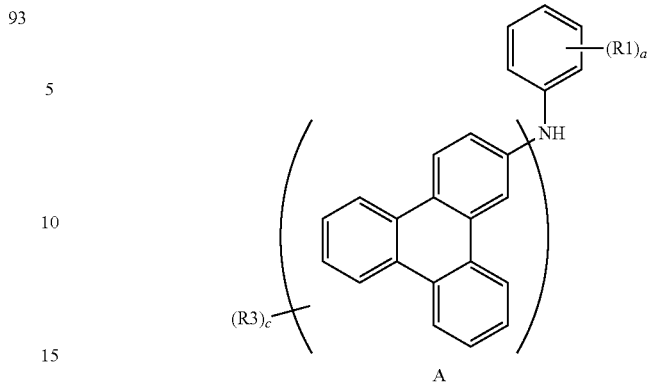
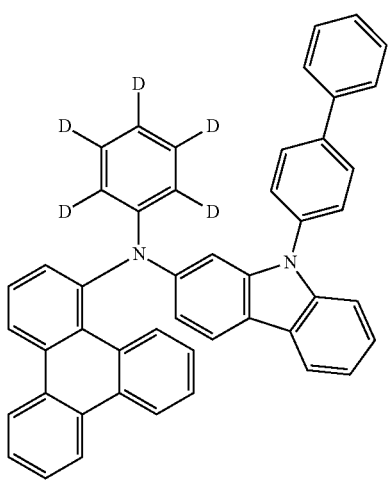
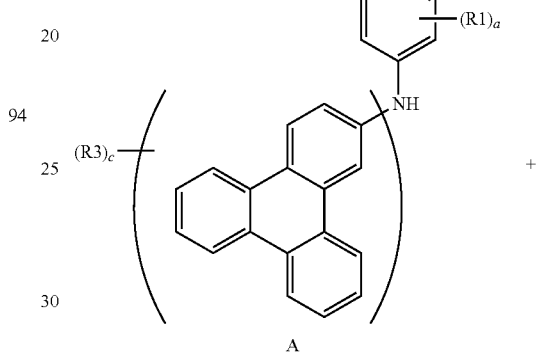
94
The compound of Chemical Formula 1 may be synthesized by a general reaction formula to be described below, but is not limited thereto.
<Reaction Formula A> Synthesis of Intermediate A
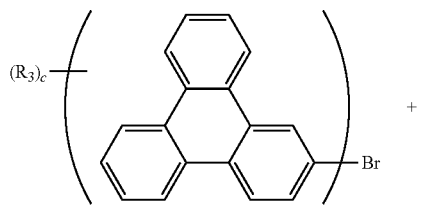
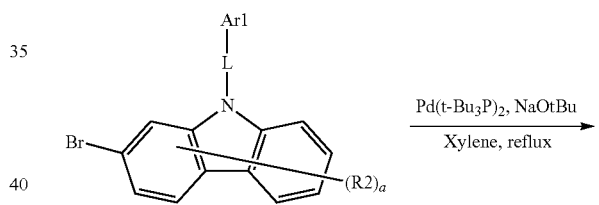
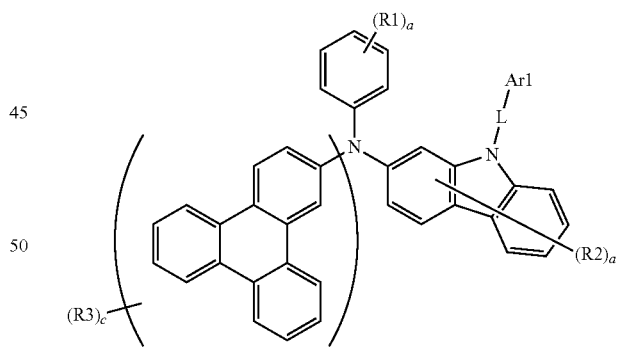
<Reaction Formula B> Synthesis of Intermediate B
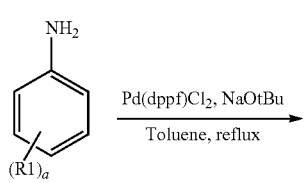
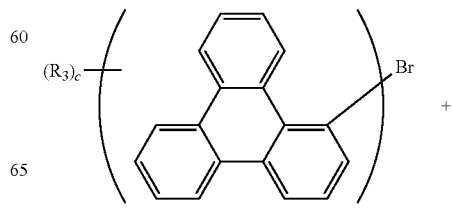

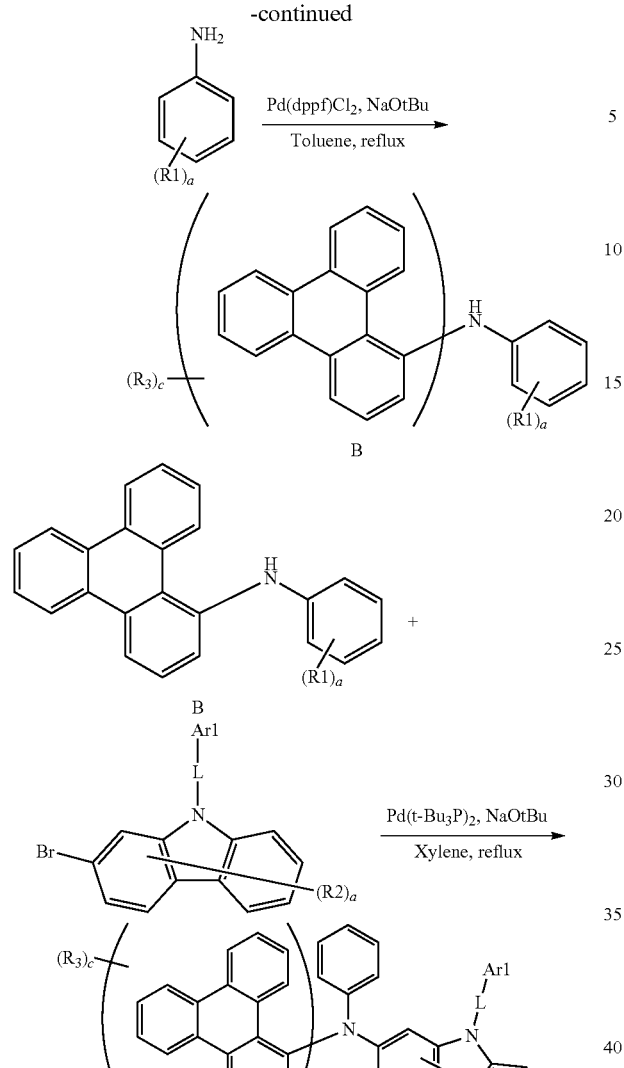
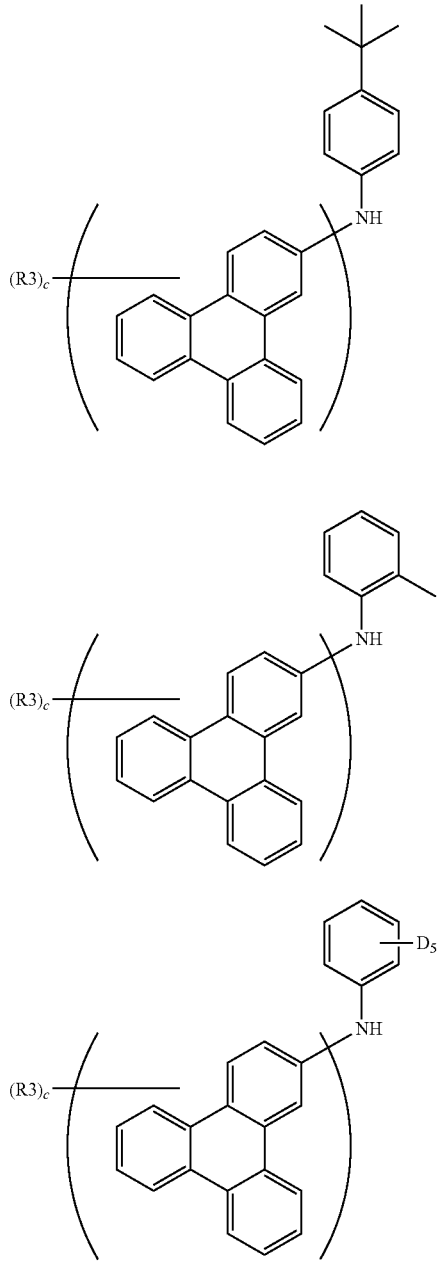
Further, the compound of Chemical Formula 1 may be synthesized by using the following C to J as an intermediate instead of Intermediate A or B in Reaction Formula A or B.
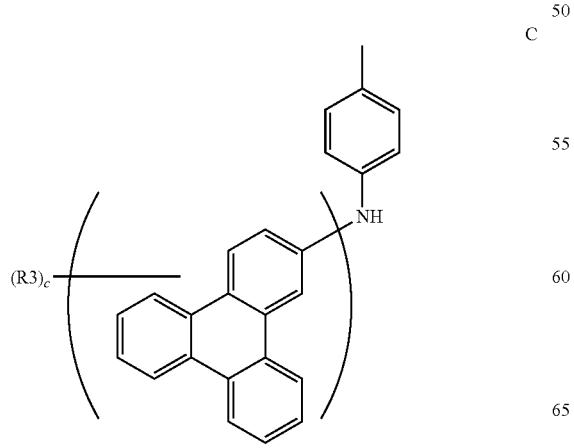
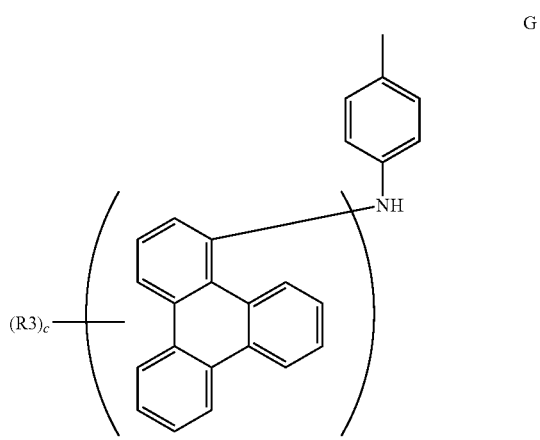

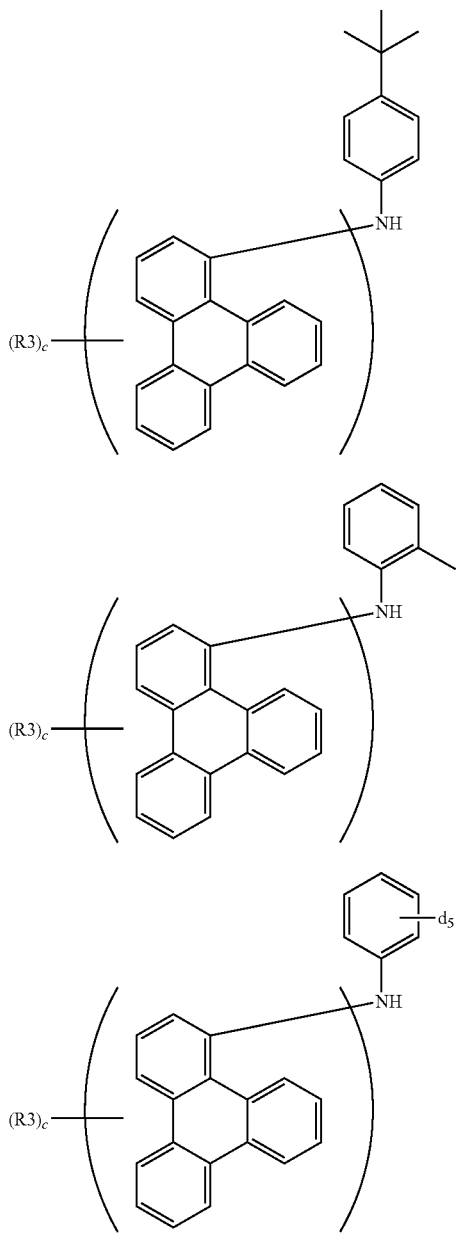

The conjugation length and energy bandgap of the compound are closely associated with each other. Specifically, the longer the conjugation length of the compound is, the smaller the bandgap is.

In the present invention, various substituents may be introduced into the positions of Ar1 and R1 having the core structure as described above to synthesize compounds having various energy bandgaps. A substituent is usually introduced into a core structure having a large energy bandgap to easily adjust the energy bandgap, but when the core structure has a small energy bandgap, it is difficult to significantly adjust the energy bandgap by introducing a substituent. Further, in the present invention, various substituents may also be introduced into the positions of Ar1 and R1 having the core structure as described above to adjust the HOMO and LUMO energy levels of a compound.

In addition, various substituents may be introduced into the core structure having the structure as described above to synthesize a compound having inherent characteristics of the introduced substituent. For example, a substituent usually used for a hole injection layer material, a material for transporting holes, a light emitting layer material, and an electron transport layer material, which are used for manufacturing an organic light emitting device, may be introduced into the core structure to synthesize a material which satisfies conditions required for each organic material layer.

Furthermore, an organic light emitting device according to the present invention is an organic light emitting device comprising a first electrode, a second electrode, and one or more organic material layers disposed between the first electrode and the second electrode, in which one or more layers of the organic material layers comprise the compound.

The organic light emitting device of the present invention may be manufactured by typical preparation methods and materials of an organic light emitting device, except that the above-described compound is used to form one or more organic material layers.

The compound may be formed as an organic material layer by not only a vacuum deposition method, but also a solution application method when an organic light emitting device is manufactured. Here, the solution application method means spin coating, dip coating, inkjet printing, screen printing, a spray method, roll coating, and the like, but is not limited thereto.

The organic material layer of the organic light emitting device of the present invention may also be composed of a single-layered structure, but may be composed of a multi-layered structure in which two or more organic material layers are stacked. For example, the organic light emitting device of the present invention may have a structure including a hole injection layer, an electron blocking layer, a hole transport layer, a light emitting layer, an electron transport layer, an electron injection layer, and the like as organic material layers. However, the structure of the organic light emitting device is not limited thereto, and may include a fewer number of organic material layers.

Accordingly, in the organic light emitting device of the present invention, the organic material layer may comprise one or more layers of a hole injection layer, an electron blocking layer, a hole transport layer, and a layer which injects and transports holes simultaneously, and one or more layers of the layers may comprise the compound represented by Chemical Formula 1.

In an exemplary embodiment, the organic material layer comprises an electron blocking layer, and the electron blocking layer comprises the compound represented by Chemical Formula 1.

In another exemplary embodiment, the organic material layer includes a hole transport layer, and the hole transport layer includes the compound represented by Chemical Formula 1.

In still another exemplary embodiment, the organic material layer comprises a light emitting layer, and the light emitting layer comprises the compound represented by Chemical Formula 1. As an example, the compound represented by Chemical Formula 1 may be included as a host of the light emitting layer. As another example, the compound represented by Chemical Formula 1 may be included as a phosphorescent host of the light emitting layer.

As still another example, the organic material layer comprising the compound represented by Chemical Formula 1 may comprise the compound represented by Chemical Formula 1 as a host, and may comprise another organic compound, metal or a metal compound as a dopant.

As yet another example, the organic material layer comprising the compound represented by Chemical Formula 1 may comprise the compound represented by Chemical Formula 1 as a host, and may use an iridium (Ir)-based dopant together.

Further, the organic material layer may comprise one or more layers of an electron transport layer, an electron injection layer, and a layer which transports and injects electrons simultaneously, and one or more layers of the layers may comprise the compound.

In another exemplary embodiment, the organic material layer of the organic electronic light emitting comprises a hole transport layer, and the hole transport layer comprises the compound represented by Chemical Formula 1.

In the organic material layer having the multi-layered structure, the compound may be included in a light emitting layer, a layer which injects holes/transports holes and emits light simultaneously, a layer which transports holes and emits light simultaneously, or a layer which transports electrons and emits light simultaneously, and the like.

In an exemplary embodiment of the present specification, the organic material layer comprises a light emitting layer, and the light emitting layer comprises a compound represented by the following Chemical Formula 6.

[Chemical Formula 6]

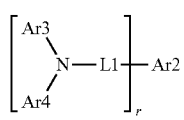

In Chemical Formula 6,

Ar2 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L1 is a direct bond; a substituted or unsubstituted arylene group; or a substituted or unsubstituted heteroarylene group, Ar3 and Ar4 are the same as or different from each other, and are each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or may combine with each other to form a substituted or unsubstituted ring, r is an integer of 1 or more, and when r is 2 or more, the substituents in the parenthesis are the same as or different from each other.

According to an exemplary embodiment of the present specification, the organic material layer comprises a light emitting layer, and the light emitting layer comprises the compound represented by Chemical Formula 6 as a dopant of the light emitting layer.

In an exemplary embodiment of the present specification, L1 is a direct bond.

According to an exemplary embodiment of the present specification, r is 2.

In an exemplary embodiment of the present specification, Ar2 is a substituted or unsubstituted divalent pyrene group.

In another exemplary embodiment, Ar2 is a divalent pyrene group which is unsubstituted or substituted with a methyl group, an ethyl group, a t-butyl group or an isopropyl group.

In still another exemplary embodiment, Ar2 is a divalent pyrene group.

In an exemplary embodiment of the present specification, Ar3 and Ar4 are the same as or different from each other, and are each independently a substituted or unsubstituted aryl group having 6 to 30 carbon atoms; a substituted or unsubstituted alkyl group having 1 to 30 carbon atoms; or a substituted or unsubstituted heteroaryl group having 2 to 30 carbon atoms.

According to an exemplary embodiment of the present specification, Ar3 and Ar4 are the same as or different from each other, and are each independently a substituted or unsubstituted aryl group having 6 to 30 carbon atoms.

According to an exemplary embodiment of the present specification, Ar3 and Ar4 are the same as or different from each other, and are each independently an aryl group having 6 to 30 carbon atoms, which is substituted or unsubstituted with a germanium group substituted with an alkyl group.

In an exemplary embodiment of the present specification, Ar3 and Ar4 are is a phenyl group which is unsubstituted or substituted with a trimethylgermanium group.

According to an exemplary embodiment of the present specification, Chemical Formula 6 may be represented by the following compound.

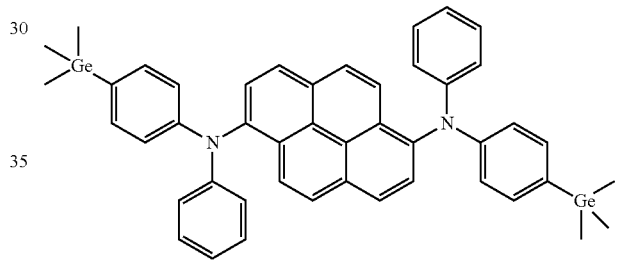

In an exemplary embodiment of the present specification, the organic material layer comprises a light emitting layer, and the light emitting layer comprises a compound represented by the following Chemical Formula 7.

[Chemical Formula 7]

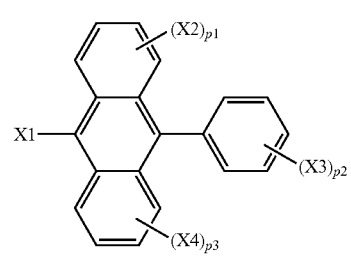

In Chemical Formula 7,

X1 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthalenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

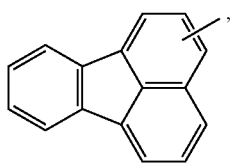

X3 is a phenyl group, a 1-naphtyl group, a 2-naphtyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, X2 and X4 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, p2 is an integer of 1 to 5, p1 and p3 are each an integer of 1 to 4, and when p1 to p3 are each 2 or more, the substituents in the parenthesis are the same as or different from each other.

According to an exemplary embodiment of the present specification, the organic material layer comprises a light emitting layer, and the light emitting layer comprises the compound represented by Chemical Formula 7 as a host of the light emitting layer.

In an exemplary embodiment of the present specification, X1 is a 1-naphthyl group.

In an exemplary embodiment of the present specification, X3 is a 2-naphthyl group, and p2 is 1.

In an exemplary embodiment of the present specification, X2 and X4 are hydrogen.

According to an exemplary embodiment of the present specification, Chemical Formula 7 may be represented by the following compound.

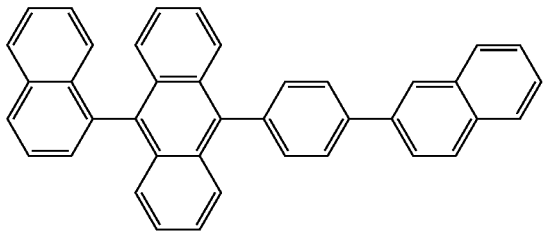 [SMILES: c1ccc2cc(-c3ccc(-c4c5ccccc5c(-c5cccc6ccccc56)c5ccccc45)cc3)ccc2c1]

For example, the structure of the organic light emitting device of the present invention may have a structure as illustrated in FIGS. 1 and 2, but is not limited thereto.

FIG. 1 illustrates the structure of an organic light emitting device in which a positive electrode (2), a light emitting layer (3), and a negative electrode (4) are sequentially stacked on a substrate (1). In the structure as described above, the compound may be included in the light emitting layer (3).

FIG. 2 illustrates the structure of an organic light emitting device in which a positive electrode (2), a hole injection layer (5), a hole transport layer (6), a light emitting layer (3), an electron transport layer (7), and a negative electrode (4) are sequentially stacked on a substrate (1). In the structure as described above, the compound may be included in the hole injection layer (5), the hole transport layer (6), the light emitting layer (3), or the electron transport layer (7).

For example, the organic light emitting device according to the present invention may be manufactured by depositing a metal or a metal oxide having conductivity, or an alloy thereof on a substrate to form a positive electrode, forming an organic material layer including a hole injection layer, a hole transport layer, a light emitting layer, and an electron transport layer thereon, and then depositing a material, which may be used as a negative electrode, thereon, by using a physical vapor deposition (PVD) method such as sputtering or e-beam evaporation. In addition to the method as described above, an organic light emitting device may also be made by sequentially depositing a negative electrode material, an organic material layer, and a positive electrode material on a substrate.

The organic material layer may have a multi-layered structure comprising a hole injection layer, a hole transport layer, a light emitting layer, and an electron transport layer, and the like, but is not limited thereto and may have a single-layered structure. Further, the organic material layer may be manufactured with a fewer number of layers by a method such as a solvent process, for example, spin coating, dip coating, doctor blading, a screen printing, inkjet printing, or a thermal transfer method using various polymers, instead of a deposition method.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methyl compound), poly[3,4-(ethylene-1,2-dioxy)compound] (PEDT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, hut are not limited thereto.

The hole injection material is a material which may receive well holes injected from the positive electrode at low voltage, and it is preferred that the highest occupied molecular orbital (HOMO) of the hole injection material is between the work function of the positive electrode material and the HOMO of the peripheral organic material layer. Specific examples of the hole injection material include metal porphyrin, oligothiophene, an arylamine-based organic material, a hexanitrile hexaazatriphenylene-based organic material, a quinacridone-based organic material, a perylenebased organic material, anthraquinone, a polyaniline and polycompound-based electrically conductive polymer, and the like, but are not limited thereto.

The hole transport material is a material which may receive holes transported from a positive electrode or a hole injection layer and transfer the holes to a light emitting layer, and is suitably a material having a large mobility for holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The organic material layer comprising the compound represented by Chemical Formula 1 may comprise the compound represented by Chemical Formula 1 as a host, and may use an iridium (IR)-based dopant together.

The iridium-based complex used as a dopant is as follows.

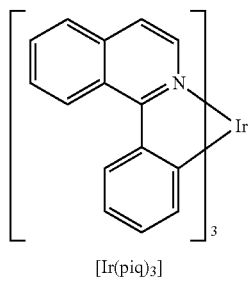

[Ir(piq)$_3$]

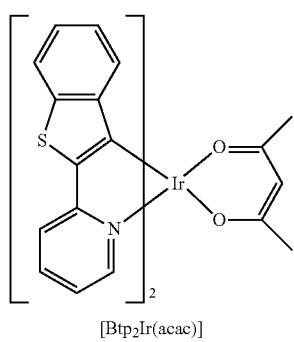

[Btp$_2$Ir(acac)]

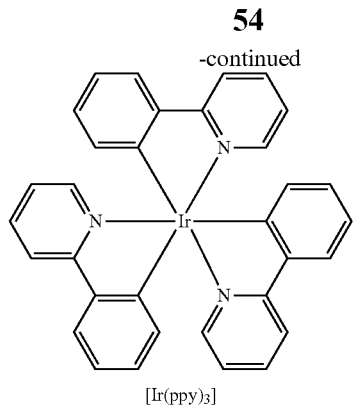

[Ir(ppy)$_3$]

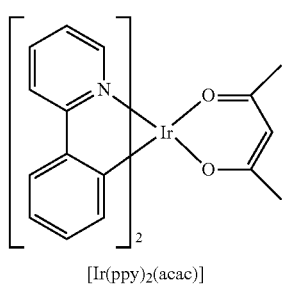

[Ir(ppy)$_2$(acac)]

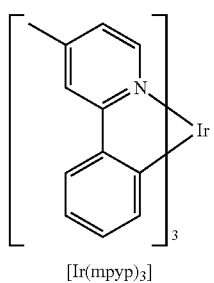

[Ir(mpyp)$_3$]

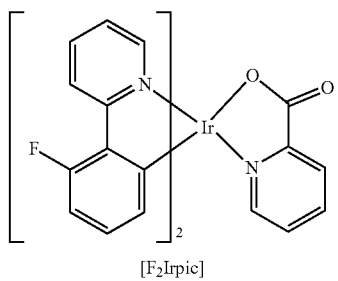

[F$_2$Irpic]

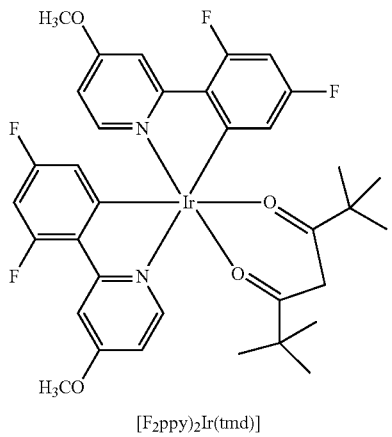

[F$_2$ppy)$_2$Ir(tmd)]

-continued

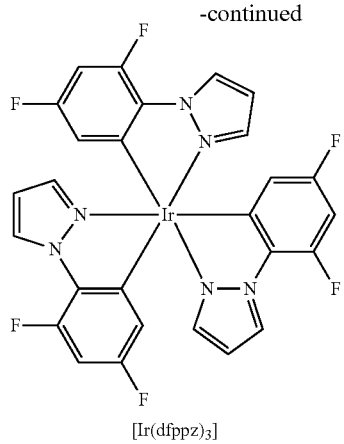

[Ir(dfppz)₃]

The electron transport material is a material which may receive well electrons injected from a negative electrode and transfer the electrons to a light emitting layer, and is suitably a material having a large mobility for electrons. Specific examples thereof include: an Al complex of 8-hydroxyquinoline; a complex including Alq₃; an organic radical compound; a hydroxyflavone-metal complex, and the like, but are not limited thereto.

The organic light emitting device according to the present invention may be a top emission type, a bottom emission type, or a dual emission type according to the material to be used.

The compound according to the present invention may be operated by a principle which is similar to the principle applied to an organic light emitting device, even in an organic electronic device including an organic solar cell, an organic photoconductor, an organic transistor, and the like.

The preparation method of the compound of Chemical Formula 1 and the manufacture of an organic light emitting device using the same will be specifically described in the following Examples. However, the following Examples are provided for exemplifying the present invention, and the scope of the present invention is not limited thereby.

Preparation Example 1

Synthesis of Compound 1

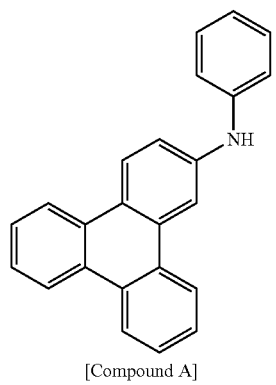

[Compound A]

+

-continued

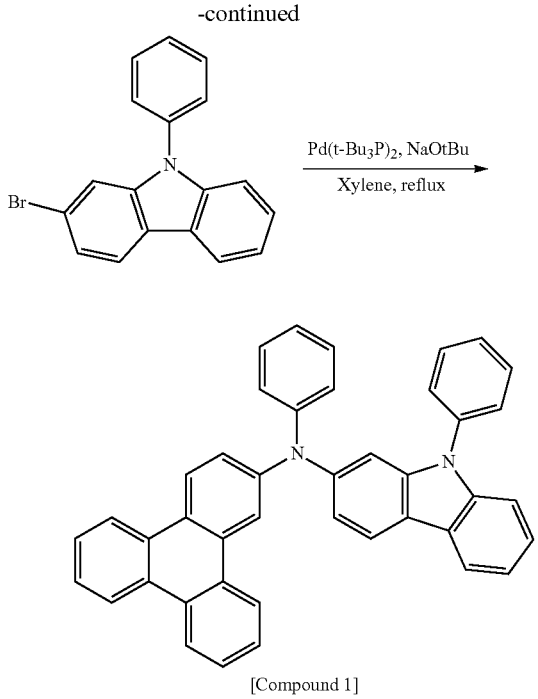

[Compound 1]

Compound A (12.0 g, 37.62 mmol) and 2-bromo-9-phenyl-9H-carbazole (10.98 g, 34.21 mmol) were completely dissolved in 240 ml of xylene in a 500 ml round bottom flask under nitrogen atmosphere, and then sodium tert-butoxide (4.27 g, 44.46 mmol) was added thereto, bis(tri-tert-butylphosphine) palladium (0) (0.17 g, 0.34 mmol) was put thereinto, and then the resulting mixture was heated and stirred for 2 hours. The temperature of the mixture was lowered to room temperature, the resulting mixture was filtered to remove the salt, and then xylene was concentrated under reduced pressure, and the residue was purified by column chromatography at a ratio of tetrahydrofuran:hexane=1:12 to prepare Compound 1 (16.54 g, yield: 78%).

MS[M+H]+=561

Preparation Example 2

Synthesis of Compound 3

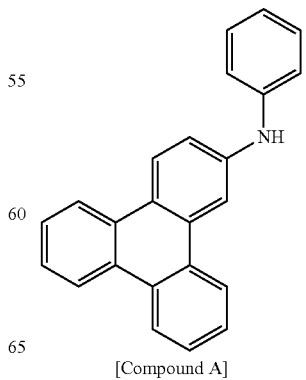

[Compound A]

+

-continued

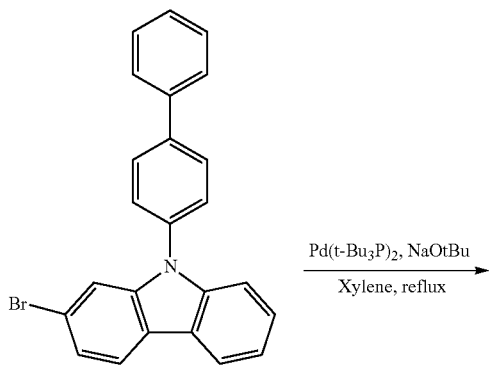

Preparation Example 3

Synthesis of Compound 9

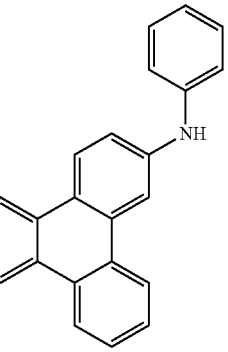

[Compound A]

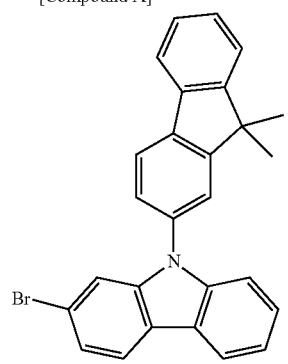

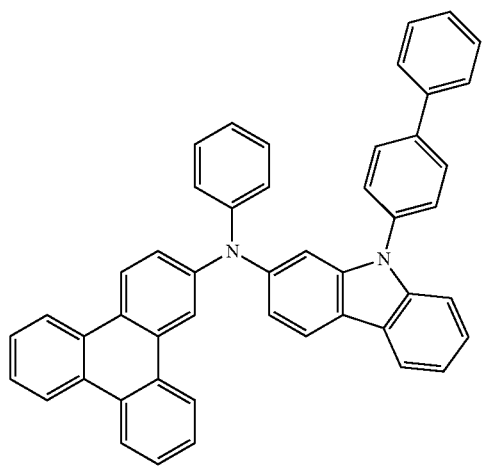

[Compound 3]

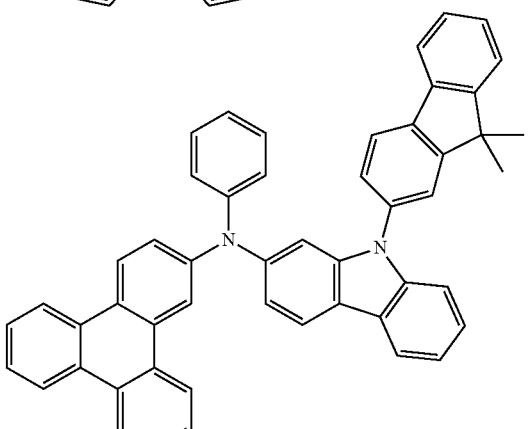

[Compound 9]

Compound A (12.0 g, 37.62 mmol) and 9-([1,1'-biphenyl]-4-yl)-2-bromo-9H-carbazole (13.38 g, 34.21 mmol) were completely dissolved in 280 ml of xylene in a 500 ml round bottom flask under nitrogen atmosphere, and then sodium tert-butoxide (4.27 g, 44.46 mol) was added thereto, bis(tri-tert-butylphosphine) palladium(0) (0.17 g, 0.34 mmol) was put thereinto, and then the resulting mixture was heated and stirred for 4 hours. The temperature of the mixture was lowered to room temperature, the resulting mixture was filtered to remove the salt, and then xylene was concentrated under reduced pressure, and the residue was recrystallized with 300 ml of ethyl acetate to prepare Compound 3 (21.33 g, yield: 89%).

MS [M+H]+=637

Compound A (12.0 g, 37.62 mmol) and 2-bromo-9-(9,9-dimethyl-9H-fluoren-2-yl)-9H-carbazole (14.95 g, 34.21 mmol) were completely dissolved in 240 ml of xylene in a 500 ml round bottom flask under nitrogen atmosphere, and then sodium tert-butoxide (4.27 g, 44.46 mol) was added thereto, bis(tri-tert-butylphosphine) palladium(0) (0.17 g, 0.34 mmol) was put thereinto, and then the resulting mixture was heated and stirred for 2 hours. The temperature of the mixture was lowered to room temperature, the resulting mixture was filtered to remove the salt, and then xylene was concentrated under reduced pressure, and the residue was purified by column chromatography at a ratio of tetrahydrofuran:hexane=1:16 to prepare Compound 9 (19.77 g, yield: 77%).

MS[M+H]+=677

Preparation Example 4

Synthesis of Compound 5

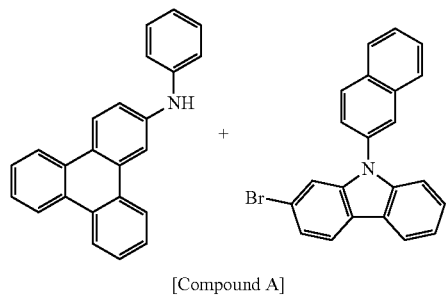

[Compound A]

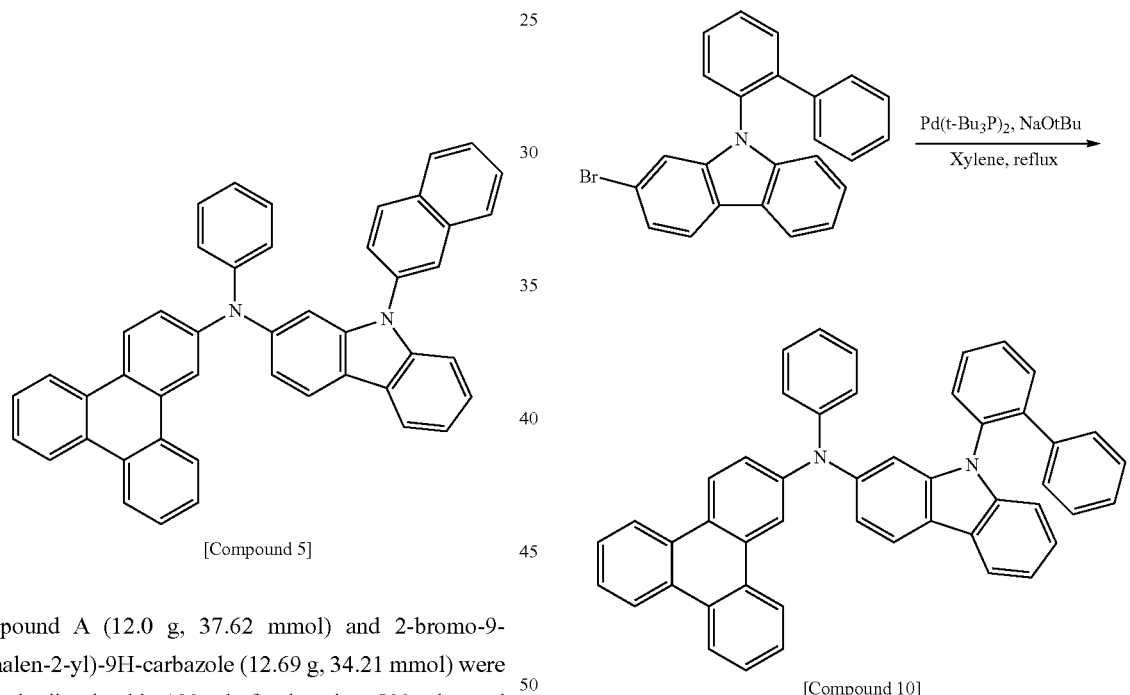

[Compound 5]

Compound A (12.0 g, 37.62 mmol) and 2-bromo-9-(naphthalen-2-yl)-9H-carbazole (12.69 g, 34.21 mmol) were completely dissolved in 180 ml of xylene in a 500 ml round bottom flask under nitrogen atmosphere, and then sodium tert-butoxide (4.27 q, 44.46 mol) was added thereto, bis(tri-tert-butylphosphine) palladium(0) (0.17 g, 0.34 mmol) was put thereinto, and then the resulting mixture was heated and stirred for 2 hours. The temperature of the mixture was lowered to room temperature, the resulting mixture was filtered to remove the salt, and then xylene was concentrated under reduced pressure, and the residue was purified by column chromatography at a ratio of tetrahydrofuran:hexane=1:16 to prepare Compound 5 (16.92 g, yield: 74%).

MS[M+H]+=611

Preparation Example 5

Synthesis of Compound 10

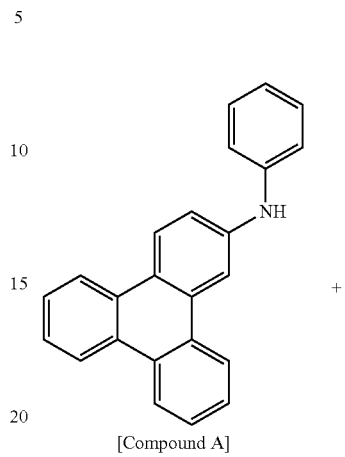

[Compound A]

[Compound 10]

Compound A (12.0 g, 37.62 mmol) and 9-([1,1'-biphenyl]-2-yl)-2-bromo-9H-carbazole (13.58 g, 34.21 mmol) were completely dissolved in 280 ml of xylene in a 500 ml round bottom flask under nitrogen atmosphere, and then sodium tert-butoxide (4.27 g, 44.46 mol) was added thereto, bis(tri-tert-butylphosphine) palladium(0) (0.17 g, 0.34 mmol) was put thereinto, and then the resulting mixture was heated and stirred for 4 hours. The temperature of the mixture was lowered to room temperature, the resulting mixture was filtered to remove the salt, and then xylene was concentrated under reduced pressure, and the residue was recrystallized with 220 ml of ethyl acetate to prepare Compound 10 (17.07 g, yield: 71%).

MS[M+H]+=637

Preparation Example 6

Synthesis of Compound 89

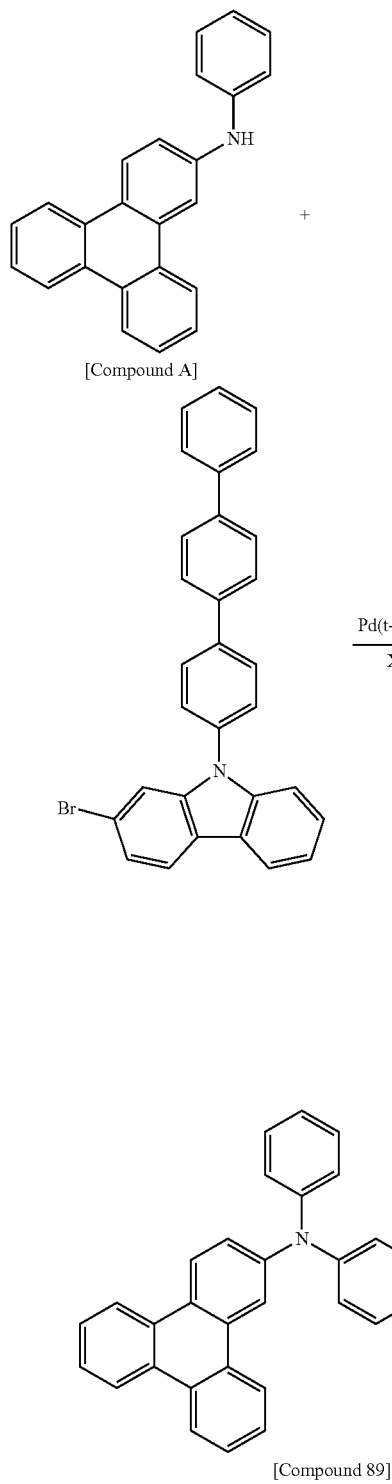

Compound A (12.0 g, 37.62 mmol) and 9-([1,1':4',1"-terphenyl]-4-yl)-2-bromo-9H-carbazole (16.18 g, 34.21 mmol) were completely dissolved in 240 ml of xylene in a 500 ml round bottom flask under nitrogen atmosphere, and then sodium tert-butoxide (4.27 g, 44.46 mol) was added thereto, bis(tri-tert-butylphosphine) palladium(0) (0.17 g, 0.34 mmol) was put thereinto, and then the resulting mixture was heated and stirred for 2 hours. The temperature of the mixture was lowered to room temperature, the resulting mixture was filtered to remove the salt, and then xylene was concentrated under reduced pressure, and the residue was purified by column chromatography at a ratio of tetrahydrofuran:hexane=1:12 to prepare Compound 89 (23.08 g, yield: 86%).

MS[M+H]+=713

Preparation Example 7

Synthesis of Compound 7

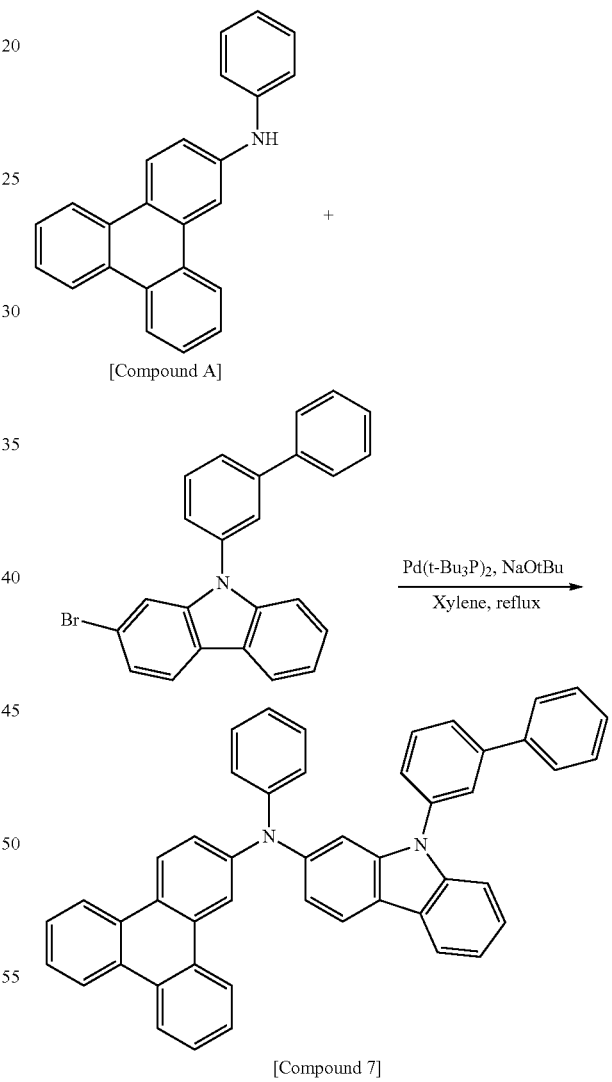

Compound A (12.0 g, 37.62 mmol) and 9-([1,1'-biphenyl]-3-yl)-2-bromo-9H-carbazole (13.58 g, 34.21 mmol) were completely dissolved in 280 ml of xylene in a 500 ml round bottom flask under nitrogen atmosphere, and then sodium tert-butoxide (4.27 g, 44.46 mol) was added thereto, bis(tri-tert-butylphosphine) palladium(0) (0.17 g, 0.34 mmol) was put thereinto, and then the resulting mixture was heated and stirred for 4 hours. The temperature of the mixture was lowered to room temperature, the resulting mixture was filtered to remove the salt, and then xylene was concentrated under reduced pressure, and the residue was recrystallized with 260 ml of ethyl acetate to prepare Compound 7 (15.36 g, yield: 64%).

MS[M+H]+=637

Preparation Example 8

Synthesis of Compound 90

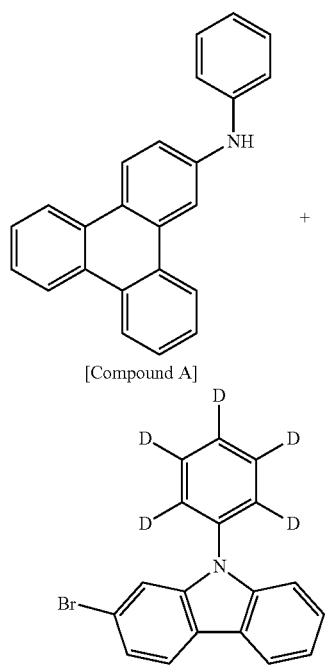

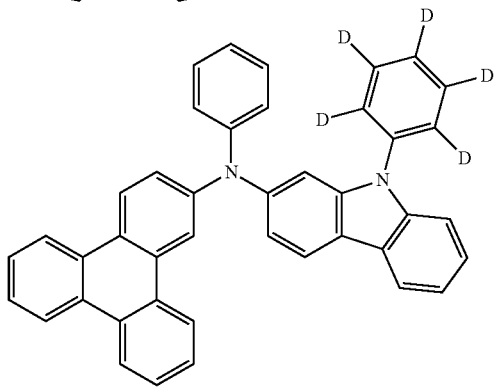

Compound A (12.0 g, 37.62 mmol) and 2-bromo-9-(phenyl-d5)-9H-carbazole (10.98 g, 34.21 mmol) were completely dissolved in 240 ml of xylene in a 500 ml round bottom flask under nitrogen atmosphere, and then sodium tert-butoxide (4.27 q, 44.46 mol) was added thereto, bis(tri-tert-butylphosphine) palladium(0) (0.17 g, 0.34 mmol) was put thereinto, and then the resulting mixture was heated and stirred for 2 hours. The temperature of the mixture was lowered to room temperature, the resulting mixture was filtered to remove the salt, and then xylene was concentrated under reduced pressure, and the residue was purified by column chromatography at a ratio of tetrahydrofuran:hexane=1:12 to prepare Compound 90 (17.35 g, yield: 82%).

MS[M+H]+=561

Preparation Example 9

Synthesis of Compound 17

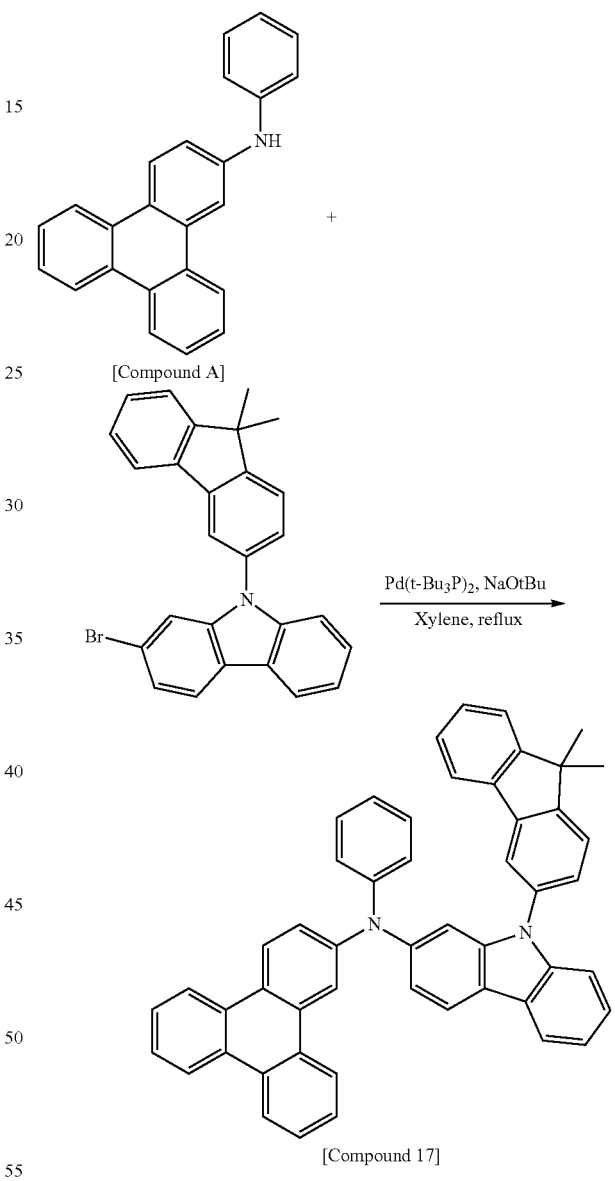

Compound A (12.0 g, 37.62 mmol) and 2-bromo-9-(9,9-dimethyl-9H-fluoren-3-yl)-9H-carbazole (14.95 g, 34.21 mmol) were completely dissolved in 240 ml of xylene in a 500 ml round bottom flask under nitrogen atmosphere, and then sodium tert-butoxide (4.27 g, 44.46 mol) was added thereto, bis(tri-tert-butylphosphine) palladium(0) (0.17 g, 0.34 mmol) was put thereinto, and then the resulting mixture was heated and stirred for 2 hours. The temperature of the mixture was lowered to room temperature, the resulting mixture was filtered to remove the salt, and then xylene was concentrated under reduced pressure, and the residue was purified by column chromatography at a ratio of tetrahydrofuran:hexane=1:15 to prepare Compound 17 (17.78 g, yield: 69%).

MS[M+H]+=677

Preparation Example 10

Synthesis of Compound 23

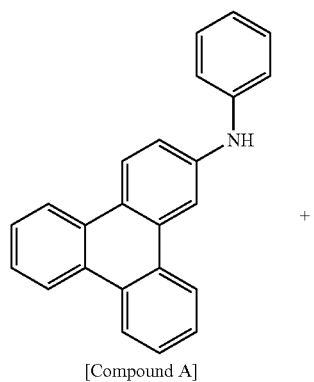

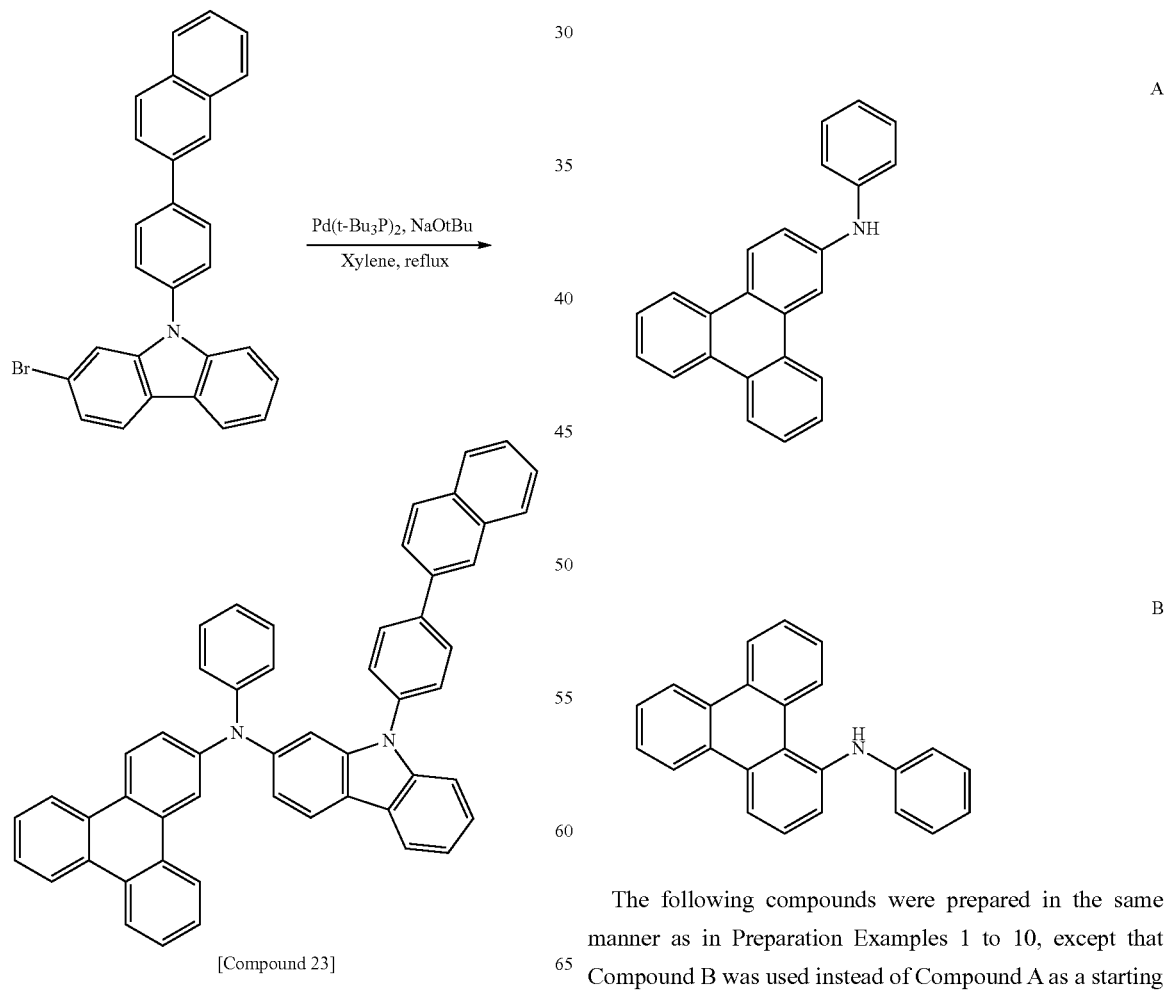

Compound A (12.0 g, 37.62 mmol) and 2-bromo-9-(4-(naphthalen-2-yl)phenyl)-9H-carbazole (16.18 g, 34.21 mmol) were completely dissolved in 240 ml of xylene in a 500 ml round bottom flask under nitrogen atmosphere, and then sodium tert-butoxide (4.27 g, 44.46 mol) was added thereto, bis(tri-tert-butylphosphine) palladium(0) (0.17 g, 0.34 mmol) was put thereinto, and then the resulting mixture was heated and stirred for 2 hours. The temperature of the mixture was lowered to room temperature, the resulting mixture was filtered to remove the salt, and then xylene was concentrated under reduced pressure, and the residue was purified by column chromatography at a ratio of tetrahydrofuran:hexane=1:12 to prepare Compound 23 (21.16 g, yield: 82%).

MS[M+H]+=687

Preparation Example 11

Synthesis of Compounds 61, 63 to 67, 71, and 91 to 94

The following compounds were prepared in the same manner as in Preparation Examples 1 to 10, except that Compound B was used instead of Compound A as a starting material.

-continued
61
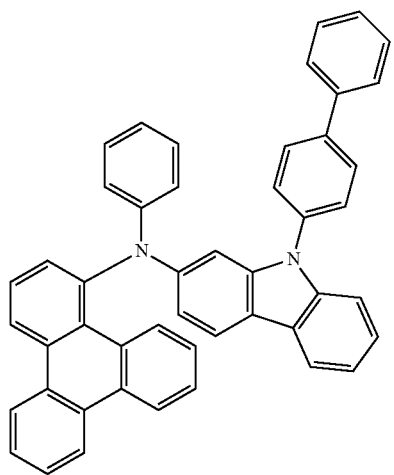
65
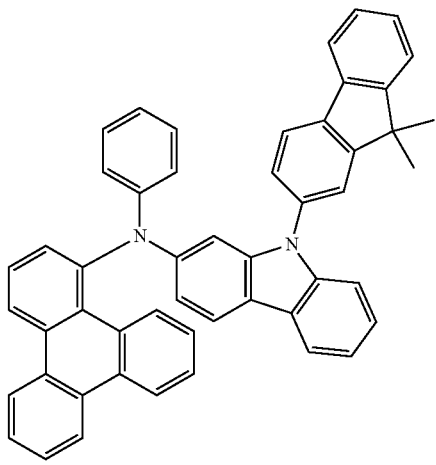
63
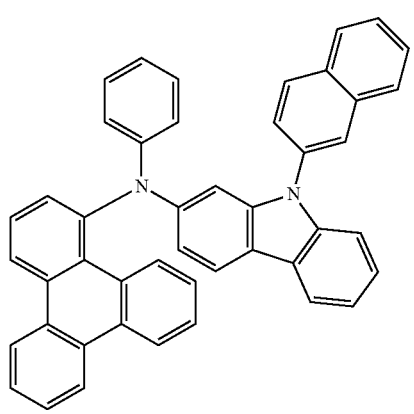
66
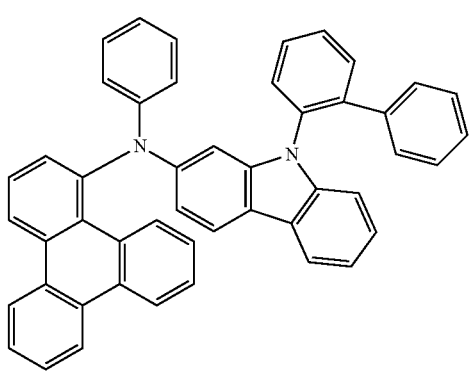
64
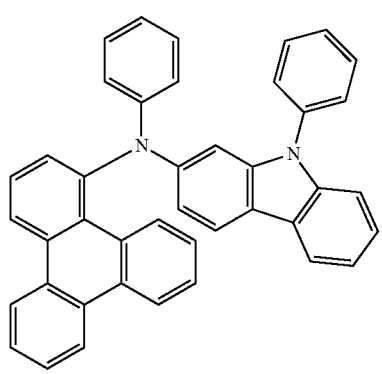
67
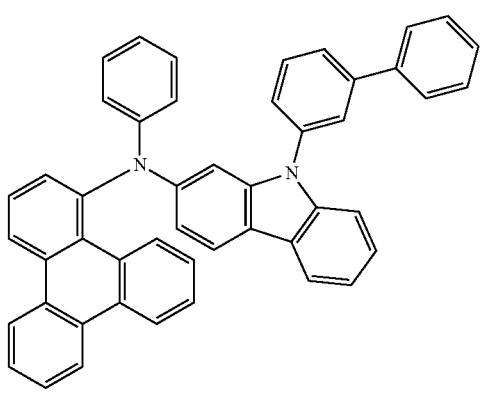

71
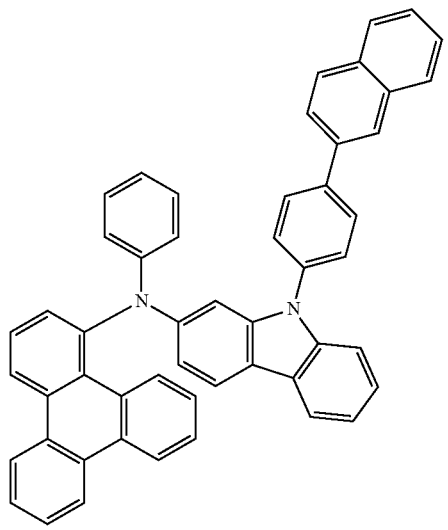
91
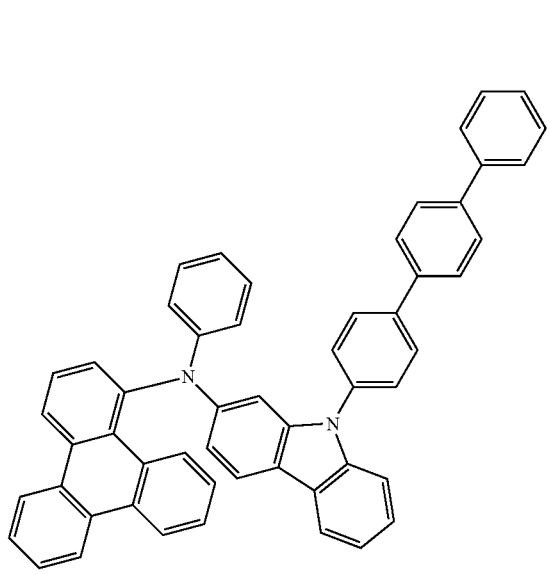
92
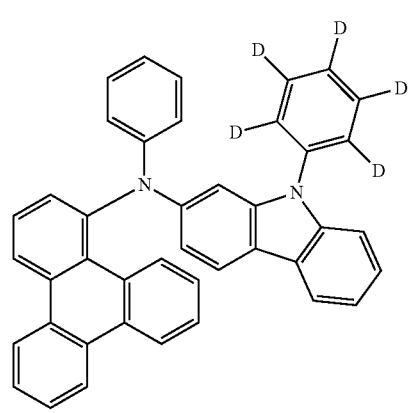
93
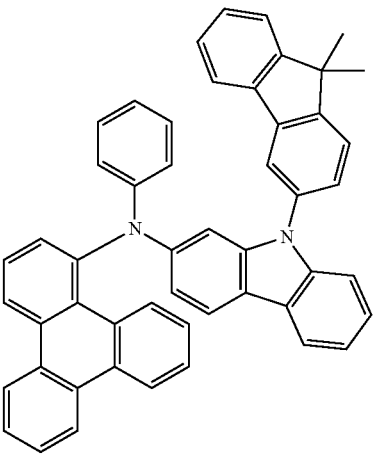
94
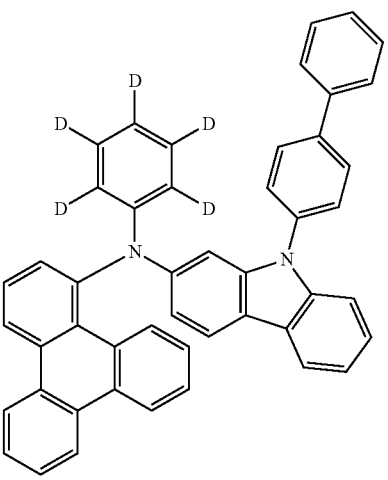
Preparation Example 12
Synthesis of Compound 29
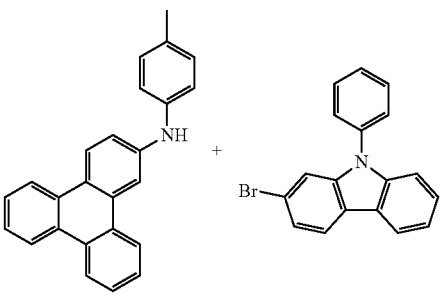
[Compound C]

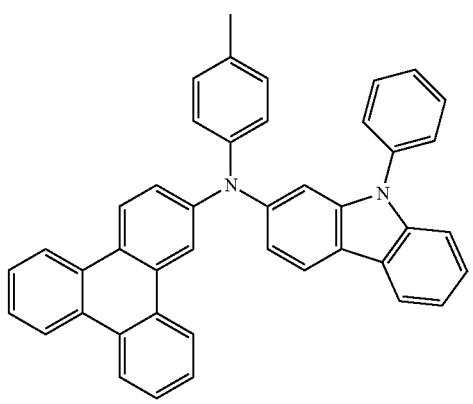

[Compound 29]

[Compound 37]

Compound C (12.0 g, 36.04 mmol) and 2-bromo-9-phenyl-9H-carbazole (10.52 g, 32.76 mmol) were completely dissolved in 230 ml of xylene in a 500 ml round bottom flask under nitrogen atmosphere, and then sodium tert-butoxide (4.09 g, 42.59 mol) was added thereto, bis(tri-tert-butylphosphine) palladium(0) (0.16 g, 0.33 mmol) was put thereinto, and then the resulting mixture was heated and stirred for 2 hours. The temperature of the mixture was lowered to room temperature, the resulting mixture was filtered to remove the salt, and then xylene was concentrated under reduced pressure, and the residue was purified by column chromatography at a ratio of tetrahydrofuran:hexane=1:12 to prepare Compound 29 (13.92 g, yield: 67%).

MS[M+H]+=575

Preparation Example 13

Synthesis of Compound 37

Compound D (12.0 g, 32.0 mmol) and 2-bromo-9-phenyl-9H-carbazole (9.34 g, 29.09 mmol) were completely dissolved in 240 ml of xylene in a 500 ml round bottom flask under nitrogen atmosphere, and then sodium tert-butoxide (3.63 g, 37.82 mol) was added thereto, bis(tri-tert-butylphosphine) palladium(0) (0.15 g, 0.29 mmol) was put thereinto, and then the resulting mixture was heated and stirred for 5 hours. The temperature of the mixture was lowered to room temperature, the resulting mixture was filtered to remove the salt, and then xylene was concentrated under reduced pressure, and the residue was recrystallized with 240 ml of ethyl acetate to prepare Compound 37 (15.01 g, yield: 76%).

MS[M+H]+=617

Preparation Example 14

Synthesis of Compound 55

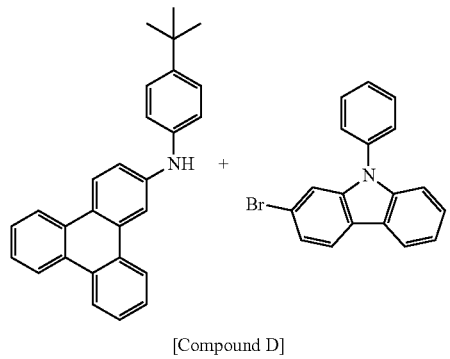 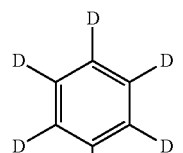

[Compound D]     [Compound F]

-continued

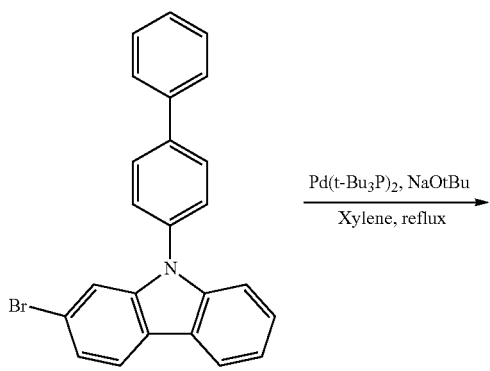

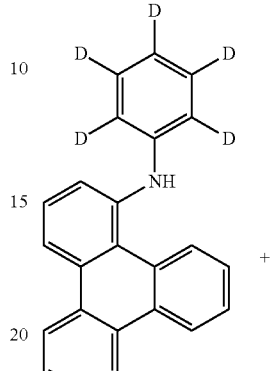

[Compound J]

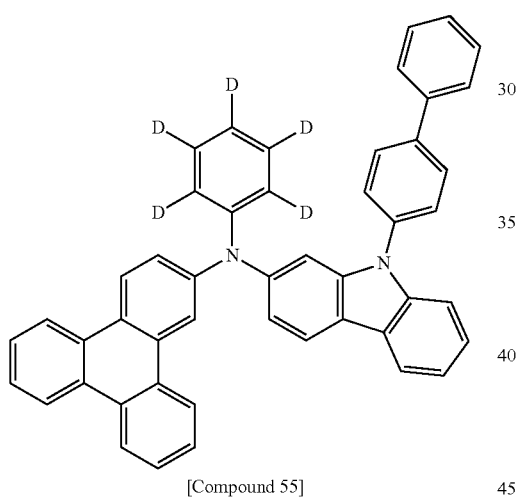

[Compound 55]

Compound F (12.0 g, 35.40 mmol) and 9-([1,1'-biphenyl]-4-yl)-2-bromo-9H-carbazole (10.33 g, 32.18 mmol) were completely dissolved in 280 ml of xylene in a 500 ml round bottom flask under nitrogen atmosphere, and then sodium tert-butoxide (4.02 g, 41.83 mol) was added thereto, bis(tri-tert-butylphosphine) palladium(0) (0.16 g, 0.32 mmol) was put thereinto, and then the resulting mixture was heated and stirred for 4 hours. The temperature of the mixture was lowered to room temperature, the resulting mixture was filtered to remove the salt, and then xylene was concentrated under reduced pressure, and the residue was recrystallized with 210 ml of ethyl acetate to prepare Compound 55 (18.85 g, yield: 83%).

MS[M+H]+=642

Preparation Example 15

Synthesis of Compound 94

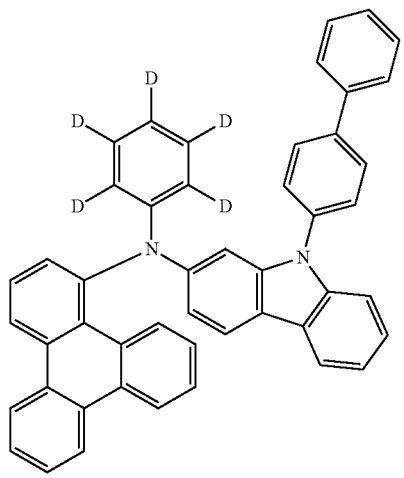

[Compound 94]

Compound J (12.0 g, 35.40 mmol) and 9-([1,1'-biphenyl]-4-yl)-2-bromo-9H-carbazole (10.33 g, 32.18 mmol) were completely dissolved in 280 ml of xylene in a 500 ml round bottom flask under nitrogen atmosphere, and then sodium tert-butoxide (4.02 g, 41.83 mol) was added thereto, bis(tri-tert-butylphosphine) palladium(0) (0.16 g, 0.32 mmol) was put thereinto, and then the resulting mixture was heated and stirred for 4 hours. The temperature of the mixture was lowered to room temperature, the resulting mixture was filtered to remove the salt, and then xylene was concentrated under reduced pressure, and the residue was recrystallized with 210 ml of ethyl acetate to prepare Compound 94 (18.85 g, yield: 83%).

MS[M+H]+=642

Experimental Examples

Experimental Example 1-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

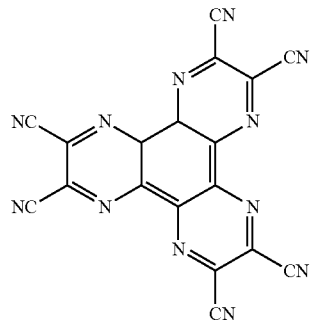

[HAT]

The following compound N-([1,1'-biphenyl]-4-yl)-9,9-dimethyl-N-(4-(9-phenyl-9H-carbazol-3-yl)phenyl)-H-fluoren-2-amine (HTL 1) (300 Å) being a material for transporting holes was vacuum deposited on the hole injection layer, thereby forming a hole transport layer.

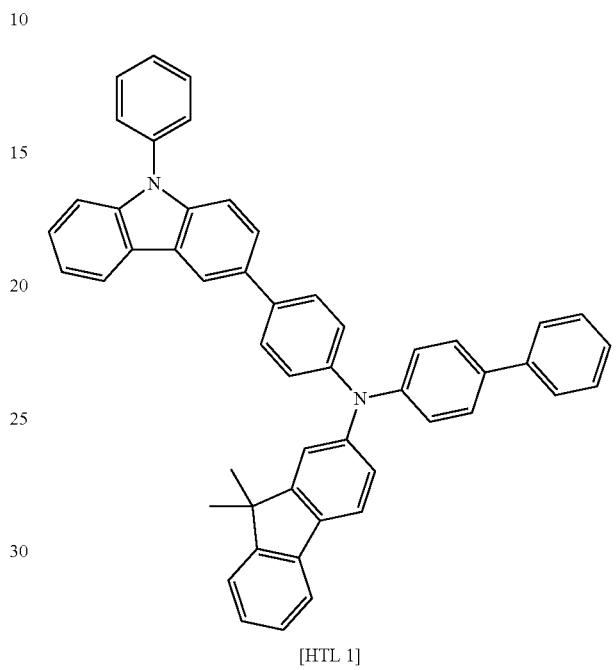

[HTL 1]

Subsequently, the following Compound 1 was vacuum deposited to have a film thickness of 100 Å on the hole transport layer, thereby forming an electron blocking layer.

[Compound 1]

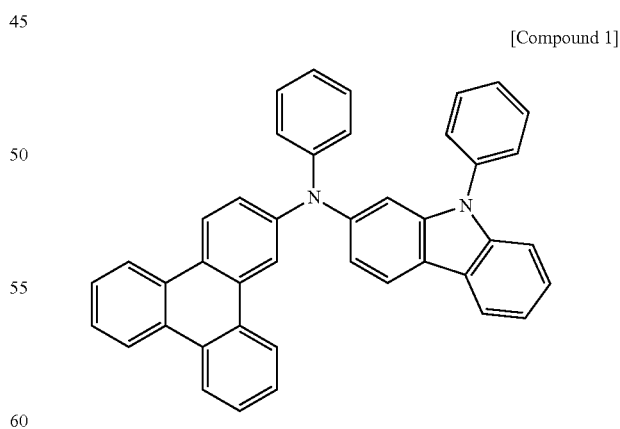

Subsequently, the following BH and BD were vacuum deposited at a weight ratio of 25:1 to have a film thickness of 300 Å on the electron blocking layer, thereby forming a light emitting layer.

[BH]

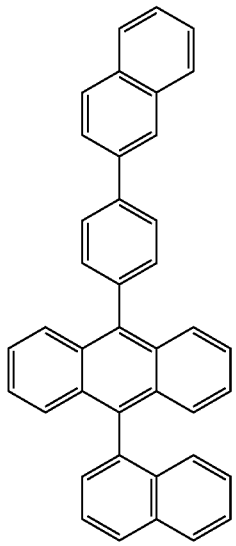

[BD]

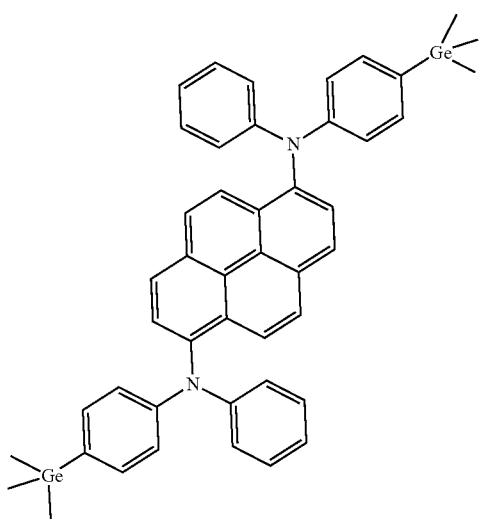

[ET1]

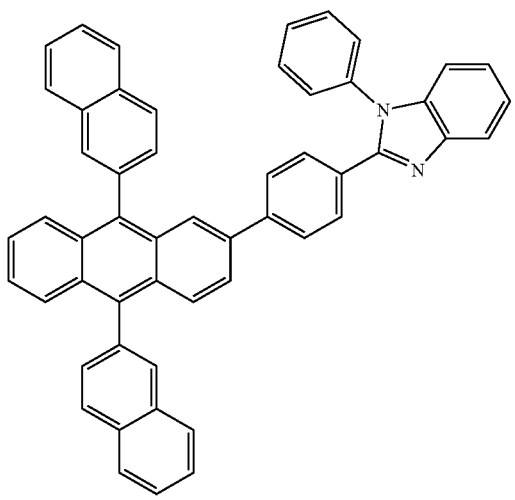

[LiQ]

Compound ET1 and Compound LiQ (lithium quinolate) were vacuum deposited at a weight ratio of 1:1 on the light emitting layer, thereby forming an electron injection and transport layer having a thickness of 300 Å. Lithium fluoride (LiF) and aluminum were sequentially deposited to have a thickness of 12 Å and 2,000 Å, respectively, on the electron injection and transport layer, thereby forming a negative electrode.

The deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-8}$ torr, thereby manufacturing an organic light emitting device.

Experimental Example 1-2

An organic light emitting device was manufactured in the same manner as in Experimental Example 1 except that Compound 3 was used instead of Compound 1 in Experimental Example 1-1.

Experimental Example 1-3

An organic light emitting device was manufactured in the same manner as in Experimental Example 1-1, except that Compound 9 was used instead of Compound 1 in Experimental Example 1-1.

Experimental Example 1-4

An organic light emitting device was manufactured in the same manner as in Experimental Example 1-1, except that Compound 5 was used instead of Compound 1 in Experimental Example 1-1.

Experimental Example 1-5

An organic light emitting device was manufactured in the same manner as in Experimental Example 1-1, except that Compound 10 was used instead of Compound 1 in Experimental Example 1-1.

Experimental Example 1-6

An organic light emitting device was manufactured in the same manner as in Experimental Example 1-1, except that Compound 89 was used instead of Compound 1 in Experimental Example 1-1.

Experimental Example 1-7

An organic light emitting device was manufactured in the same manner as in Experimental Example 1-1, except that Compound 90 was used instead of Compound 1 in Experimental Example 1-1.

Experimental Example 1-8

An organic light emitting device was manufactured in the same manner as in Experimental Example 1-1, except that Compound 64 was used instead of Compound 1 in Experimental Example 1-1.

Experimental Example 1-9

An organic light emitting device was manufactured in the same manner as in Experimental Example 1-1, except that Compound 61 was used instead of Compound 1 in Experimental Example 1-1.

Experimental Example 1-10

An organic light emitting device was manufactured in the same manner as in Experimental Example 1-1, except that Compound 91 was used instead of Compound 1 in Experimental Example 1-1.

Experimental Example 1-11

An organic light emitting device was manufactured in the same manner as in Experimental Example 1-1, except that Compound 92 was used instead of Compound 1 in Experimental Example 1-1.

Experimental Example 1-12

An organic light emitting device was manufactured in the same manner as in Experimental Example 1-1, except that Compound 29 was used instead of Compound 1 in Experimental Example 1-1.

Experimental Example 1-13

An organic light emitting device was manufactured in the same manner as in Experimental Example 1-1, except that Compound 37 was used instead of Compound 1 in Experimental Example 1-1.

Experimental Example 1-14

An organic light emitting device was manufactured in the same manner as in Experimental Example 1-1, except that Compound 55 was used instead of Compound 1 in Experimental Example 1-1.

Experimental Example 1-15

An organic light emitting device was manufactured in the same manner as in Experimental Example 1-1, except that Compound 94 was used instead of Compound 1 in Experimental Example 1-1.

Comparative Example 1-1

An organic light emitting device was manufactured in the same manner as in Experimental Example 1-1, except that EB 1 was used instead of Compound 1 in Experimental Example 1-1.

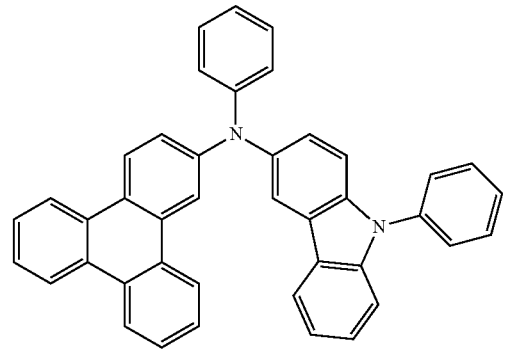

[EB 1]

Comparative Example 1-2

An organic light emitting device was manufactured in the same manner as in Experimental Example 1-1, except that EB 2 was used instead of Compound 1 in Experimental Example 1-1.

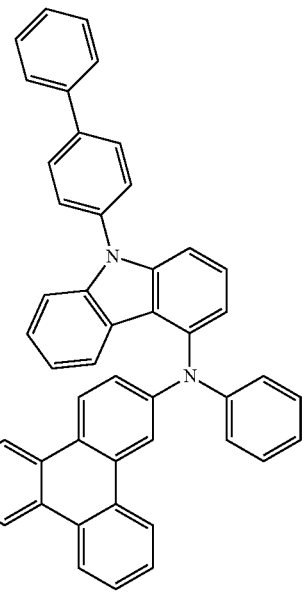

[EB 2]

Comparative Example 1-3

An organic light emitting device was manufactured in the same manner as in Experimental Example 1-1, except that EB 3 was used instead of Compound 1 in Experimental Example 1-1.

[EB 3]

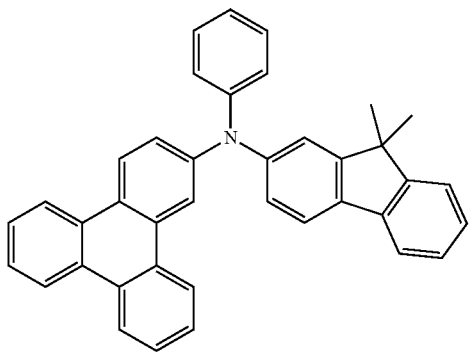

Comparative Example 1-4

An organic light emitting device was manufactured in the same manner as in Experimental Example 1 except that EB 4 was used instead of Compound 1 in Experimental Example 1-1.

[EB 4]

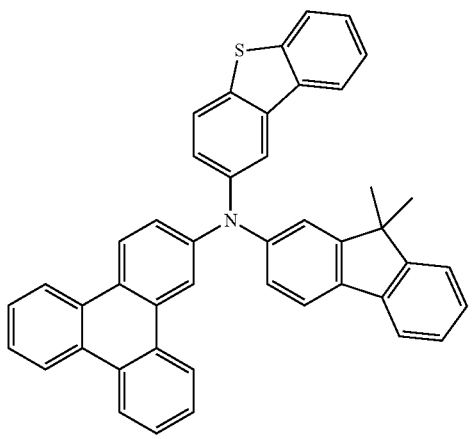

Comparative Example 1-5

An organic light emitting device was manufactured in the same manner as in Experimental Example 1-1, except that EB 5 was used instead of Compound 1 in Experimental Example 1-1.

[EB 5]

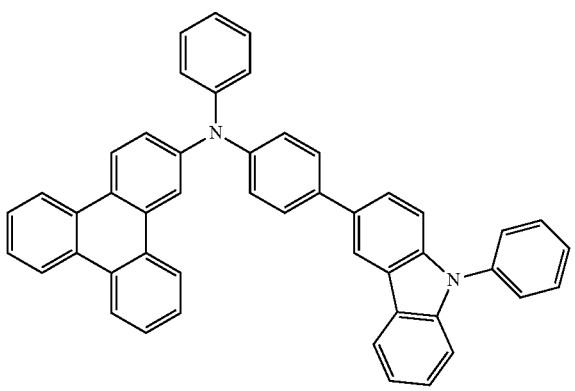

When current was applied to the organic light emitting devices manufactured in Experimental Examples 1-1 to 1-15 and Comparative Examples 1-1 to 1-5, the results of Table 1 were obtained.

TABLE 1

| | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1 | 3.55 | 5.85 | (0.139, 0.122) |
| Experimental Example 1-2 | Compound 3 | 3.52 | 5.88 | (0.138, 0.126) |
| Experimental Example 1-3 | Compound 9 | 3.61 | 5.71 | (0.138, 0.127) |
| Experimental Example 1-4 | Compound 5 | 3.62 | 5.72 | (0.137, 0.125) |
| Experimental Example 1-5 | Compound 10 | 3.64 | 5.73 | (0.136, 0.125) |
| Experimental Example 1-6 | Compound 89 | 3.66 | 5.77 | (0.136, 0.127) |
| Experimental Example 1-7 | Compound 90 | 3.68 | 5.78 | (0.136, 0.125) |
| Experimental Example 1-8 | Compound 64 | 3.74 | 5.61 | (0.137, 0.125) |
| Experimental Example 1-9 | Compound 61 | 3.73 | 5.68 | (0.138, 0.125) |
| Experimental Example 1-10 | Compound 91 | 3.78 | 5.62 | (0.136, 0.125) |
| Experimental Example 1-11 | Compound 92 | 3.79 | 5.57 | (0.137, 0.125) |
| Experimental Example 1-12 | Compound 29 | 3.75 | 5.55 | (0.136, 0.125) |
| Experimental Example 1-13 | Compound 37 | 3.82 | 5.58 | (0.138, 0.126) |
| Experimental Example 1-14 | Compound 55 | 3.87 | 5.51 | (0.137, 0.125) |
| Experimental Example 1-15 | Compound 94 | 3.80 | 5.42 | (0.136, 0.127) |
| Comparative Example 1-1 | EB 1 | 4.56 | 4.73 | (0.138, 0.127) |
| Comparative Example 1-2 | EB 2 | 4.61 | 4.52 | (0.139, 0.125) |
| Comparative Example 1-3 | EB 3 | 4.79 | 4.36 | (0.139, 0.126) |
| Comparative Example 1-4 | EB 4 | 4.26 | 5.05 | (0.139, 0.127) |
| Comparative Example 1-5 | EB 5 | 4.33 | 4.94 | (0.139, 0.127) |

As observed in Table 1, it can be seen that the compounds in Experimental Examples 1-1 to 1-15 exhibit lower voltage and higher efficiency characteristics in an organic light emitting device than those in Comparative Examples 1-1 to 1-5.

When an N atom is linked to No. 3 or 4 of a carbazole group as in Comparative Example 1-1 or Comparative Example 1-2, the voltage was relatively high, and the efficiency thereof was also low. The case where a fluorenyl group or a dibenzothiophene group is used instead of a carbazole group (Comparative Example 1-3 and Comparative Example 1-4) and the case where a carbazole group is linked to an N atom through a linking group being an arylene group (Comparative Example 1-5) also exhibited similar characteristics.

It could be confirmed that the compound according to the present invention, which is linked to an N atom at the No. 2 position of the carbazole without a linking group, has excellent electron blocking ability, and thus exhibits low voltage and high efficiency characteristics, and can be applied to an organic light emitting device.

Experimental Example 2

Experimental Example 2-1 to Experimental Example 2-15

An experiment was performed in the same manner as in Experimental Example 1-1, except that EB 1 (TCTA) was used as the electron blocking layer, and the compounds in Experimental Examples 1-1 to 1-15 were used instead of HTL 1 as the hole transport layer.

Comparative Example 2-1

An organic light emitting device was manufactured in the same manner as in Experimental Example 2-1, except that HT 1 was used instead of Compound 1.

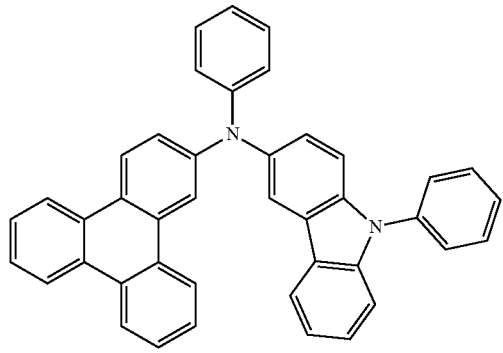

[HT 1]

Comparative Example 2-2

An organic light emitting device was manufactured in the same manner as in Experimental Example 2-1, except that HT 2 was used instead of Compound 1.

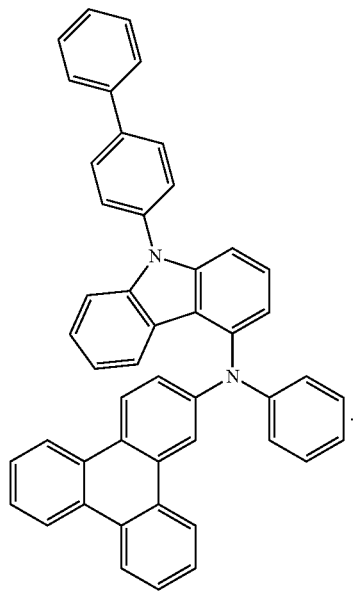

[HT 2]

Comparative Example 2-3

An organic light emitting device was manufactured in the same manner as in Experimental Example 2-1, except that HT 3 was used instead of Compound 1.

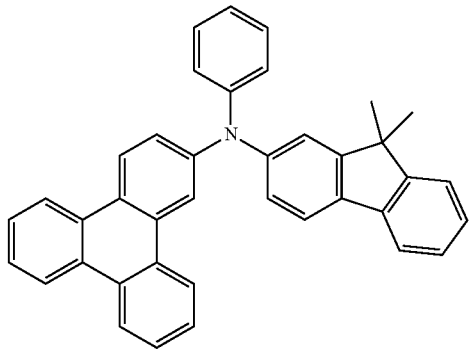

[HT 3]

Comparative Example 2-4

An organic light emitting device was manufactured in the same manner as in Experimental Example 2-1, except that HT 4 was used instead of Compound 1.

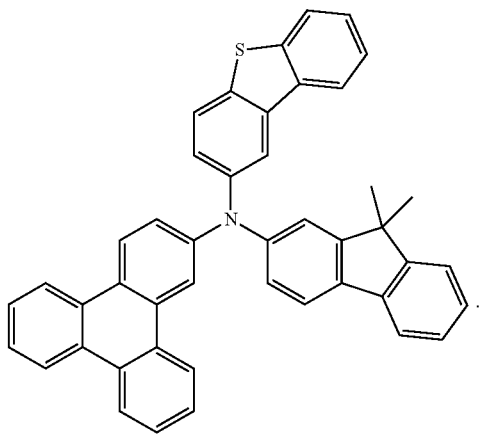

[HT 4]

Comparative Example 2-5

An organic light emitting device was manufactured in the same manner as in Experimental Example 2-1, except that HT 5 was used instead of Compound 1.

[HT 5]

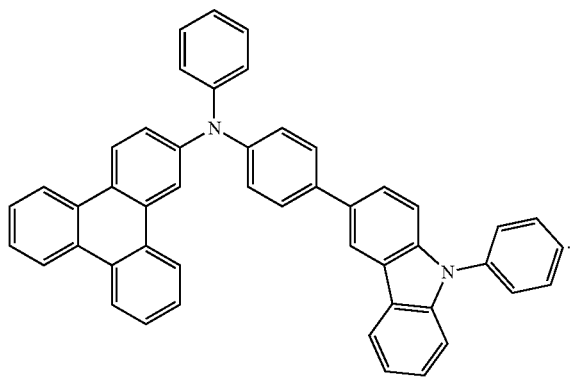

When current was applied to the organic light emitting devices manufactured in Experimental Examples 2-1 to 2-15 and Comparative Examples 2-1 to 2-5, the results of Table 2 were obtained.

TABLE 2

| | Compound (Hole transport layer) | Voltage (V@10 mA/cm$^2$) | Efficiency (cd/A@10 mA/cm$^2$) | Color coordinate (x, y) |
|---|---|---|---|---|
| Experimental Example 2-1 | Compound 1 | 3.72 | 6.35 | (0.139, 0.122) |
| Experimental Example 2-2 | Compound 3 | 3.79 | 6.28 | (0.138, 0.126) |
| Experimental Example 2-3 | Compound 9 | 3.75 | 6.31 | (0.138, 0.127) |
| Experimental Example 2-4 | Compound 5 | 3.85 | 6.24 | (0.137, 0.125) |
| Experimental Example 2-5 | Compound 10 | 3.86 | 6.22 | (0.136, 0.125) |
| Experimental Example 2-6 | Compound 89 | 3.84 | 6.13 | (0.136, 0.127) |
| Experimental Example 2-7 | Compound 90 | 3.89 | 6.11 | (0.136, 0.125) |
| Experimental Example 2-8 | Compound 64 | 3.95 | 6.02 | (0.137, 0.125) |
| Experimental Example 2-9 | Compound 61 | 3.93 | 6.01 | (0.138, 0.125) |
| Experimental Example 2-10 | Compound 91 | 3.98 | 5.92 | (0.136, 0.125) |
| Experimental Example 2-11 | Compound 92 | 3.93 | 5.95 | (0.137, 0.125) |
| Experimental Example 2-12 | Compound 29 | 4.05 | 5.95 | (0.136, 0.125) |
| Experimental Example 2-13 | Compound 37 | 4.06 | 5.82 | (0.138, 0.126) |
| Experimental Example 2-14 | Compound 55 | 4.10 | 5.76 | (0.137, 0.125) |
| Experimental Example 2-15 | Compound 94 | 4.15 | 5.74 | (0.136, 0.127) |
| Comparative Example 2-1 | HT 1 | 4.51 | 4.72 | (0.135, 0.127) |
| Comparative Example 2-2 | HT 2 | 4.64 | 4.65 | (0.138, 0.127) |
| Comparative Example 2-3 | HT 3 | 4.48 | 4.86 | (0.137, 0.125) |
| Comparative Example 2-4 | HT 4 | 4.60 | 4.34 | (0.139, 0.126) |
| Comparative Example 2-5 | HT 5 | 4.65 | 4.40 | (0.139, 0.127) |

As observed in Table 2, it can be seen that the compounds in Experimental Examples 2-1 to 2-15 exhibit lower voltage and higher efficiency characteristics than those in Comparative Examples 2-1 to 2-5 when the compounds in Experimental Examples 2-1 to 2-15 are used for an organic light emitting device.

When an N atom is linked to No. 3 or 4 position of a carbazole group as in Comparative Example 2-1 or Comparative Example 2-2, the driving voltage of the organic light emitting device was relatively high, and the efficiency thereof was also low. The case where a fluorenyl group or a dibenzothiophene group is used instead of a carbazole group (Comparative Example 2-3 and Comparative Example 2-4) and the case where a carbazole group is linked to an N atom through a linking group being an arylene group (Comparative Example 2-5) also exhibited similar characteristics. It could be confirmed that the compound according to the present invention, which is linked to an N atom at the No. 2 position of the carbazole without a linking group, also has excellent hole transport ability, and thus exhibits low voltage and high efficiency characteristics, and can be applied to an organic light emitting device.

Although the preferred exemplary embodiments (an electron blocking layer and a hole transport layer) of the present invention have been described above, the present invention is not limited thereto, and various modifications can be made and carried out within the scope of the claims and the detailed description of the invention, and also fall within the scope of the invention.

The invention claimed is:

1. A compound represented by the following Chemical Formula 1:

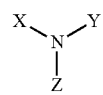

Chemical Formula 1 in Chemical Formula 1,

X is

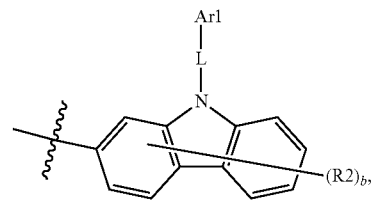

Y is

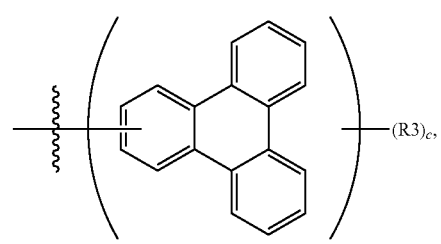

Z is

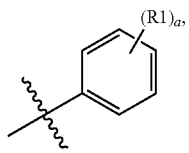

Ar1 is a substituted or unsubstituted aryl group,

L is a direct bond; or a substituted or unsubstituted arylene group,

R1 is hydrogen; deuterium; or a substituted or unsubstituted alkyl group,

R2 and R3 are the same as or different from each other, and are each independently hydrogen; a substituted or unsubstituted alkyl group; or a substituted or unsubstituted aryl group, a is an integer of 0 to 5, b is an integer of 0 to 7, c is an integer of 0 to 11, and when a is 2 or more, R1's are the same as or different from each other, when b is 2 or more, R2's are the same as or different from each other, and when c is 2 or more, R3's are the same as or different from each other.

2. The compound of claim 1, wherein Chemical Formula 1 is represented by the following Chemical Formula 2 or 3:

[Chemical Formula 2]

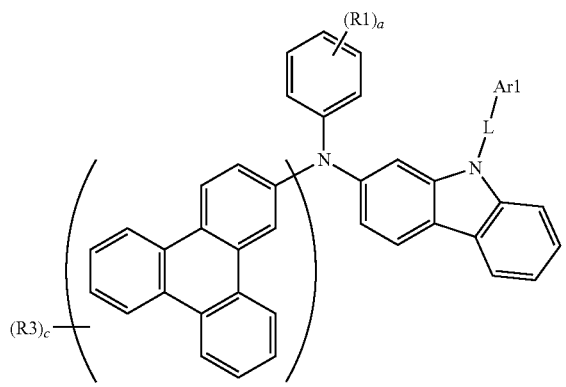

[Chemical Formula 3]

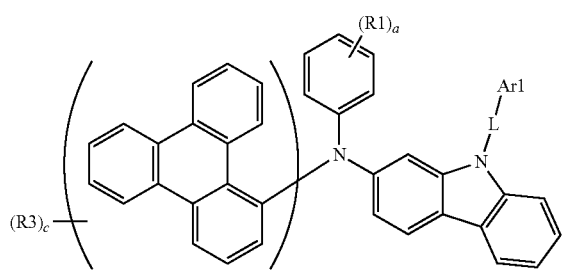

in Chemical Formula 2 and Chemical Formula 3, the definitions of Ar1, L, R1, R3, a, and c are each the same as those in Chemical Formula 1.

3. The compound of claim 1, wherein Chemical Formula 1 is represented by the following Chemical Formula 4 or 5:

[Chemical Formula 4]

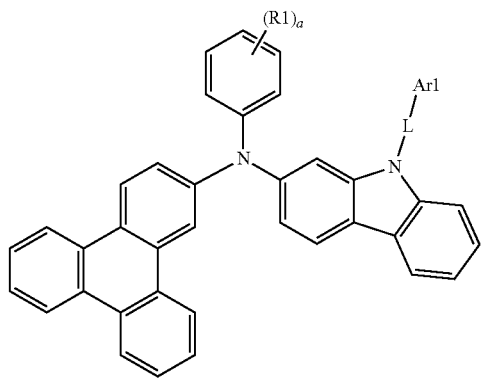

[Chemical Formula 5]

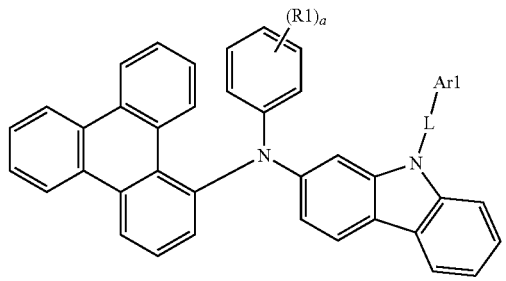

in Chemical Formula 4 and Chemical Formula 5, the definitions of Ar1, L, R1, and a are each the same as those in Chemical Formula 1.

4. The compound of claim 1, wherein Ar1 is a substituted or unsubstituted phenyl group; a substituted or unsubstituted biphenyl group; a substituted or unsubstituted terphenyl group; a substituted or unsubstituted naphthyl group; a substituted or unsubstituted fluorenyl group; a substituted or unsubstituted phenanthrenyl group; or a substituted or unsubstituted triphenylenyl group.

5. The compound of claim 1, wherein Ar1 is any one selected from the following structures:

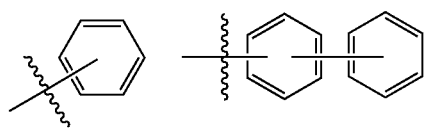

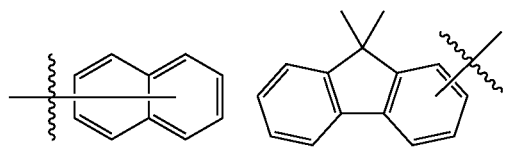

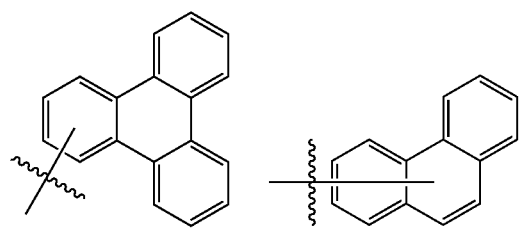

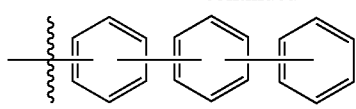
the structures are optionally substituted or unsubstituted with deuterium; an alkyl group; or an aryl group.
6. The compound of claim 1, wherein the compound of Chemical Formula 1 is any one selected from the following structural formulae:
1
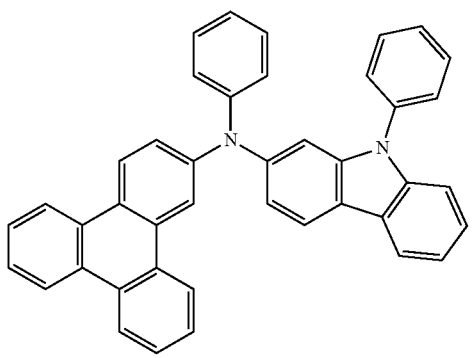
2
4
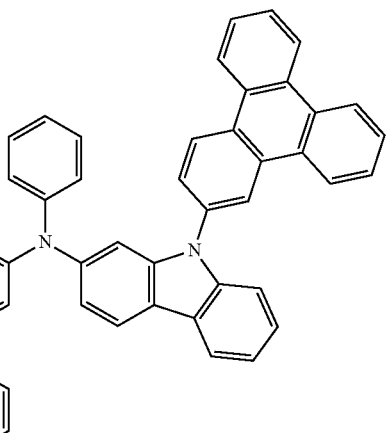
5
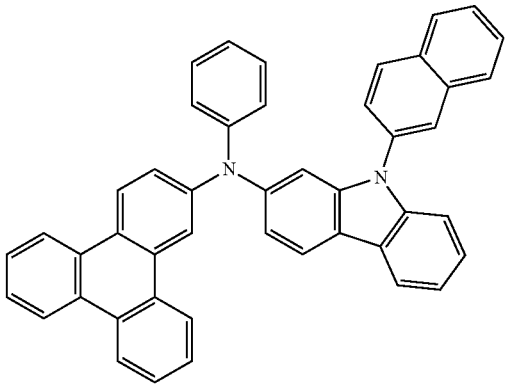
3
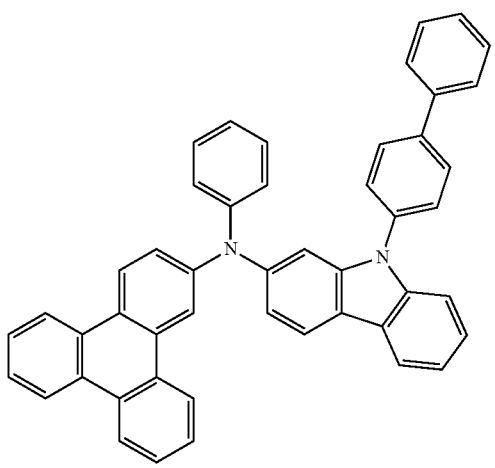
6
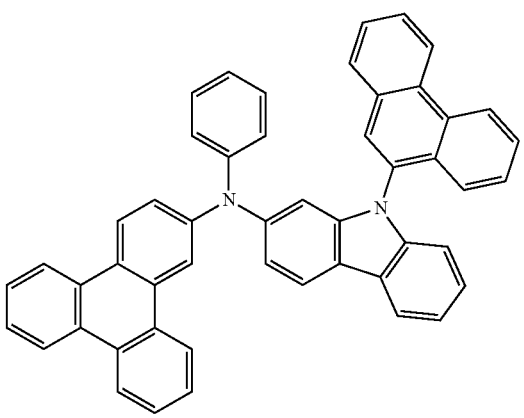

-continued
7
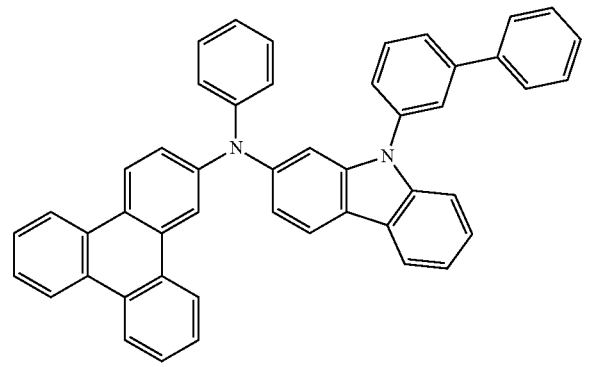
8
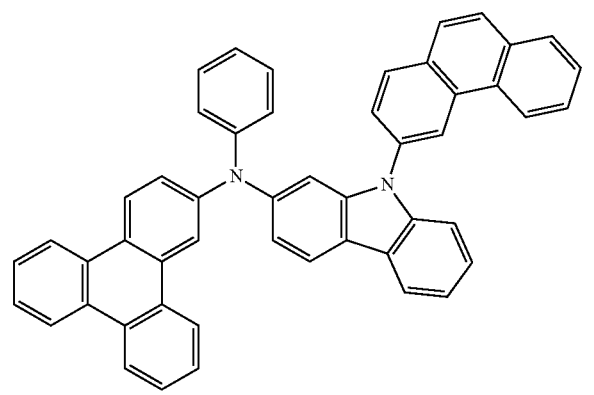
9
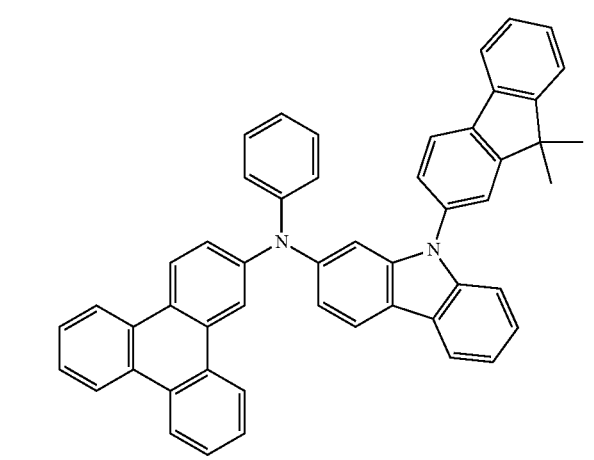
10
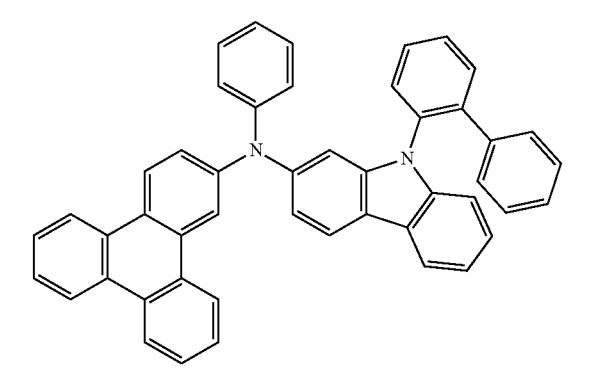
-continued
11
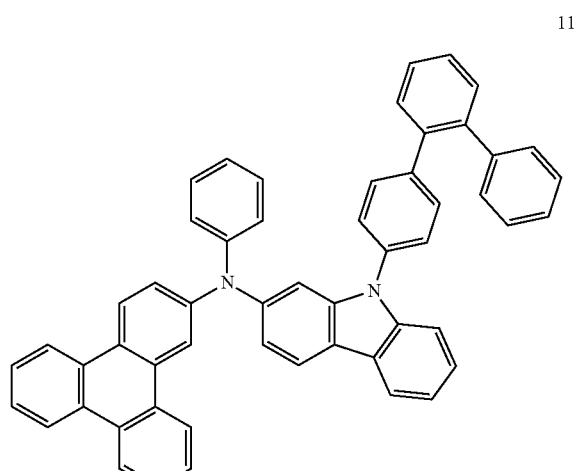
12
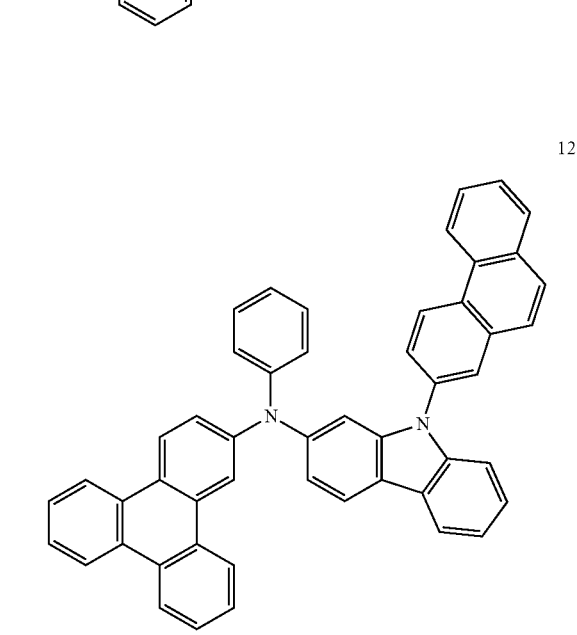
13
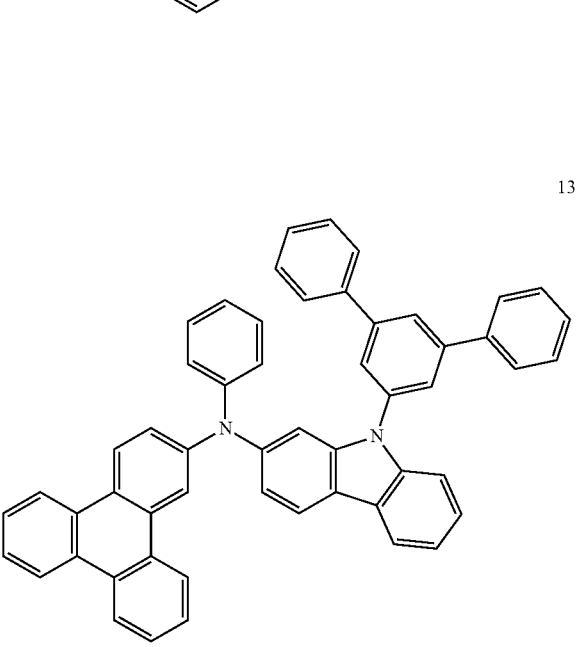

14
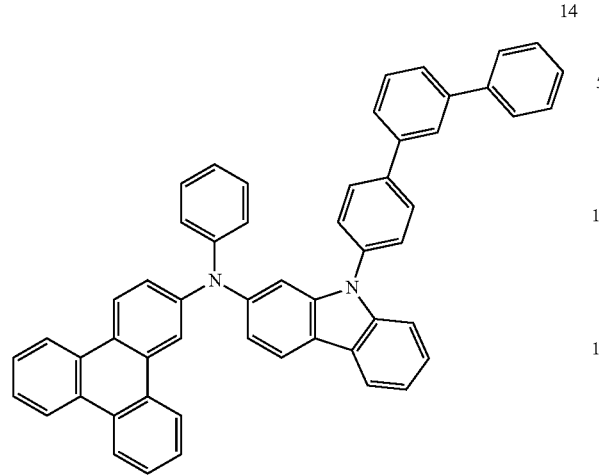
15
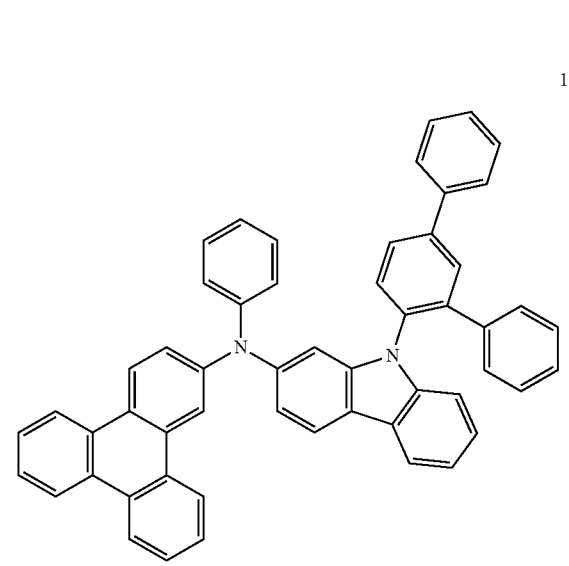
16
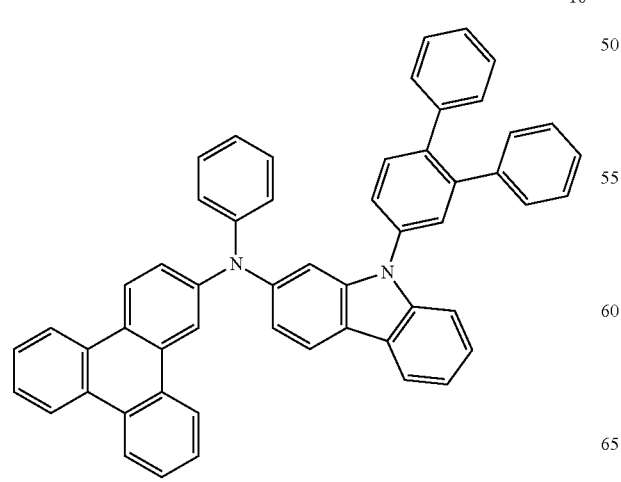
17
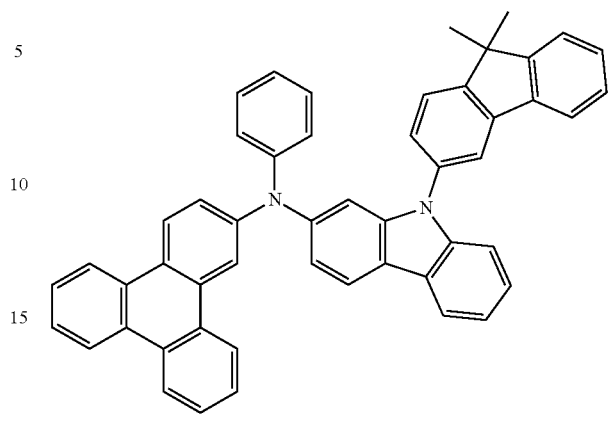
18
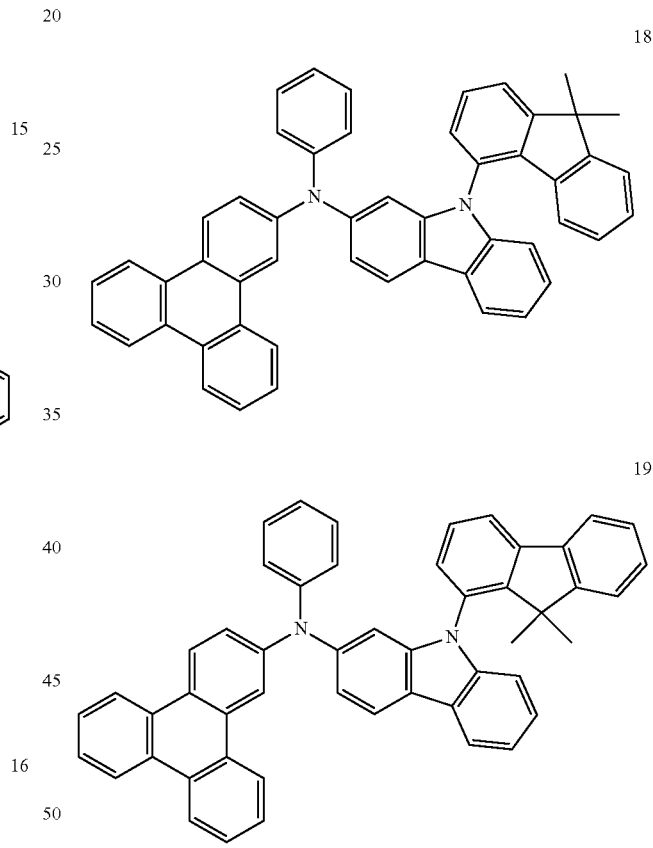
19
20

21
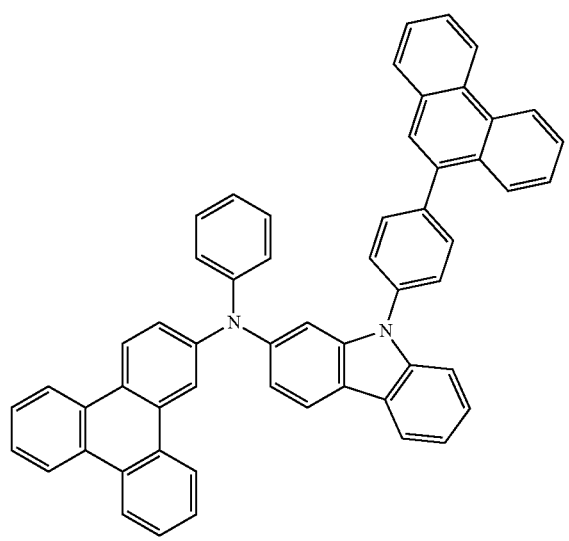
22
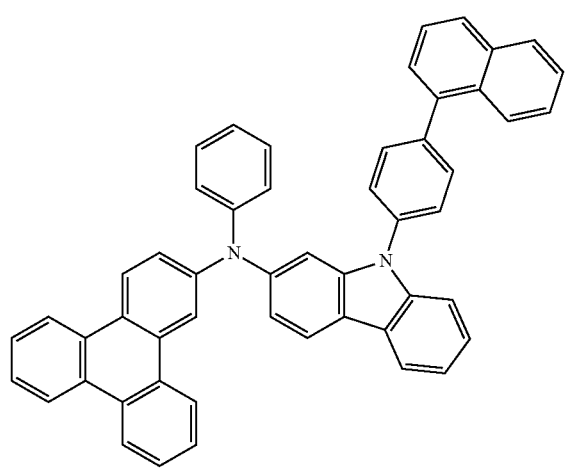
23
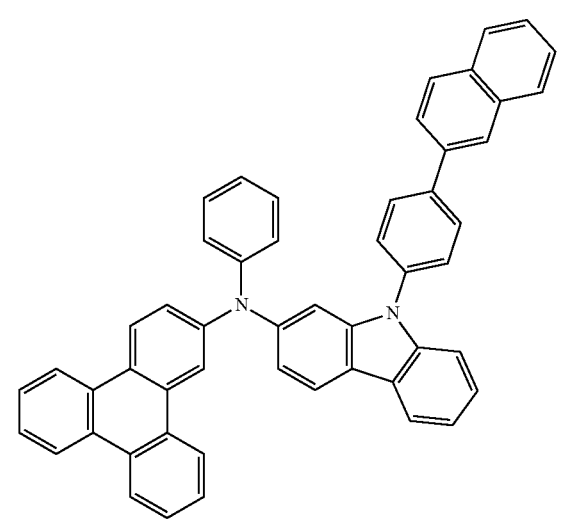
24
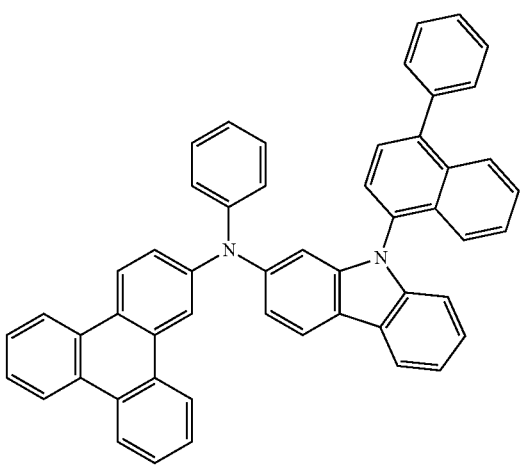
25
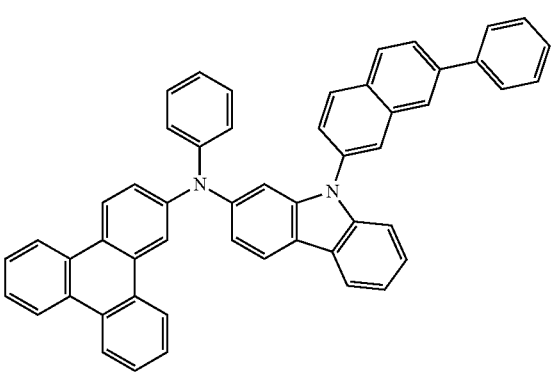
26
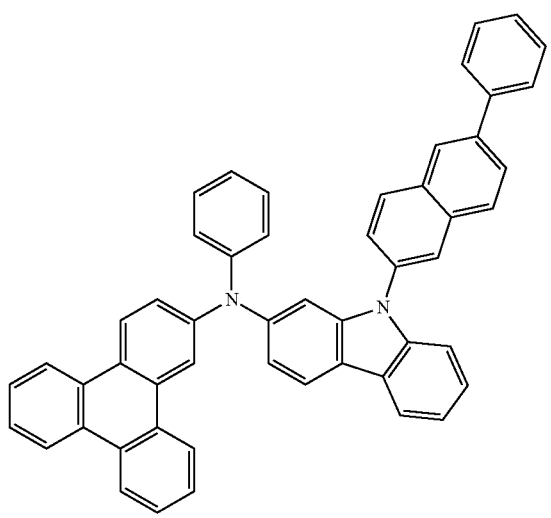

27
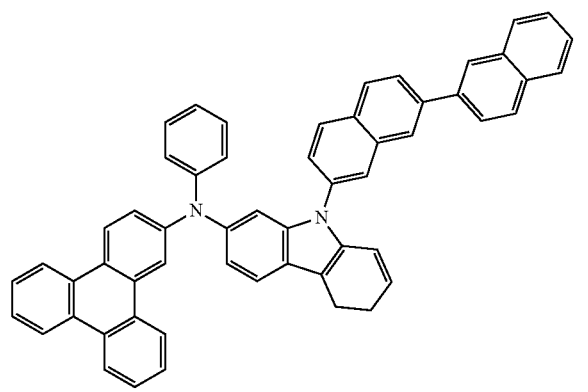
28
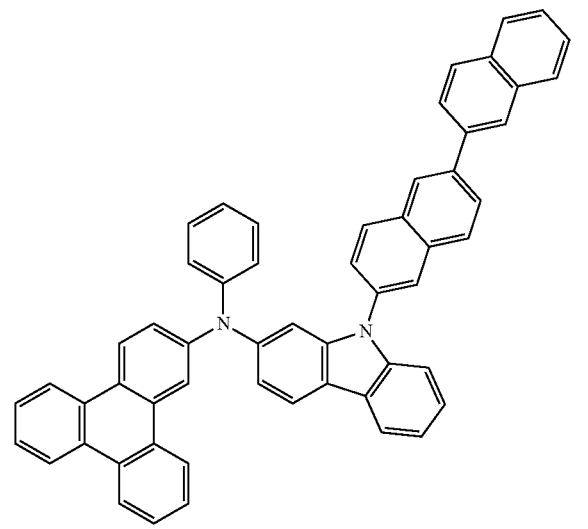
30
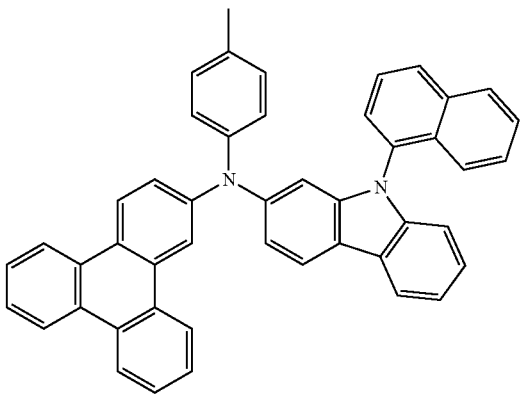
31
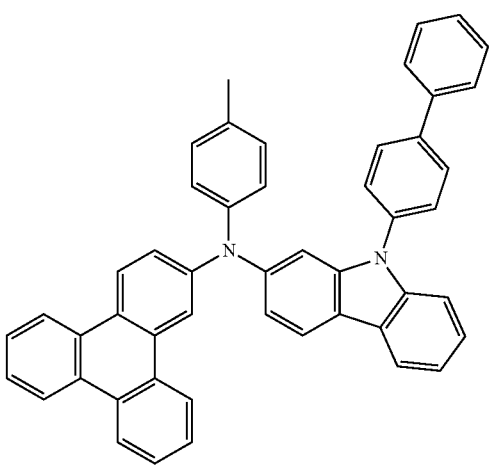
29
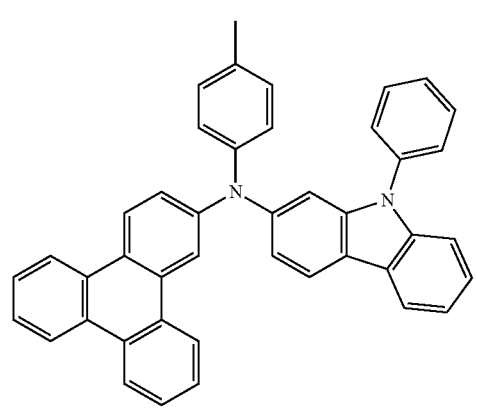
32
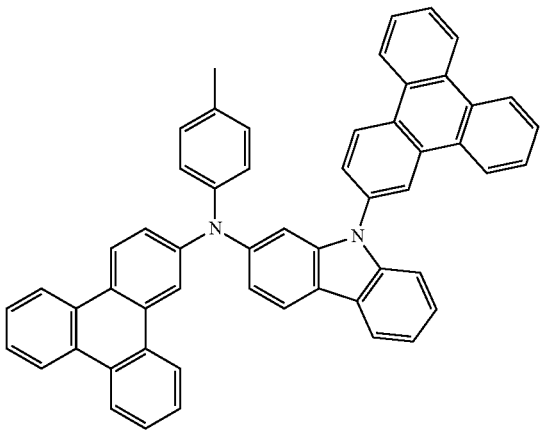

33
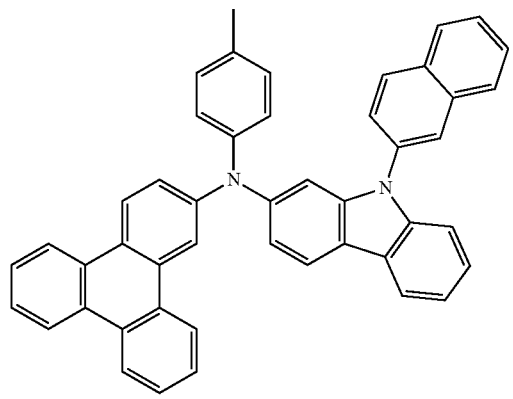
34
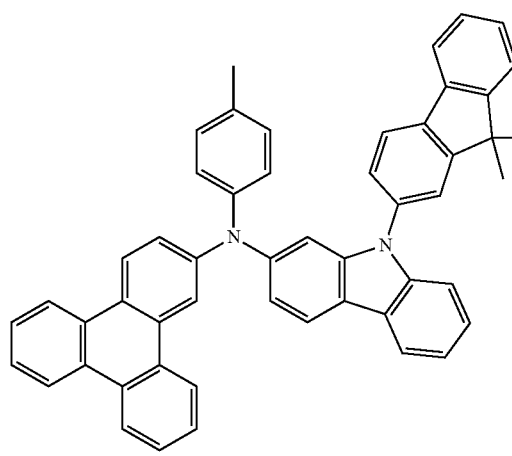
35
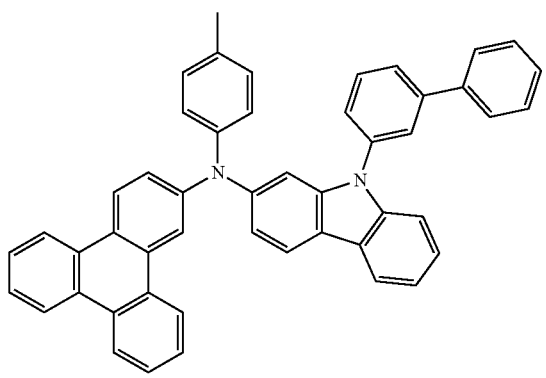
36
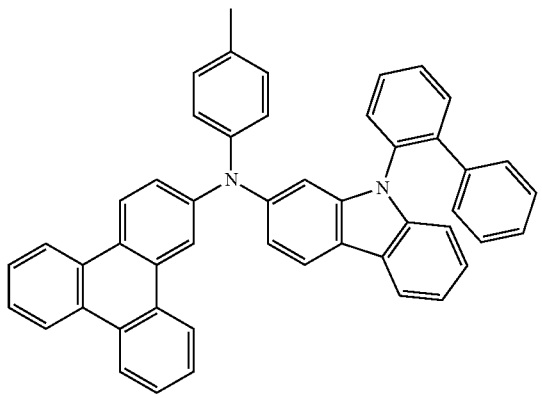
37
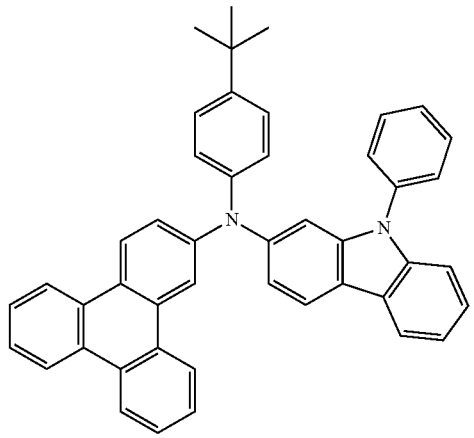
38
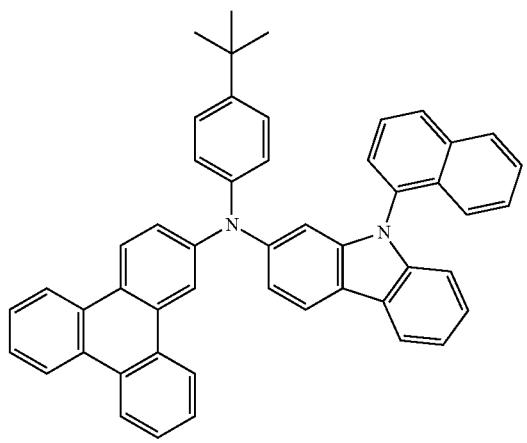

39
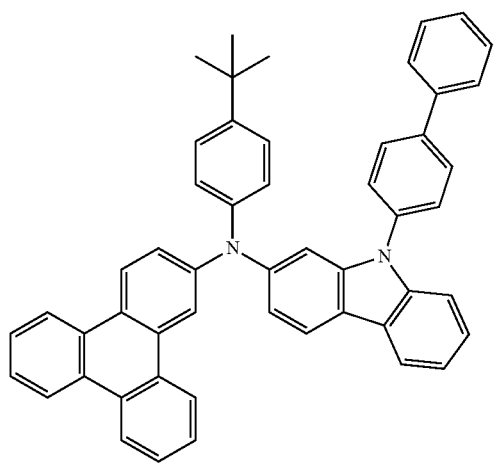
40
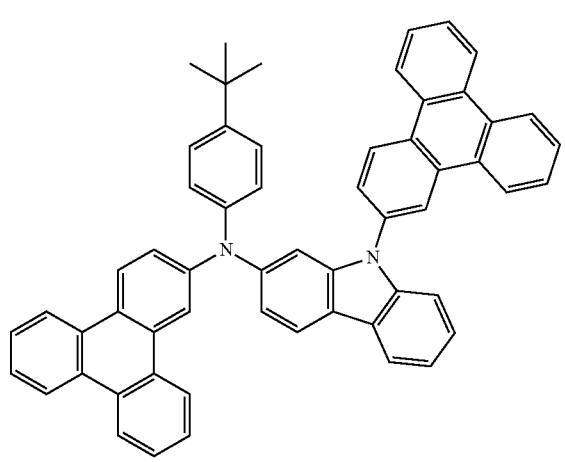
41
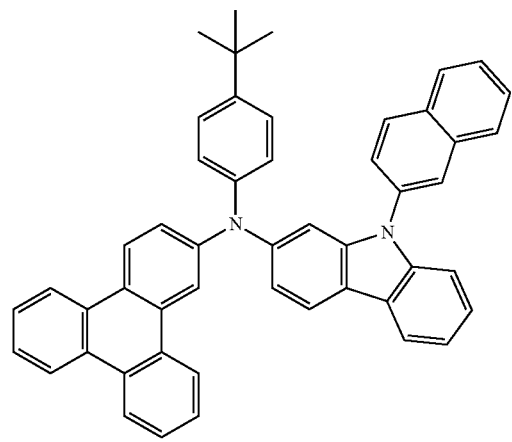
42
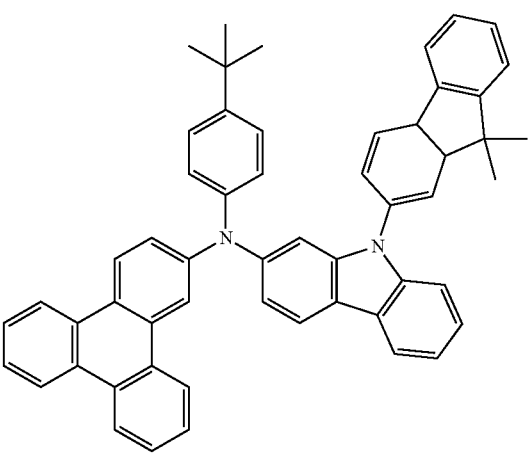
43
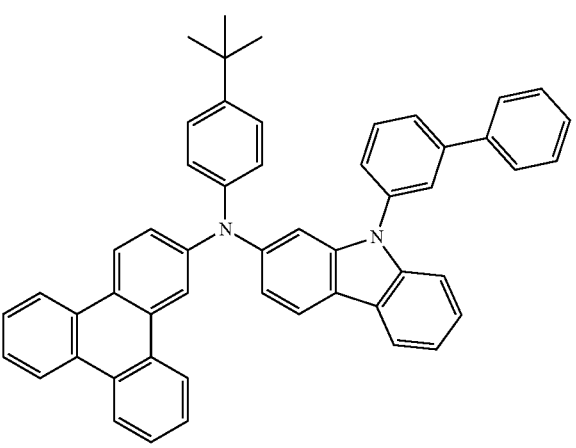
44
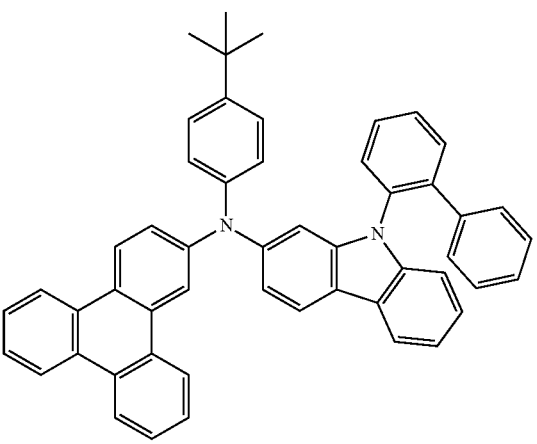

45
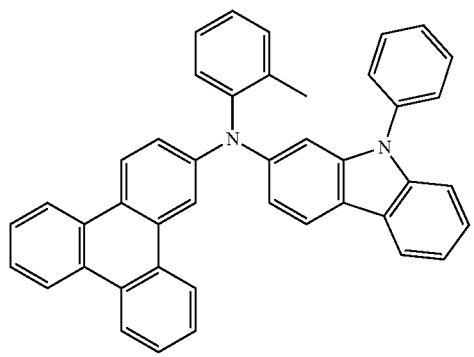
48
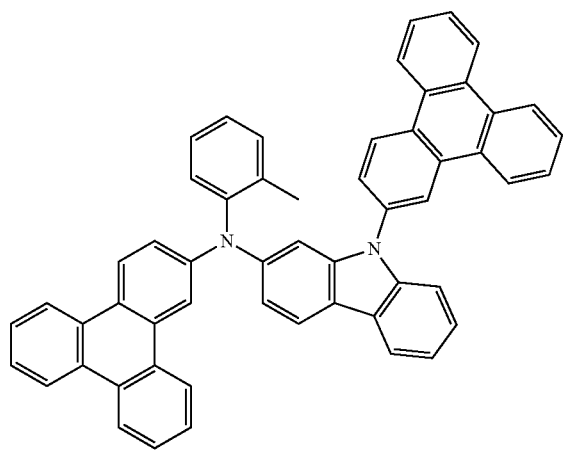
46
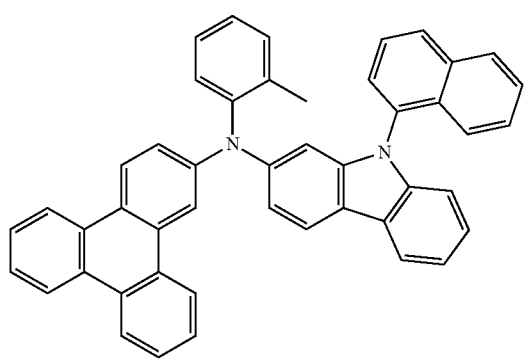
49
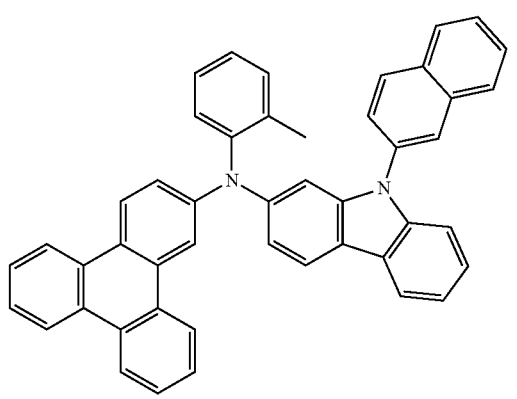
47
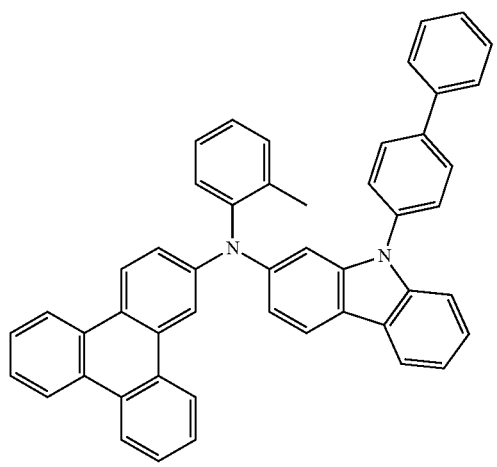
50
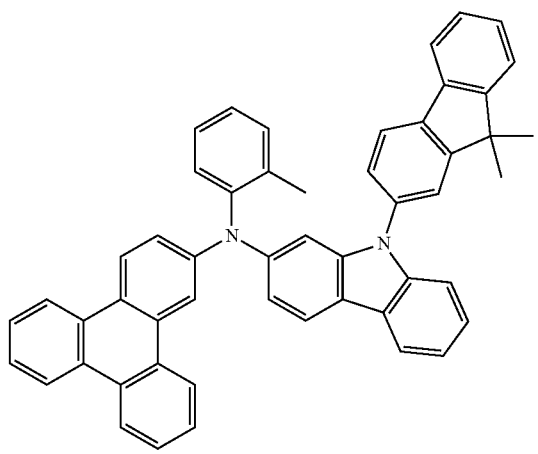

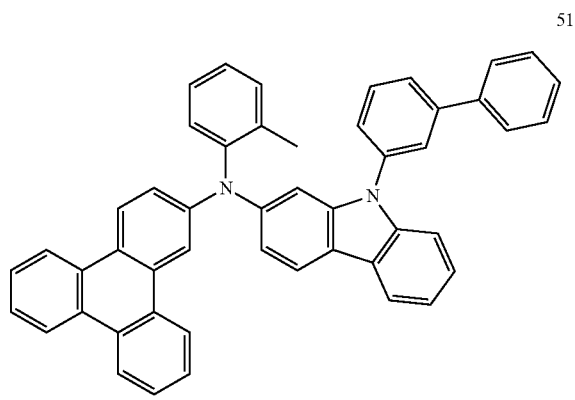
51
52
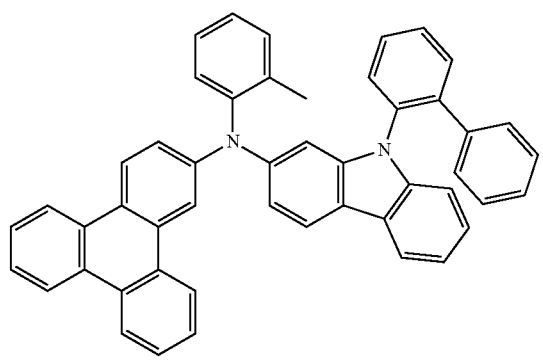
53
54
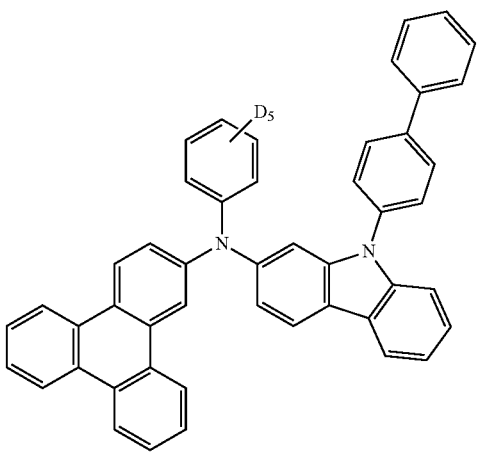
55
56
57
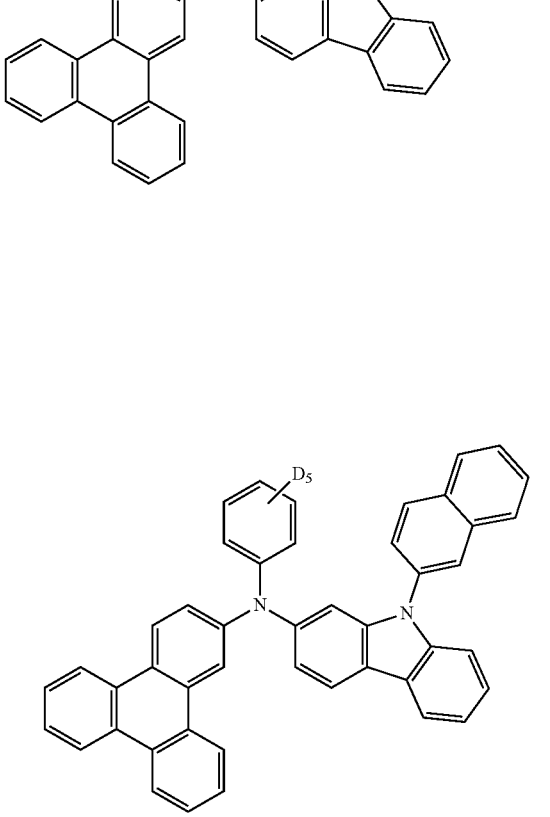

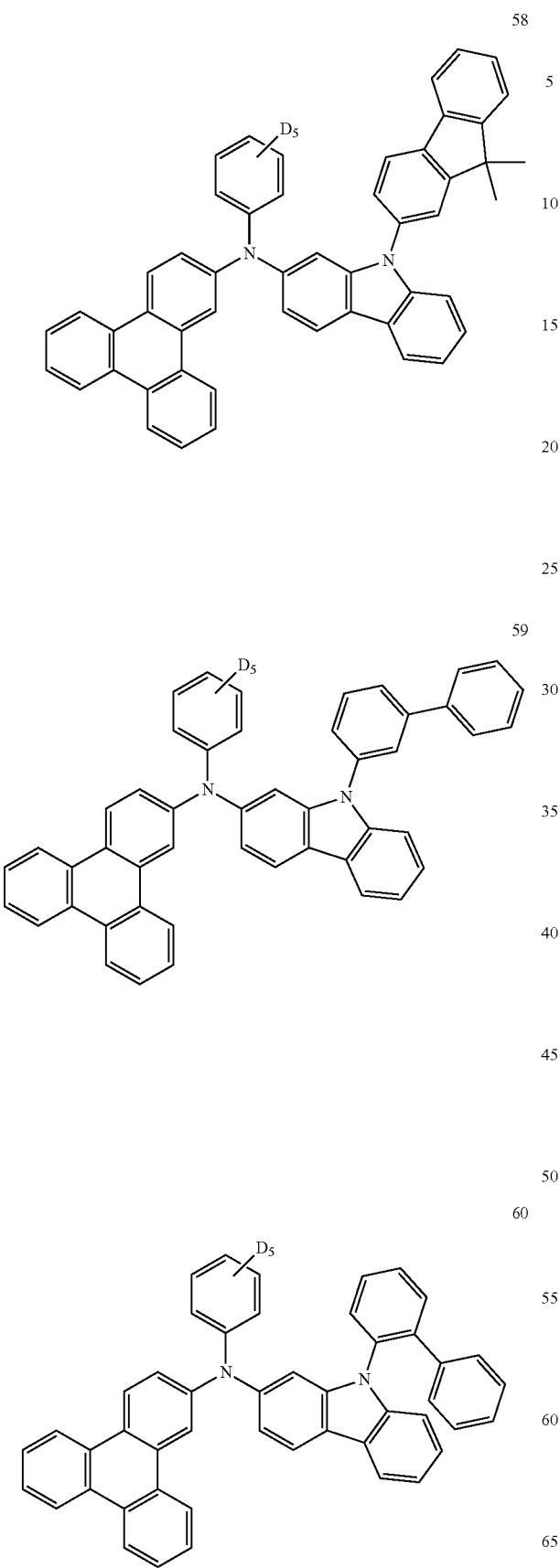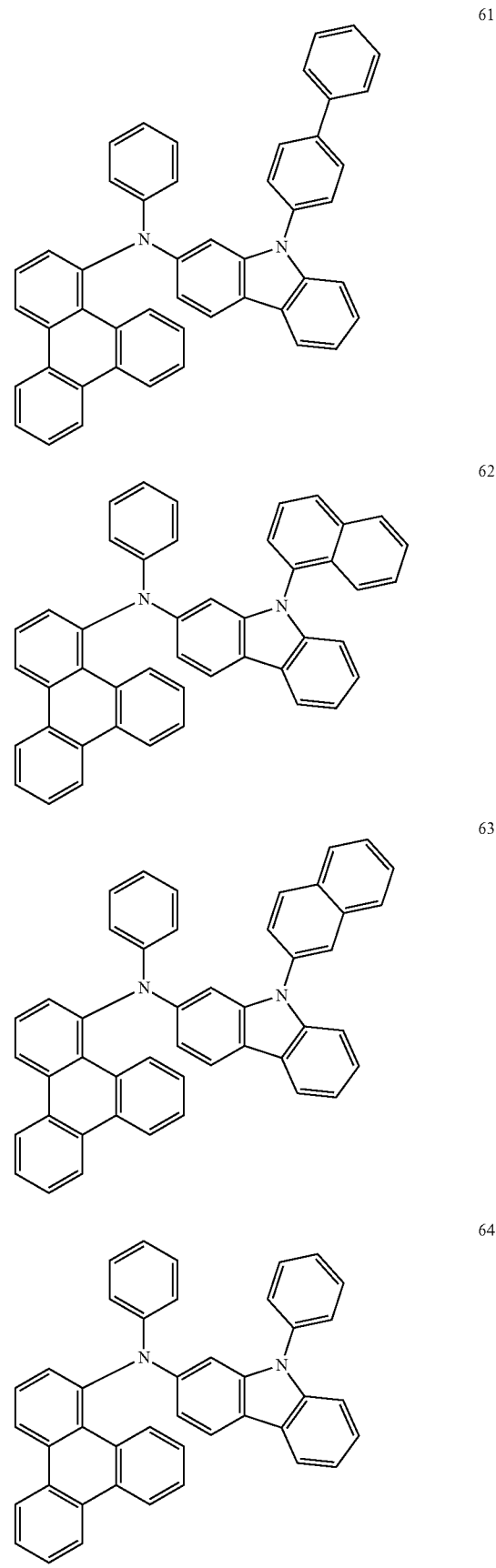

-continued
65
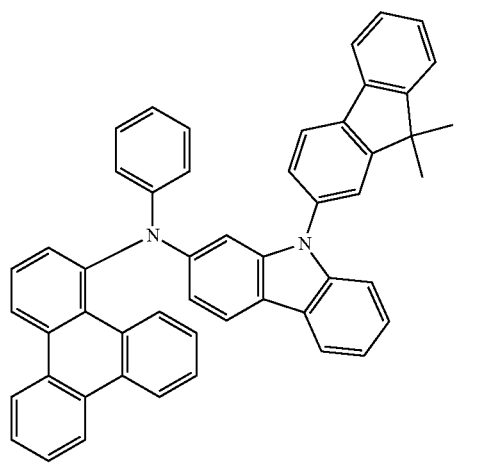
66
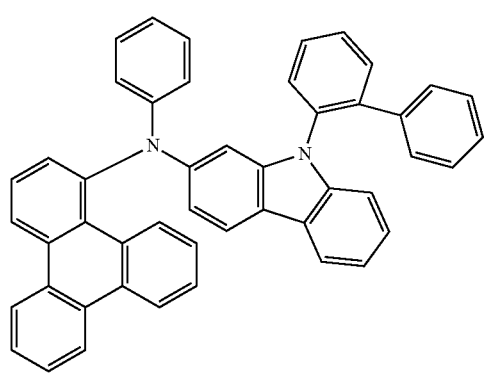
67
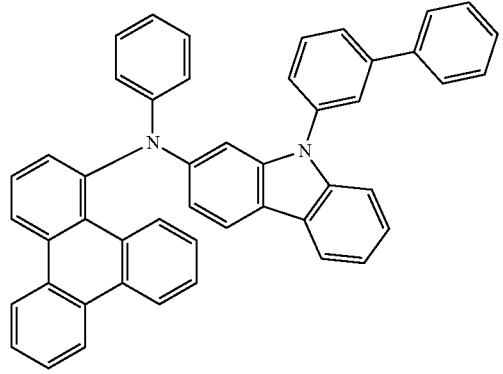
68
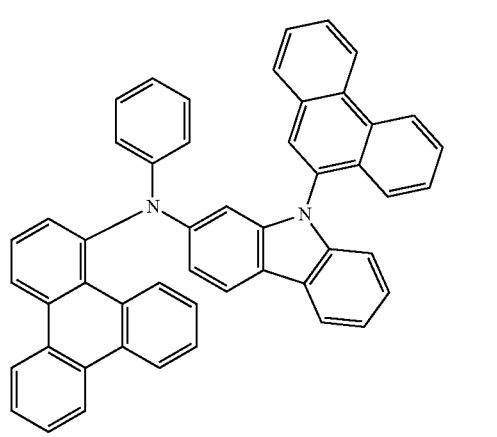
-continued
69
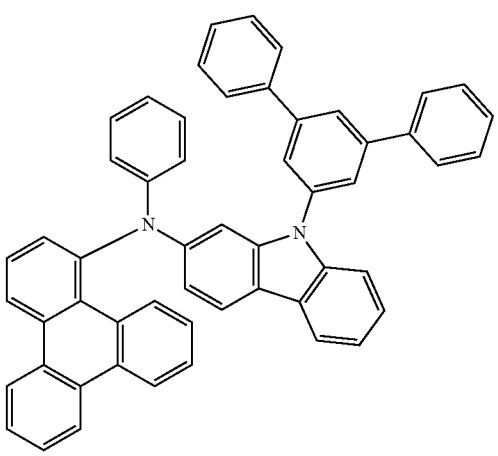
70
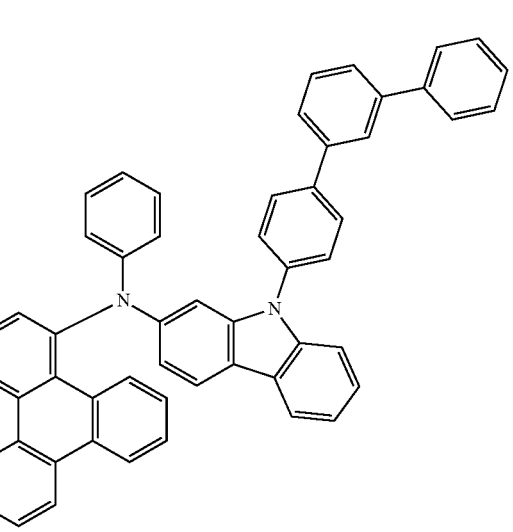
71
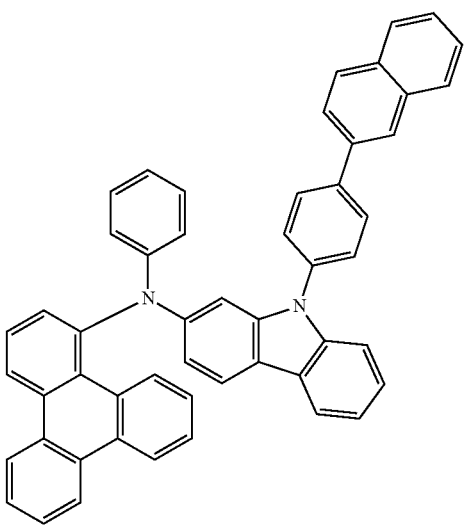

72
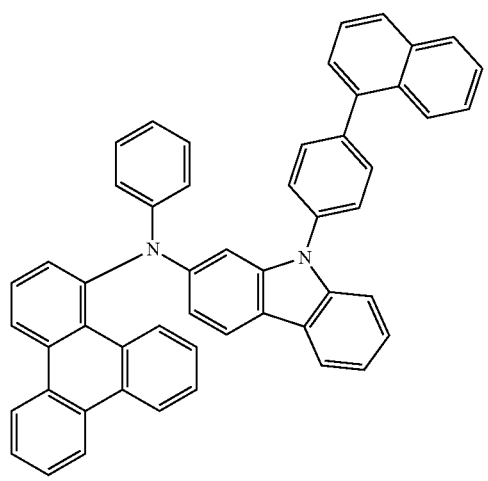
73
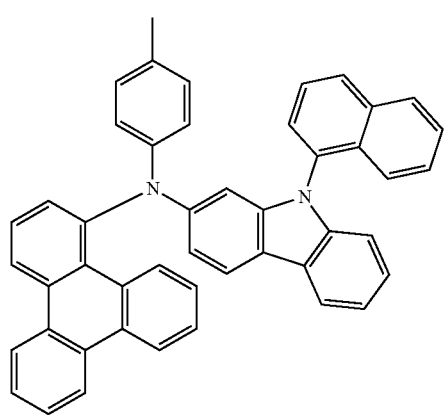
74
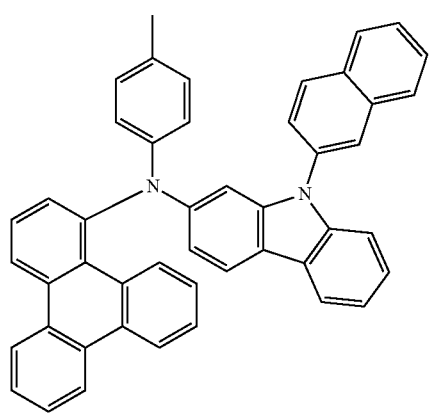
75
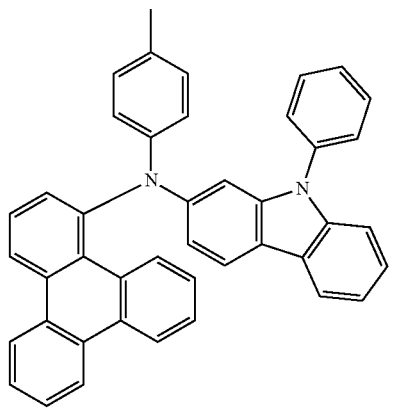
76
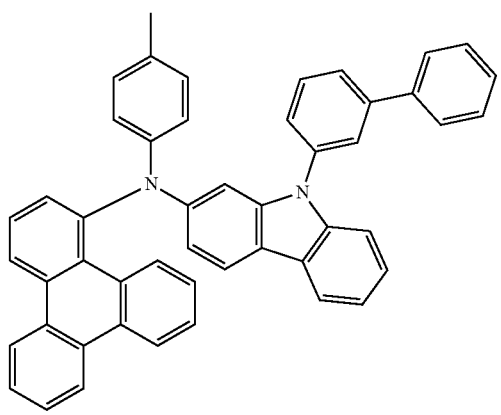
77
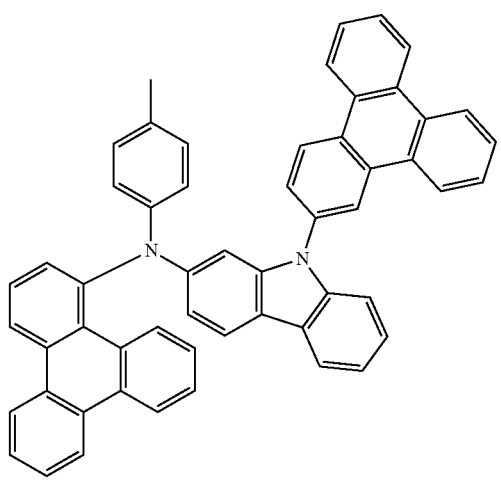

78
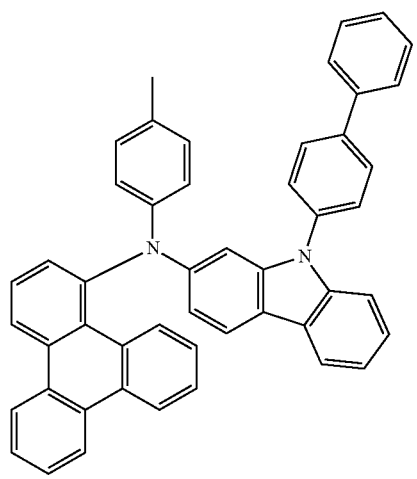
79
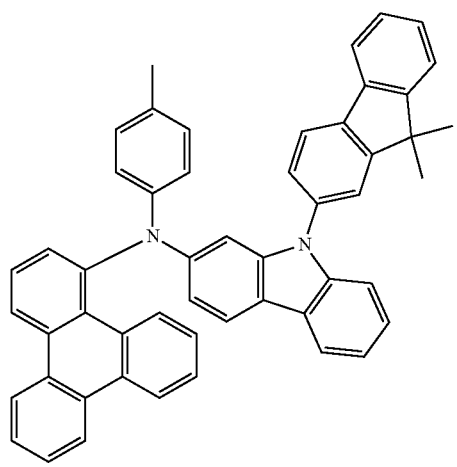
80
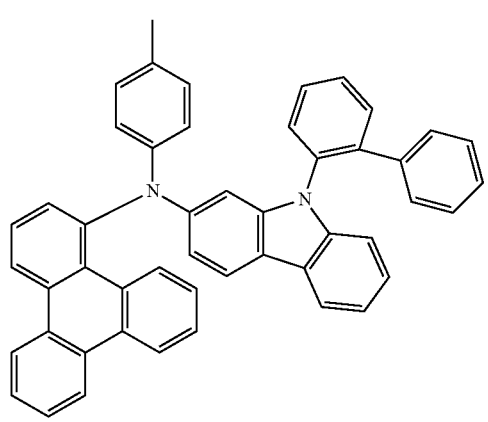
81
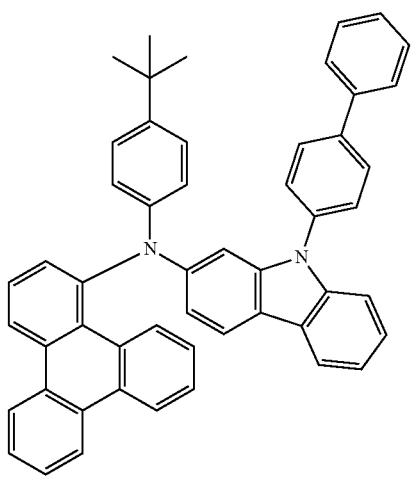
82
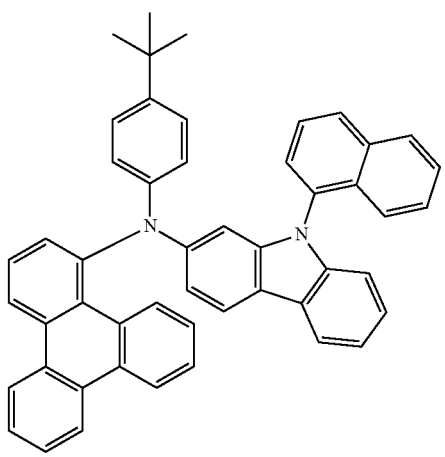
83
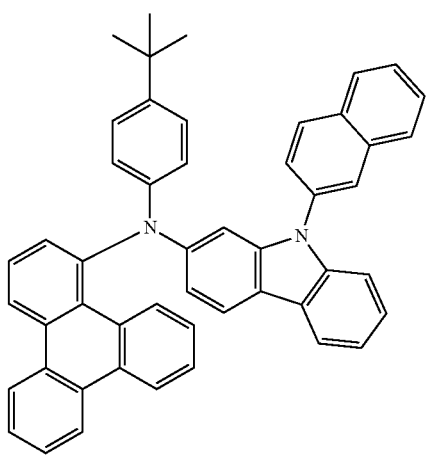

115  
-continued
84
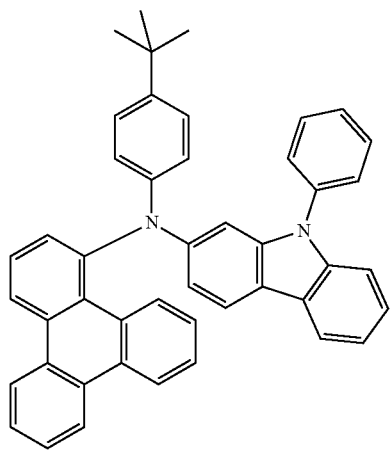
85
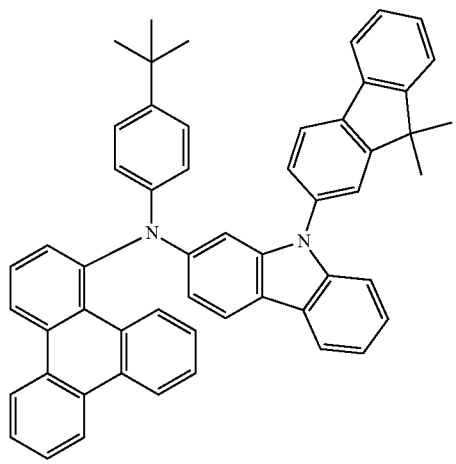
86
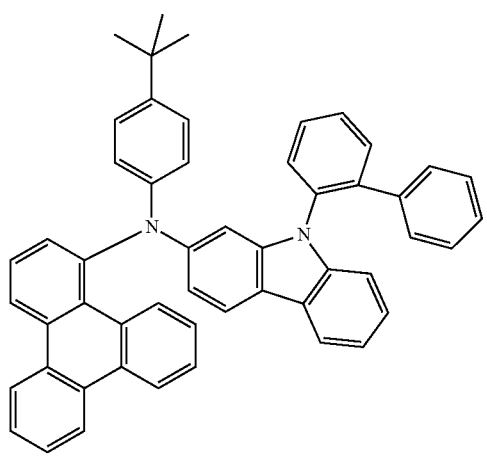
116  
-continued
87
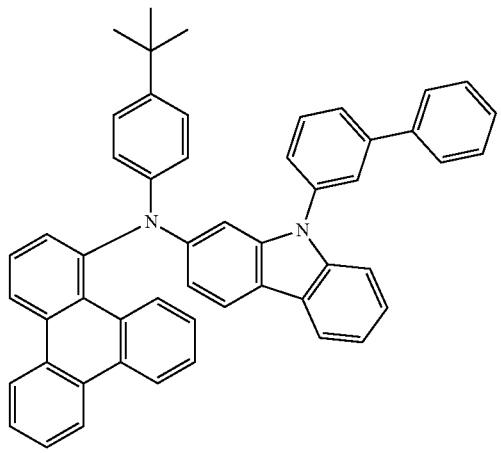
88
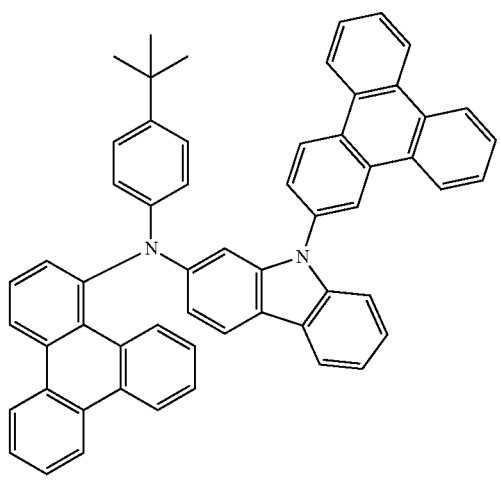
89
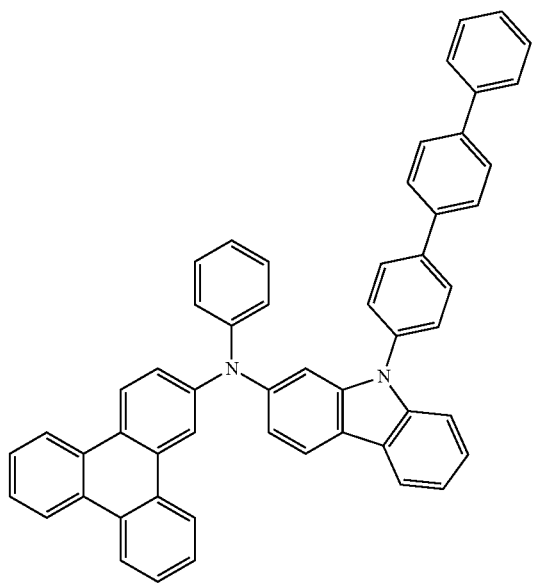

90 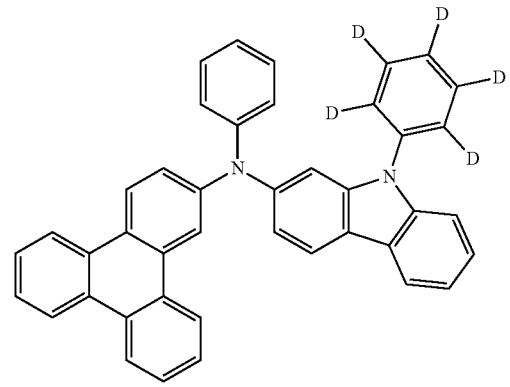

91 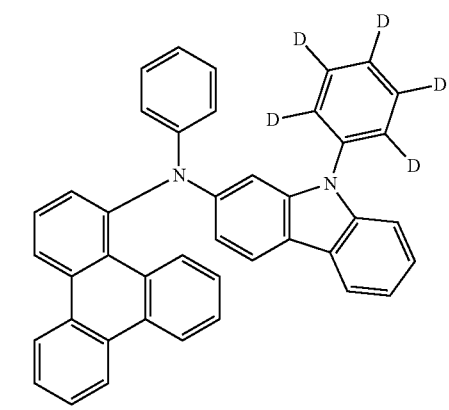

92 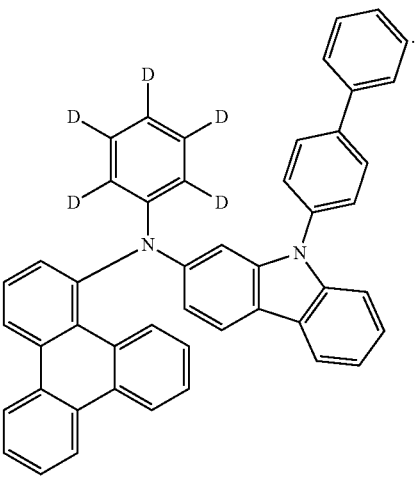

93 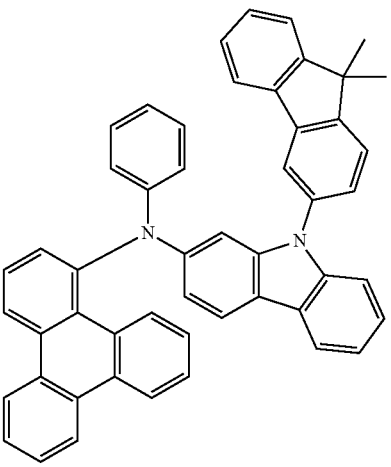

94

7. An organic light emitting device comprising:
a first electrode;
a second electrode; and
one or more organic material layers disposed between the first electrode and the second electrode,
wherein one or more layers of the organic material layers comprise the compound of claim 1.

8. The organic light emitting device of claim 7, wherein the organic material layer comprises one or more layers of an electron transport layer, an electron injection layer, and a layer which transports and injects electrons simultaneously, and one or more layers of the layers comprise the compound.

9. The organic light emitting device of claim 7, wherein the organic material layer comprises a light emitting layer, and the light emitting layer comprises the compound as a host of the light emitting layer.

10. The organic light emitting device of claim 7, wherein the organic material layer comprises one or more layers of a hole injection layer, an electron blocking layer, a hole transport layer, and a layer which injects and transports holes simultaneously, and one or more layers of the layers comprise the compound.

11. The organic light emitting device of claim 7, wherein the organic material layer comprises the compound as a host, and comprises another organic compound, a metal, or a metal compound as a dopant.

12. The organic light emitting device of claim 7, wherein the organic material layer comprises a light emitting layer, and the light emitting layer comprises a compound represented by the following Chemical Formula 6:

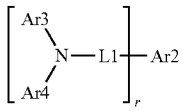

[Chemical Formula 6]

in Chemical Formula 6,

Ar2 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L1 is a direct bond; a substituted or unsubstituted arylene group; or a substituted or unsubstituted heteroarylene group, Ar3 and Ar4 are the same as or different from each other, and are each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or optionally combine with each other to form a substituted or unsubstituted ring, r is an integer of 1 or more, and when r is 2 or more, the substituents in the parenthesis are the same as or different from each other.

13. The organic light emitting device of claim 12, wherein L1 is a direct bond, Ar2 is a substituted or unsubstituted divalent pyrene group, Ar3 and A4 are the same as or different from each other, and are each independently an aryl group which is substituted or unsubstituted with a germanium group substituted with an alkyl group, and r is 2.

14. The organic light emitting device of claim 7, wherein the organic material layer comprises a light emitting layer, and the light emitting layer comprises a compound represented by the following Chemical Formula 7:

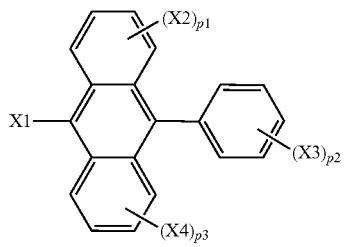

[Chemical Formula 7]

in Chemical Formula 7,

X1 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

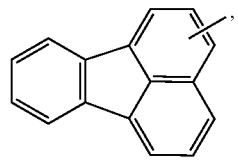

X3 is a phenyl group, a 1-naphtyl group, a 2-naphtyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, X2 and X4 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, p2 is an integer of 1 to 5, p1 and p3 are each an integer of 1 to 4, and when p1 to p3 are each 2 or more, the substituents in the parenthesis are the same as or different from each other.

15. The organic light emitting device of claim 14, wherein X1 is a 1-naphthyl group, and X3 is a 2-naphthyl group.

16. The organic light emitting device of claim 12, wherein the light emitting layer comprises a compound represented by the following Chemical Formula 7:

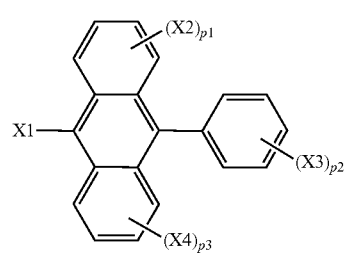

[Chemical Formula 7]

in Chemical Formula 7,

X1 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

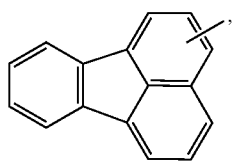

X3 is a phenyl group, a 1-naphtyl group, a 2-naphtyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, X2 and X4 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, p2 is an integer of 1 to 5, p1 and p3 are each an integer of 1 to 4, and when p1 to p3 are each 2 or more, the substituents in the parenthesis are the same as or different from each other.

\* \* \* \* \*